US007740849B2

(12) United States Patent
Karumanchi et al.

(10) Patent No.: US 7,740,849 B2
(45) Date of Patent: Jun. 22, 2010

(54) USE OF COMPOUNDS THAT BIND SOLUBLE ENDOGLIN AND SFLT-1 FOR THE TREATMENT OF PREGNANCY RELATED HYPERTENSIVE DISORDERS

(75) Inventors: S. Ananth Karumanchi, Chestnut Hill, MA (US); Vikas P. Sukhatme, Newton, MA (US); Mourad Toporsian, Toronto (CA); Michelle V. Letarte, Toronto (CA)

(73) Assignees: Beth Israel Deaconess Medical Center, Boston, MA (US); The Hospital for Sick Children (CA)

( * ) Notice: Subject to any disclaimer, the term of this patent is extended or adjusted under 35 U.S.C. 154(b) by 539 days.

(21) Appl. No.: 11/443,920

(22) Filed: May 31, 2006

(65) Prior Publication Data

US 2007/0104707 A1 May 10, 2007

Related U.S. Application Data

(63) Continuation-in-part of application No. 11/235,577, filed on Sep. 26, 2005.

(60) Provisional application No. 60/613,170, filed on Sep. 24, 2004.

(51) Int. Cl.
*A61K 39/395* (2006.01)
(52) U.S. Cl. .............. 424/139.1; 424/140.1; 424/145.1; 424/158.1; 424/85.1; 514/2; 514/8; 530/351; 530/387.9; 530/388.24; 530/388.25
(58) Field of Classification Search ........................ None
See application file for complete search history.

(56) References Cited

U.S. PATENT DOCUMENTS

| 5,194,596 | A | 3/1993 | Tischer et al. |
| 5,219,739 | A | 6/1993 | Tischer et al. |
| 5,238,819 | A | 8/1993 | Roberts et al. |
| 5,240,848 | A | 8/1993 | Keck et al. |
| 5,332,671 | A | 7/1994 | Ferrara et al. |
| 5,543,138 | A | 8/1996 | Keith |
| 5,641,636 | A | 6/1997 | Strauss et al. |
| 5,660,827 | A | 8/1997 | Thorpe et al. |
| 5,712,395 | A | 1/1998 | App et al. |
| 5,763,441 | A | 6/1998 | App et al. |
| 5,830,847 | A | 11/1998 | Letarte et al. |
| 5,830,879 | A | 11/1998 | Isner |
| 5,910,482 | A | 6/1999 | Yallampalli et al. |
| 5,928,641 | A | 7/1999 | Seon |
| 5,958,715 | A | 9/1999 | Muller |
| 6,100,071 | A | 8/2000 | Davis-Smyth et al. |
| 6,258,787 | B1 | 7/2001 | Isner |
| 6,365,157 | B2 | 4/2002 | Rockwell et al. |
| 6,376,199 | B1 | 4/2002 | Caniggia et al. |
| 6,399,585 | B1 | 6/2002 | Larson et al. |
| 6,410,322 | B1 | 6/2002 | Robinson |
| 6,447,768 | B1 | 9/2002 | Van Zonneveld et al. |
| 6,562,957 | B1 | 5/2003 | Letarte et al. |
| 6,660,534 | B2 | 12/2003 | McVicker et al. |
| 6,677,300 | B1 | 1/2004 | Schreiner et al. |
| 7,030,083 | B2 | 4/2006 | Schreiner et al. |
| 7,335,362 | B2 | 2/2008 | Karumanchi et al. |
| 7,407,659 | B2 | 8/2008 | Karumanchi et al. |
| 7,435,419 | B2 | 10/2008 | Karumanchi et al. |
| 2003/0049823 | A1 | 3/2003 | Sessa |
| 2003/0099651 | A1 | 5/2003 | Leibovitz |
| 2003/0114407 | A1 | 6/2003 | Monia et al. |
| 2003/0114412 | A1 | 6/2003 | Ward et al. |
| 2003/0144298 | A1 | 7/2003 | Curwen et al. |
| 2003/0220262 | A1 | 11/2003 | Schreiner et al. |
| 2004/0038305 | A1 | 2/2004 | Poston et al. |
| 2004/0126828 | A1 | 7/2004 | Karumanchi et al. |
| 2005/0025762 | A1 | 2/2005 | Karumanchi et al. |
| 2005/0043227 | A1 | 2/2005 | Compernolle et al. |
| 2005/0148040 | A1 | 7/2005 | Thadhani et al. |
| 2005/0170444 | A1 | 8/2005 | Karumanchi et al. |
| 2005/0256199 | A1 | 11/2005 | Durley et al. |
| 2006/0067937 | A1 | 3/2006 | Karumanchi et al. |
| 2006/0183175 | A1 | 8/2006 | Buhimschi et al. |

FOREIGN PATENT DOCUMENTS

| WO | WO 98/28006 | 7/1998 |
| WO | WO 02/37120 | 5/2002 |
| WO | WO 2004/008946 | 1/2004 |
| WO | WO 2005/077007 | 8/2005 |
| WO | WO 2006/034507 A2 | 3/2006 |
| WO | WO 2006/069373 | 6/2006 |
| WO | WO 2006/034507 A3 | 4/2007 |
| WO | WO 2008/030283 | 3/2008 |

OTHER PUBLICATIONS

The Merck Manual of Diagnosis and Therapy, 17th edition, 1999, Merck Research Laboratories, pp. 2057-2059.*

(Continued)

*Primary Examiner*—Michael Szperka
(74) *Attorney, Agent, or Firm*—Kristina Bieker-Brady; Kimya F. Harris; Clark & Elbing LLP

(57) ABSTRACT

Disclosed herein are methods for treating a pregnancy related hypertensive disorder, such as pre-eclampsia and eclampsia, using combinations of compounds that alter soluble endoglin and sFlt-1 expression levels or biological activity. Also disclosed are methods for treating a pregnancy related hypertensive disorder, such as pre-eclampsia and eclampsia, using compounds that increase endothelial nitric oxide synthase levels or biological activity.

37 Claims, 41 Drawing Sheets
(6 of 41 Drawing Sheet(s) Filed in Color)

OTHER PUBLICATIONS

Geissbuehler et al., Arch Gynecol Obstet, 2007, 276:151-157.*
Irminger-Finger et al., International Journal of Biochemistry and Cell Biology, 2008, 40:1979-1983.*
Bouloumie et al., "Vascular endothelial growth factor up-regulates nitric oxide synthase expression in endothelial cells," *Cardiovasc. Res.* 41: 773-780 (1999).
Lenasi et al., "Amlodipine activates the endothelial nitric oxide synthase by altering phosphorylation on Ser$^{1177}$ and Thr$^{495}$," *Cardiovasc. Res.* 59: 844-853 (2003).
Ota et al., "Targets of transcriptional regulation by two distinct type I receptors for transforming growth factor-β in human umbilical vein endothelial cells," *J. Cell. Physiol.*, 193: 299-318 (2002).
Tai et al., "Endothelial nitric oxide synthase: a new paradigm for gene regulation in the injured blood vessel," *Arterioscler. Thromb. Vasc. Biol.* 24: 405-412 (2004).
International Search Report dated Jan. 31, 2008 (PCT/US2007/12787).
Guerrero-Esteo et al., "Extracellular and cytoplasmic domains of endoglin interact with the transforming growth factor-β receptors I and II," *J. Biol. Chem.* 277: 29197-29209 (2002).
Li et al., "Plasma levels of soluble CD105 correlate with metastasis in patients with breast cancer," *Int. J. Cancer (Pred. Oncol.)* 89:122-126 (2000).
Miyazono, "Positive and negative regulation of TGF-β signaling," *J. Cell Science* 113: 1101-1109 (2000).
Miyazono et al., "Divergence and convergence of TGF-β/BMP signaling," *J. Cell. Physiol.* 187: 265-276 (2001).
Nohe et al., "Signal transduction of bone morphogenetic protein receptors," *Cell. Signal.* 16: 291-299 (2004).
Oswald et al., "Mesenchymal stem cells can be differentiated into endothelial cells in vitro," *Stem Cells* 22: 377-384 (2004).
Schultze-Mosgau et al., "Improved free vascular graft survival in an irradiated surgical site following topical application of rVEGF," *Int. J. Radiation Oncol. Biol. Phys.* 57: 803-812 (2003).
Takahashi et al., "Antiangiogenic therapy of established tumors in human skin/severe combined immunodeficiency mouse chimeras by anti-endoglin (CD105) monoclonal antibodies, and synergy between anti-endoglin antibody and cyclophosphamide," *Cancer Res.* 61: 7846-7854 (2001).
Office Action for U.S. Appl. No. 11/235,577 mailed on Jul. 25, 2008.
Reply to Office Action for U.S. Appl. No. 11/235,577, filed on Nov. 25, 2008.
Office Action for U.S. Appl. No. 11/235,577 mailed on Feb. 18, 2009.
Reply to Office Action for U.S. Appl. No. 11/235,577, filed on May 18, 2009.
European Search Report issued on Jun. 11, 2008 for EP 05815390.9.
European Supplemental Search Report issued on Oct. 8, 2008 for EP 05815390.9.
European Examination Report issued on Mar. 20, 2009 for Application No. EP 05815390.9.
Singapore Written Opinion and Search Report issued on Oct. 30, 2008 for Application No. 200702085-2.
Ahmed et al., "Regulation of Placental Vascular Endothelial Growth Factor (VEGF) and Placenta Growth Factor (PlGF) and Soluble Flt-1 by Oxygen- A Review," *Placenta* 21:S16-S24 (2000).
Alberts et al., "Endoglin Gene Polymorphism as a Risk Factor for Sporadic Intracerebral Hemorrhage," *Ann. Neurol.* 41:683-86 (1997).
Al Kadi et al., "A prospective, longitudinal study of the renin-angiotensin system, prostacyclin and thromboxane in the first trimester of normal human pregnancy: association with birth weight," *Hum. Reprod.* 20:3157-3162 (2005).
Barleon et al., "Soluble VEGFR-1 Secreted by Endothelial Cells and Monocytes is Present in Human Serum and Plasma From Healthy Donors," *Angiogenesis* 4:143-54 (2001).
Belgore et al., "Measurement of Free and Complexed Soluble Vascular Endothelial Growth Factor Receptor, Flt-1, in Fluid Samples: Development and Application of Two New Immunoassays," *Clin. Sci.* 100:567-75 (2001).
Belgore et al., "Plasma Levels of Vascular Endothelial Growth Factor and Its Soluble Receptor (SFlt-1) in Essential Hypertension," *Am. J. Cardiol.* 87:805-7 (2001).
Belgore et al., "sFlt-1, a Potential Antagonist for Exogenous VEGF," *Circulation* 102:E108-E109 (2000).
Belgore et al., "Vascular Endothelial Growth Factor and its Receptor, Flt-1, in Smokers and Non-Smokers," *Br. J. Biomed. Sci.* 57: 207-13 (2000).
Bellon et al., "Identification and expression of two forms of the human transforming growth factor-β-binding protein endoglin with distinct cytoplasmic regions," *Eur. J. Immunol.* 23:2340-2345 (1993).
Bernabeu et al., "Interaction between the CD45 antigen and phytohemagglutinin. Inhibitory effect on the lectin-induced T cell proliferation by anti-CD45 monoclonal antibody," *Eur. J. Immunol.* 17:1461-1466 (1987).
Brennecke et al., "Reduction of placental nitric oxide synthase activity in pre-eclampsia," *Clin. Sci.* 93:51-55 (1997).
Brockelsby et al., "VEGF Via VEGF Receptor-1 (Flt-1) Mimics Preeclamptic Plasma in Inhibiting Uterine Blood Vessel Relaxation in Pregnancy: Implications in the Pathogenesis of Preeclampsia," *Lab. Invest.* 79:1101-11 (1999).
Brown et al., "Vascular Permeability Factor mRNA and Protein Expression in Human Kidney," *Kidney Int.* 42: 1457-61 (1992).
Buhimschi et al., "Pre-eclampsia-like conditions produced by nitric oxide inhibition: effects of L-arginine, D-arginine and steroid hormones," *Hum. Reprod.* 10:2723-2730 (1995).
Burrows et al., "Up-regulation of Endoglin on Vascular Endothelial Cells in Human Solid Tumors: Implications for Diagnosis and Therapy," *Clin. Cancer Res.* 1:1623-34 (1995).
Calabro et al., "Differential levels of soluble endoglin (CD105) in myeloid malignancies," *J. Cell. Physiol.* 194:171-175 (2002).
Caniggia et al., "Endoglin Regulates Trophoblast Differentiation Along the Invasive Pathway in Human Placental Villous Explants," *Endocrinology* 138:4977-88 (1997).
Chaiworapongsa et al., "Plasma Soluble Vascular Endothelial Growth Factor Receptor-1 Concentration is Elevated Prior to the Clinical Diagnosis of Pre-eclampsia," *J. Matern. Fetal Neonatal. Med.* 17:3-18 (2005).
Charnock-Jones et al., "Determination of the Circulating Levels of the Soluble Form of the VEGF-R1 (sFlt-1) in Women at High Risk of Developing Pre-Eclampsia," *J. Soc. Gynecol. Investig.* 10:166A Abstract No. 230 (2003).
Charnock-Jones et al., "Identification and Localization of Alternately Spliced mRNAs for Vascular Endothelial Growth Factor in Human Uterus and Estrogen Regulation in Endometrial Carcinoma Cell Lines," *Biol. Reprod.* 48:1120-28 (1993).
Clark et al., "A Vascular Endothelial Growth Factor Antagonist is Produced by the Human Placenta and Released into the Maternal Circulation," *Biol. Reprod.* 59:1540-48 (1998).
Cockell et al., "Human Placental Syncytiotrophoblast Microvillous Membranes Impair Maternal Vascular Endothelial Function," *Br. J. Obstet. Gynaecol.* 104:235-40 (1997).
Eremina et al., "Glomerular-Specific Alterations of VEGF-A Expression Lead to Distinct Congenital and Acquired Renal Diseases," *J. Clin. Invest.* 111:707-16 (2003).
Ferguson, "Meeting Highlights: Highlights of the 48$^{th}$ Scientific Sessions of the American College of Cardiology," *Circulation* 100:570-75 (1999).
Ferrara et al., "The Role of Vascular Endothelial Growth Factor in Angiogensis," *Acta. Haemato.* 106:148-56 (2001).
Fonsatti et al., "Endoglin (CD105): A Powerful Therapeutic Target on Tumor-associated Angiogenetic Blood Vessels," *Oncogene* 22:6557-63 (2003).
Fonsatti et al., "Endoglin is a Suitable Target for Efficient Imaging of Solid Tumors: In Vivo Evidence in a Canine Mammary Carcinoma Model," *Clin. Cancer Res.* 6:2037-43 (2000).
Fonsatti et al., "Emerging Role of Endoglin (CD105) as a Marker of Angiogenesis with Clinical Potential in Human Malignancies," *Curr. Cancer Drug Targets* 3:427-32 (2003).
Fulton et al., "Regulation of endothelium-derived nitric oxide production by the protein kinase Akt," *Nature* 399:597-601 (1999).

Gille et al., "Analysis of Biological Effects and Signaling Properties for Flt-1 (VEGFR-1) and KDR (VEGFR-2)," *J. Biol. Chem.* 276:3222-30 (2001).

Hayashi et al., "Changes in Urinary Excretion of Six Biochemical Parameters in Normotensive Pregnancy and Preeclampsia," *Am. J. Kidney Dis.* 39:392-400 (2002).

He et al., "Alternative Splicing for Vascular Endothelial Growth Factor (VEGF)-R1 (FLT-1) Pre-mRNA is Important for the Regulation of VEGF Activity," *Mol. Endocrinol.* 13:537-45 (1999).

He et al., "Vascular Endothelial Growth Factor Signals Endothelial Cell Production of Nitric Oxide and Prostacyclin Through Flk-1/KDR Activation of c-Src," *J. Biol. Chem.* 274:25130-35 (1999).

Heeschen et al., "Nicotine Stimulates Angiogenesis and Promotes Tumor Growth and Atherosclerosis," *Nat. Med.* 7:833-39 (2001).

Helske et al., "Expression of Vascular Endothelial Growth Factor Receptors 1, 2,and 3 in Placentas From Normal and Complicated Pregnancies," *Mol. Hum. Reprod.* 7:205-10 (2001).

Hornig et al., "Release and Complex Formation of Soluble VEGFR-1 from Endothelial Cells and Biological Fluids," *Lab. Invest.* 80:443-54 (2000).

Hunter et al., "Serum Levels of Vascular Endothelial Growth Factor in Preeclamptic and Normotensive Pregnancy," *Hypertension* 36:965-69 (2000).

Jakubowski et al., "Biochemical and pharmacological activity of arene-fused prostacylin analogues on human platelets," *Prostaglandins* 47:189-201 (1994).

Kendall et al., "Identification of a Natural Soluble Form of the Vascular Endothelial Growth Factor Receptor, FLT-1, and Its Heterodimerization with KDR," *Biochem. Biophys. Res. Commun.* 226:324-28 (1996).

Kendall et al., "Inhibition of Vascular Endothelial Cell Growth Factor Activity by an Endogenously Encoded Soluble Receptor," *Proc. Natl. Acad. Sci.* 90:10705-9 (1993).

Kincaid-Smith, "The Renal Lesion of Preeclampsia Revisited," *Am. J. Kidney Dis.* 17:144-48 (1991).

Kingsley, "The TGF-beta Superfamily: New Members, New Receptors, and New Genetic Tests of Function in Different Organisms," *Genes Dev.* 8:133-46 (1994).

Klockenbusch et al., "Platelet $PGI_2$ receptor affinity is reduced in pre-eclampsia," *Br. J. Clin. Pharmacol.* 41:616-618 (1996).

Koga et al., "Elevated Serum Soluble Vascular Endothelial Growth Factor Receptorl (sVEGFR-1) Levels in Women with Preeclampsia," *J. Clin. Endocrinol. Metab.* 88:2348-51 (2003).

Lain et al., "Contemporary Concepts of the Pathogenesis and Management of Preeclampsia," *JAMA* 287:3183-86 (2002).

Levine et al., "Circulating Angiogenic Factors and the Risk of Preeclampsia," *N. Engl. J. Med.* 350:672-83 (2004).

Levine et al., "Trial of Calcium for Preeclampsia Prevention (CPEP): Rationale, Design, and Methods," *Control Clin. Trials* 17:442-69 (1996).

Levine et al., "Trial of Calcium to Prevent Preeclampsia," *N. Engl. J. Med.* 337:69-76 (1997).

Levine et al., "Two-Stage Elevation of Cell-Free Fetal DNA in Maternal Sera Before Onset of Preeclampsia," *Am. J. Obstet. Gynecol.* 190:707-13 (2004).

Levine et al., "Urinary Placental Growth Factor and Risk of Preeclampsia," *JAMA* 293:77-85 (2005).

Li et al., "CD105 Antagonizes the Inhibitory Signaling of Transforming Growth Factor β1 on Human Vascular Endothelial Cells," *FASEB J.* 14:55-64 (2000).

Lim et al., "Human Cytotrophoblast Differentiation/Invasion is Abnormal in Pre-Eclampsia," *Am. J. Pathol.* 151:1809-18 (1997).

Livingston et al., "Placenta Growth Factor is not an Early Marker of the Development of Severe Preeclampsia," *Am. J. Obstet. Gynecol.* 184:1218-20 (2001).

Livingston et al., "Reductions of Vascular Endothelial Growth Factor and Placental Growth Factor Concentrations in Severe Preeclampsia," *Am. J. Obstet. Gynecol.* 183:1554-57 (2000).

Luttun et al., "Soluble VEGF Receptor Flt1: The Elusive Preeclampsia Factor Discovered?" *J. Clin. Invest.* 111: 600-2 (2003).

Makondo et al., "Hepatocyte growth factor activates endothelial nitric oxide synthase by $Ca^{2+}$—and phosphoinositide 3-kinase/Akt-dependent phosphorylation in aortic endothelial cells," *Biochem. J.* 374:63-69 (2003).

Massague et al., "The TGF-beta Family and Its Composite Receptors," *Trends Cell. Biol.* 4:172-78 (1994).

Massague, "TGF-beta Signal Transduction," *Annu. Rev. Biochem.* 67:753-91 (1998).

Masuda et al., "Vascular Endothelial Growth Factor Enhances Glomerular Capillary Repair and Accelerates Resolution of Experimentally Induced Glomerulonephritis," *Am. J. Pathol.* 159:599-608 (2001).

Maynard et al., "Excess Placental Soluble fms-Like Tyrosine Kinase 1 (sFlt1) May Contribute to Endothelial Dysfunction, Hypertension, and Proteinuria in Preeclampsia," *J. Clinical Invest.* 111:649-58 (2003).

McAllister et al., "Endoglin, a TGF-β binding protein of endothelial cells, is the gene for hereditary haemorrhagic telangiectasia type 1," *Nat. Genet.* 8:345-351 (1994).

Mills et al., "Prostacyclin and Thromboxane Changes Predating Clinical Onset of Preeclampsia," *JAMA* 281: 356-62 (1999).

Morbidelli et al., "Nitric Oxide Mediates Mitogenic Effect of VEGF on Coronary Venular Endothelium," *Am. J. Physiol.* 270:H411-H415 (1996).

Mortensen et al., "Smoking, Sex of the Offspring, and Risk of Placental Abruption, Placenta Previa, and Preeclampsia : A Population-Based Cohort Study," *Acta. Obstet. Gynecol. Scand.* 80:894-98 (2001).

Myatt et al., "Endothelial nitric oxide synthase in placental villous tissue from normal, pre-eclamptic and intrauterine growth restricted pregnancies," *Hum. Reprod.* 12:167-172 (1997).

Myers et al., "Hypertensive Diseases and Eclampsia," *Curr. Opin. Obstet. Gynecol.* 14:119-25 (2002).

Neufeld et al., "Similarities and Differences Between the Vascular Endothelial Growth Factor (VEGF) Splice Variants," *Cancer Metastasis Rev.* 15:153-58 (1996).

Newman et al., "Cigarette Smoking and Pre-Eclampsia: Their Association and Effects on Clinical Outcomes," *J. Matern. Fetal. Med.* 10:166-70 (2001).

Ong et al., "First-Trimester Maternal Serum Levels of Placenta Growth Factor as Predictor of Preeclampsia and Fetal Growth Restriction," *Obstet. Gynecol.* 98:608-11 (2001).

Ostendorf et al., "$VEGF_{165}$ Mediates Glomerular Endothelial Repair," *J. Clin. Invest.* 104:913-923 (1999).

Page et al., "Excessive Placental Secretion of Neurokinin B During the Third Trimester Causes Pre-Eclampsia," *Nature* 405:797-800 (2000).

Papapetropoulos et al., "Vanadate is a potent activator of endothelial nitric-oxide synthase: evidence for the role of the serine/threonine kinase akt and the 90-kDa heat shock protein," *Mol. Pharmacol.* 65:407-415 (2004).

Paternoster et al., "Markers of Tubular Damage in Pre-Eclampsia," *Minerva Ginecol.* 51:373-77 (1999).

Polliotti et al., "Second-Trimester Maternal Serum Placental Growth Factor and Vascular Endothelial Growth Factor for Predicting Severe, Early-Onset Preeclampsia," *Obstet. Gynecol.* 101:1266-74 (2003).

Raab et al., "Expression of Normal and Truncated Forms of Human Endoglin," *Biochem. J.* 339:579-88 (1999).

Regnault et al., "Placental Expression of VEGF, PIGF and their Receptors in a Model of Placental Insufficiency-Intrauterine Growth Restriction (PI-IUGR)," *Placenta* 23:132-44 (2002).

Roberts et al., "Pathogenesis and Genetics of Pre-Eclampsia," *Lancet* 357:53-56 (2001).

Roes et al., "High Levels of Urinary Vascular Endothelial Growth Factor in Women with Severe Preeclampsia," *Int. J. Biol. Markers* 19:72-75 (2004).

Sanchez et al., "Quercetin downregulates NADPH oxidase, increases eNOS activity and prevents endothelial dysfunction in spontaneously hypertensive rats," *J. Hypertens.* 24:75-84 (2006).

Sato et al., "Increased Pulmonary Vascular Contraction to Serotonin after Cardiopulmonary Bypass: Role of Cyclooxygenase," *J. Surg. Res.* 90:138-43 (2000).

Sibai, "Diagnosis and Management of Gestational Hypertension and Preeclampsia," *Obstet. Gynecol.* 102:181-92 (2003).

Sibai et al., "What We Have Learned About Preeclampsia," *Semin. Perinatol.* 27:239-46 (2003).

Sporn et al., "Transforming Growth Factor- β: Recent Progress and New Challenges," *J. Cell. Biol.* 119:1017-21 (1992).

Strevens et al., "Glomerular Endotheliosis in Normal Pregnancy and Pre-Eclampsia," *Br. J. Obstet. Gynecol.* 110: 831-36 (2003).

Su et al., "Decreased Maternal Serum Placenta Growth Factor in Early Second Trimester and Preeclampsia," *Obstet. Gynecol.* 97:898-904 (2001).

Sugimoto et al., "Neutralization of Circulating Vascular Endothelial Growth Factor (VEGF) by Anti-VEGF Antibodies and Soluble VEGF Receptor 1 (sFlt-1) Induces Proteinuria," *J. Biol. Chem.* 278:12605-8 (2003).

Taylor et al., "Longitudinal Serum Concentrations of Placental Growth Factor: Evidence for Abnormal Placental Angiogenesis in Pathologic Pregnancies," *Am. J. Obstet. Gynecol.* 188:177-82 (2003).

Thadhani et al., "First Trimester Placental Growth Factor and Soluble FMS-like Tyrosine Kinase 1 and Risk for Preeclampsia," *J. Clin. Endocrinol. Metab.* 89:770-75 (2004).

Tidwell et al., "Low Maternal Serum Levels of Placenta Growth Factor as an Antecedent of Clinical Preeclampsia," *Am. J. Obstet. Gynecol.* 184:1267-72 (2001).

Tjoa et al., "Plasma Placenta Growth Factor Levels in Midtrimester Pregnancies," *Obstet. Gynecol.* 98:600-7 (2001).

Torry et al., "Expression and Function of Placenta Growth Factor: Implications for Abnormal Placentation," *J. Soc. Gynecol. Investig.* 10:178-88 (1998).

Torry et al., "Preeclampsia is Associated with Reduced Serum Levels of Placenta Growth Factor," *Am. J. Obstet. Gynecol.* 179:1539-44 (1998).

Tucci et al., "rhVEGF and Experimental Rat Skin Flaps: Systemic or Local Administration and Morphological Characteristics," *Int. J. Artif. Organs* 24:743-51 (2001).

Velasco-Loyden et al., "The Shedding of Betaglycan is Regulated by Pervanadate and Mediated by Membrane Type Matrix Metalloprotease-1," *J. Biol. Chem.* 279:7721-33 (2004).

Vuorela et al., "Amniotic Fluid-Soluble Vascular Endothelial Growth Factor Receptor-1 in Preeclampsia," *Obstet. Gynecol.* 95:353-57 (2000).

Walker, "Pre-Eclampsia," *Lancet* 356:1260-65 (2000).

Whittaker et al., "Matrix Metalloproteinases and Their Inhibitors-Current Status and Future Challenges," *Cell Transmissions* 17:3-12 (2001).

Yamashita et al., "Endoglin Forms a Heteromeric Complex With the Signaling Receptors for Transforming Growth Factor-β," *J. Biol. Chem.* 269:1995-2001 (1994).

Zhou et al., "Preeclampsia is Associated With Faliure of Human Cytotrophoblasts to Mimic a Vascular Adhesion Phenotype. One Cause of Defective Endovascular Invasion in This Syndrome?" *J. Clin. Invest.* 99:2152-64 (1997).

Zhou et al., "Vascular Endothelial Growth Factor Ligands and Receptors that Regulate Human Cytotrophoblast Survival are Dysregulated in Severe Preeclampsia and Hemolysis, Elevated Liver Enzymes, and Low Platelets Syndrome," *Am. J. Pathol.* 160:1405-23 (2002).

Foreign Search Report U.S. Appl. No. SG 200500265-4, Oct. 7, 2005.

International Search Report U.S. Appl. No. PCT/US03/22892, Nov. 18, 2005.

International Search Report U.S. Appl. No. PCT/US2005/003884, Feb. 3, 2006.

\* cited by examiner

A. Predicted cDNA sequence of soluble endoglin (437 amino acids):

```
   1 atggaccgcg gcacgctccc tctggctgtt gccctgctgc tggccagctg cagcctcagc
  61 cccacaagtc ttgcagaaac agtccattgt gaccttcagc ctgtgggccc cgagagggac
 121 gaggtgacat ataccactag ccaggtctcg aagggctgcg tggctcaggc ccccaatgcc
 181 atccttgaag tccatgtcct cttcctggag ttcccaacgg gcccgtcaca gctggagctg
 241 actctccagg catccaagca aaatggcacc tggccccgag aggtgcttct ggtcctcagt
 301 gtaaacagca gtgtcttcct gcatctccag gccctgggaa tcccactgca cttggcctac
 361 aattccagcc tggtcacctt ccaagagccc ccggggtca acaccacaga gctgccatcc
 421 ttccccaaga cccagatcct tgagtgggca gctgagaggg gcccatcac ctctgctgct
 481 gagctgaatg accccagag catcctcctc cgactgggcc aagcccaggg gtcactgtcc
 541 ttctgcatgc tggaagccag ccaggacatg ggccgcacgc tcgagtggcg gccgcgtact
 601 ccagccttgg tccggggctg ccacttggaa ggcgtggccg gccacaagga ggcgcacatc
 661 ctgagggtcc tgccgggcca ctcggccggg cccggacgg tgacggtgaa ggtggaactg
 721 agctgcgcac ccggggatct cgatgccgtc ctcatcctgc agggtccccc ctacgtgtcc
 781 tggctcatcg acgccaacca caacatgcag atctggacca ctggagaata ctccttcaag
 841 atctttccag agaaaaacat tcgtggcttc aagctcccag acacacctca aggcctcctg
 901 ggggaggccc ggatgctcaa tgccagcatt gtggcatcct tcgtggagct accgctggcc
 961 agcattgtct cacttcatgc ctccagctgc ggtggtaggc tgcagacctc acccgcaccg
1021 atccagacca ctcctcccaa ggacacttgt agcccggagc tgctcatgtc cttgatccag
1081 acaaagtgtg ccgacgacgc catgaccctg gtactaaaga aagagcttgt tgcgcatttg
1141 aagtgcacca tcacgggcct gaccttctgg gacccagct gtgaggcaga ggacagggt
1201 gacaagtttg tcttgcgcag tgcttactcc agctgtggca tgcaggtgtc agcaagtatg
1261 atcagcaatg aggcggtggt caatatcctg tcgagctcat caccacagcg g
```

B. Predicted protein sequence:

Met D R G T L P L A V A L L L A S C S L S P T S L A E T V H C D L Q P V G P E R G E V
T Y T T S Q V S K G C V A Q A P N A I L E V H V L F L E F P T G P S Q L E L T L Q A S
K Q N G T W P R E V L L V L S V N S S V F L H L Q A L G I P L H L A Y N S S L V T F Q
E P P G V N T T E L P S F P K T Q I L E W A A E R G P I T S A A E L N D P Q S I L L R L
G Q A Q G S L S F C Met L E A S Q D Met G R T L E W R P R T P A L V R G C H L E G V
A G H K E A H I L R V L P G H S A G P R T V T V K V E L S C A P G D L D A V L I L Q G
P P Y V S W L I D A N H N Met Q I W T T G E Y S F K I F P E K N I R G F K L P D T P Q G
L L G E A R Met L N A S I V A S F V E L P L A S I V S L H A S S C G G R L Q T S P A P I
Q T T P P K D T C S P E L L Met S L I Q T K C A D D A Met T L V L K K E L V A H L K C
T I T G L T F W D P S C E A E D R G D K F V L R S A Y S S C G Met Q V S A S Met I S N
E A V V N I L S S S S P Q R

FIGURE 2

```
 26   ETVHCDLQPV  GPERGEVTYT  TSQVSKGCVA  QAPNAILEVH  VLFLEFPTGP
 76   SQLELTLQAS  KQNGTWPREV  LLVLSVNSSV  FLHLQALGIP  LHLAYNSSLV
126   TFQEPPGVNT  TELPSFPKTQ  ILEWAAERGP  ITSAAELNDP  QSILLRLGQA
176   QGSLSFCMLE  ASQDMGRTLE  WRPRTPALVR  GCHLEGVAGH  KEAHILRVLP
226   GHSAGPRTVT  VKVELSCAPG  DLDAVLILQG  PPYVSWLIDA  NHNMQIWTTG
276   EYSFKIFPEK  NIRGFKLPDT  PQGLLGEARM  LNASIVASFV  ELPLASIVSL
326   HASSCGGRLQ  TSPAPIQTTP  PKDTCSPELL  MSLIQTKCAD  DAMTLVLKKE
376   LVAHLKCTIT  GLTFWDPSCE  AEDRGDKFVL  RSAYSSCGMQ  VSASMISNEA
426   VVNILSSSSP  QRKKVHCLNM  DSLSFQLGLY  LSPHFLQASN  TIEPGQQSFV
476   QVRVSPSVSE  FLLQLDSCHL  DLGPEGGTVE  LIQGRAAKGN  CVSLLSPSPE
526   GDPRFSFLLH  FYTVPIPKTG  TLSCTVALRP  KTGSQDQEVH  RTVFMRLNII
576   SPDLSGCTSK  GLVLPAVLGI  TFGAFLIGAL  LTAALWYIYS  HTRSPSKREP
626   VVAVAAPASS  ESSSTNHSIG  STQSTPCSTS  SMA
```

FIGURE 30B

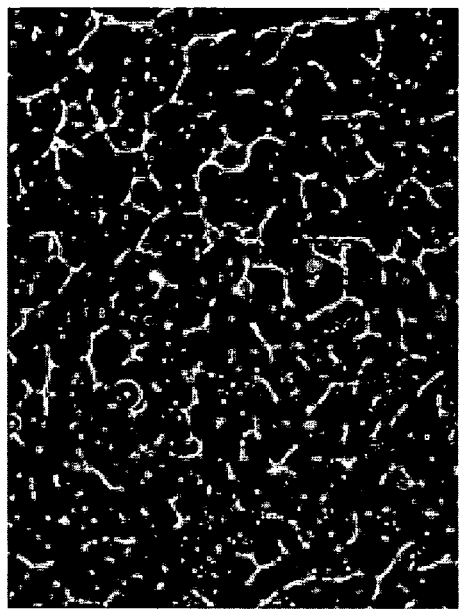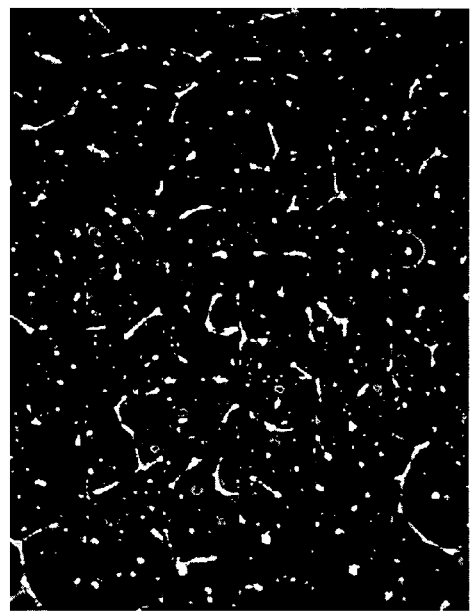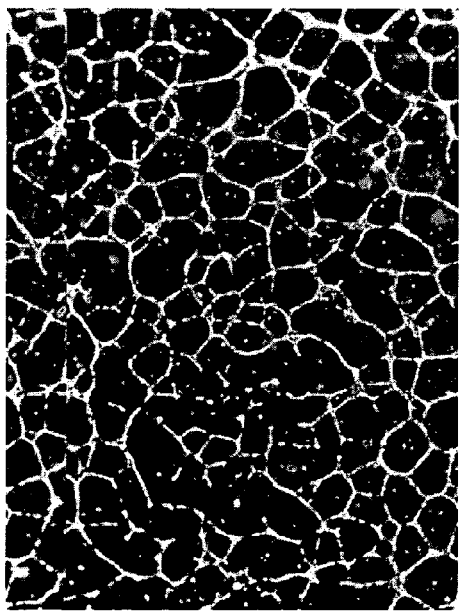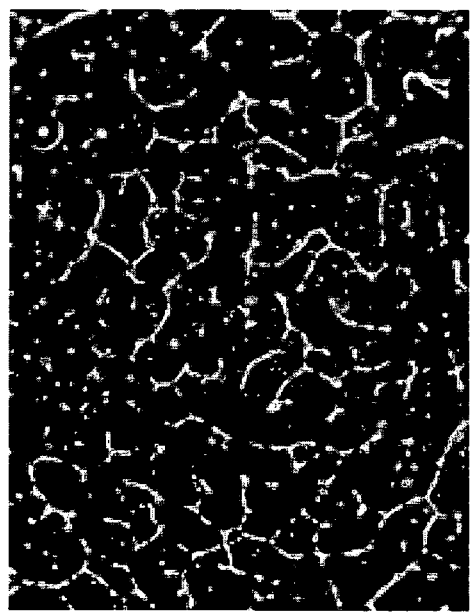
FIGURE 31

Upper panels: placenta
Lower panels: liver

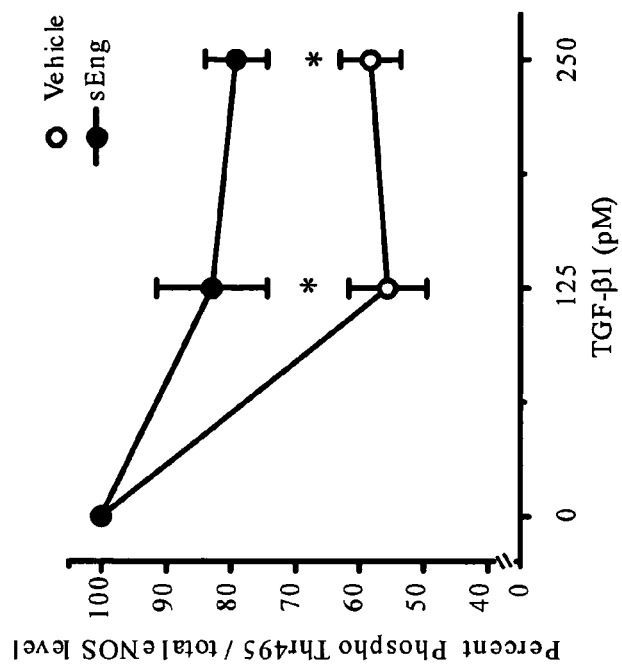
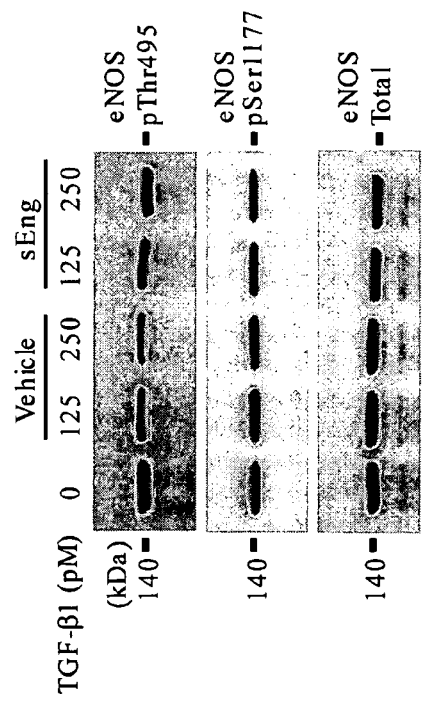
FIGURE 35D

US 7,740,849 B2

USE OF COMPOUNDS THAT BIND SOLUBLE ENDOGLIN AND SFLT-1 FOR THE TREATMENT OF PREGNANCY RELATED HYPERTENSIVE DISORDERS

CROSS-REFERENCE TO RELATED APPLICATIONS

This application is a continuation-in-part of U.S. patent application Ser. No. 11/235,577, filed Sep. 26, 2005, which claims the benefit of U.S. provisional application No. 60/613,170, filed Sep. 24, 2004, each of which is herein incorporated by reference.

STATEMENT AS TO FEDERALLY SPONSORED RESEARCH

This invention was made in part with support from the government through NIH Grant Nos. DK 064255 and HL 079594. The government has certain rights in the invention.

FIELD OF THE INVENTION

In general, this invention relates to the detection and treatment of subjects having a pregnancy related hypertensive disorder.

BACKGROUND OF THE INVENTION

Pre-eclampsia is a syndrome of hypertension, edema, and proteinuria that affects 5 to 10% of pregnancies and results in substantial maternal and fetal morbidity and mortality. Pre-eclampsia accounts for at least 200,000 maternal deaths worldwide per year. The symptoms of pre-eclampsia typically appear after the $20^{th}$ week of pregnancy and are usually detected by routine measuring of the woman's blood pressure and urine. However, these monitoring methods are ineffective for diagnosis of the syndrome at an early stage, which could reduce the risk to the subject or developing fetus, if an effective treatment were available.

Currently there are no known cures for pre-eclampsia. Pre-eclampsia can vary in severity from mild to life threatening. A mild form of pre-eclampsia can be treated with bed rest and frequent monitoring. For moderate to severe cases, hospitalization is recommended and blood pressure medication or anticonvulsant medications to prevent seizures are prescribed. If the condition becomes life threatening to the mother or the baby the pregnancy is terminated and the baby is delivered pre-term.

The proper development of the fetus and the placenta is mediated by several growth factors or angiogenic factors. One of these angiogenic factors is endoglin, also known as CD105. Endoglin is a homodimeric cell membrane glycoprotein that is predominantly expressed on endothelial cells such as syncytiotrophoblasts, human unbilical vein endothelial cells (HUVEC), and on vascular endothelial cells. Endoglin shares sequence identity with betaglycan, a transforming growth factor (TGF)-β receptor (TβR) type III. Endoglin has been shown to be a regulatory component of the TGF-β receptor complex, which modulates angiogenesis, proliferation, differentiation, and apoptosis. Endoglin also binds several other members of the TGF-β superfamily including activin-A, bone morphogenic protein (BMP)-2 and BMP-7. In particular, endoglin binds TGF-β1 and TGF-β3 with high affinity and forms heterotrimeric associations with the TGF-β signaling receptors types I and II. Mutations in the coding region of the endoglin gene are responsible for haemorrhagic telangiectasia type 1 (HHT1), a dominantly inherited vascular disorder characterized by multisystemic vascular dysplasia and recurrent hemorrhage. While endoglin immunoreactivity has been previously detected at increased levels in the plasma of patients with metastatic breast and colorectal cancer, its biochemical characteristics have not been determined and its exact functional role in the pathogenesis of cancer is unclear. Soluble endoglin production has not been reported to be associated with pre-eclampsia or normal pregnancy.

Several factors have been reported to have an association with fetal and placental development and, more specifically, with pre-eclampsia. They include vascular endothelial growth factor (VEGF), soluble Flt-1 receptor (sFlt-1), and placental growth factor (PlGF). VEGF is an endothelial cell-specific mitogen, an angiogenic inducer, and a mediator of vascular permeability. VEGF has also been shown to be important for glomerular capillary repair. VEGF binds as a homodimer to one of two homologous membrane-spanning tyrosine kinase receptors, the fms-like tyrosine kinase (Flt-1) and the kinase domain receptor (KDR), which are differentially expressed in endothelial cells obtained from many different tissues. Flt-1, but not KDR, is highly expressed by trophoblast cells which contribute to placental formation. PlGF is a VEGF family member that is also involved in placental development. PlGF is expressed by cytotrophoblasts and syncytiotrophoblasts and is capable of inducing proliferation, migration, and activation of endothelial cells. PlGF binds as a homodimer to the Flt-1 receptor, but not the KDR receptor. Both PlGF and VEGF contribute to the mitogenic activity and angiogenesis that are critical for the developing placenta.

sFlt-1, which lacks the transmembrane and cytoplasmic domains of the receptor, was recently identified in a cultured medium of human umbilical vein endothelial cells and in vivo expression was subsequently demonstrated in placental tissue. sFlt-1 binds to VEGF with a high affinity but does not stimulate mitogenesis of endothelial cells. Careful regulation of angiogenic and mitogenic signaling pathways is critical for maintaining appropriate proliferation, migration, and angiogenesis by trophoblast cells in the developing placenta.

There is a need for methods of accurately diagnosing subjects at risk for or having pre-eclampsia or eclampsia, particularly before the onset of the most severe symptoms. A treatment is also needed.

SUMMARY OF THE INVENTION

We have discovered methods for diagnosing and treating pregnancy related hypertensive disorders, including pre-eclampsia and eclampsia.

Using gene expression analysis, we have discovered that levels of soluble endoglin (sEng) are markedly elevated in placental tissue samples from pregnant women suffering from pregnancy complications associated with hypertension, including pre-eclampsia. Using western blotting, we have also discovered that soluble endoglin protein levels are elevated in blood serum samples taken from women with a pregnancy related hypertensive disorder, such as pre-eclampsia or eclampsia. Soluble endoglin may be formed by cleavage of the extracellular portion of the membrane bounds form by proteolytic enzymes. We have discovered that the soluble endoglin detected in these samples contains a minimum of the first 381 amino acids (excluding the leader peptide, 406 including the leader peptide) of the amino terminal portion of the full-length endoglin. Excess soluble endoglin in pre-eclampsia may be depleting the placenta of necessary amounts of these essential angiogenic and mitogenic factors by preventing binding of TGF-β1 to TβRII on endothelial cells leading to decreased signaling, as described herein. We have also discovered that soluble endoglin interferes with TGF-β1 signaling and endothelial nitric oxide synthase (eNOS) activation in endothelial cells, thereby disrupting key homeostatic mechanisms necessary for maintenance of vascular health. We demonstrate that soluble endoglin prevents binding of TGF-β1 to TβRII on endothelial cells leading to decreased signaling. Since circulating TGF-β1 is complexed with latency associated peptide and latent TGF-β1 binding protein, it cannot bind its receptors, unless activated. It is therefore likely that soluble endoglin only inhibits TGF-β1 effects locally where active TGF-β1 is generated. Taken together, these data suggest a crucial role for endoglin in linking TGF-β receptor activation to nitric oxide (NO) synthesis. In addition, our functional studies suggest that soluble endoglin and sFlt1 act in concert to induce vascular damage and HELLP syndrome by interfering with TGF-β1 and VEGF signaling respectively, likely via inhibition of the downstream activation of NOS.

In the present invention, compounds that bind to or neutralize soluble endoglin are used to reduce the elevated levels of soluble endoglin and to treat pregnancy complications associated with hypertension, including pre-eclampsia or eclampsia. For example, antibodies directed to soluble endoglin as well as RNA interference and antisense nucleobase oligomers directed to lowering the levels of biologically active soluble endoglin are also provided. The invention also features the use of any compound (e.g., polypeptide, small molecule, antibody, nucleic acid, and mimetic) that decreases soluble endolin levels or biological activity or that increases the level or biological activity of TGF-β, NOS, and prostacyclin ($PGI_2$) either alone or in combination with each other or with any compound that decreases the level of sFlt-1 or increases the level or activity of VEGF or PlGF (see for example, U.S. Patent Application Publication Numbers 20040126828, 20050025762, and 20050170444 and PCT Publication Numbers WO 2004/008946 and WO 2005/077007) to treat or prevent pregnancy related hypertensive disorders, such as pre-eclampsia or eclampsia in a subject. The invention also features methods for measuring levels of soluble endoglin, either alone or in combination with sFlt-1, VEGF, PlGF, TGF-β, eNOS, or $PGI_2$, as a detection tool for early diagnosis and management of a pregnancy related hypertensive disorder, including pre-eclampsia and eclampsia.

Accordingly, in a first aspect, the invention features a method of treating or preventing a pregnancy related hypertensive disorder in a subject, that includes administering to the subject (i) a compound capable of decreasing soluble endoglin expression levels or biological activity and (ii) a compound capable of decreasing sFlt-1 expression levels or biological activity, for a time and in an amount sufficient to treat or prevent the pregnancy related hypertensive disorder. Pregnancy related hypertensive disorder include, for example, pre-eclampsia, eclampsia, gestational hypertension, chronic hypertension, HELLP syndrome, and pregnancy with a small for gestational age (SGA) infant. Preferably, the pregnancy related hypertensive disorder is pre-eclampsia or eclampsia.

Assays for soluble endoglin or sFlt-1 expression levels or biological activity are known in the art. Preferred compounds will decrease soluble endoglin or sFlt-1 expression levels or biological activity by at least 10%, 20%, 30%, 40%, 50%, 60%, 70%, 80%, 90%, or more. Non-limiting examples of compounds capable of decreasing soluble endoglin expression levels or biological activity include any compound that specifically binds soluble endoglin, for example, a purified soluble endoglin antibody, a soluble endoglin antigen-binding fragment, or a growth factor (e.g., TGF-β1, TGF-β3, activin A, Bone Morphogenic Protein (BMP)-2 and BMP-7).

Additional examples of a compound capable of decreasing soluble endoglin expression levels or biological activity include any compound that inhibits a proteolytic enzyme (e.g., a matrix metalloproteinase (MMP), cathepsin, and elastase) or a compound that increases the level of a growth factor capable of binding to soluble endoglin. Growth factors such as TGF-β1, TGF-β3, activin A, BMP-2, BMP-7, or fragments thereof, are examples of compounds that increases the level of a growth factor capable of binding to soluble endoglin as are cyclosporine, alpha tocopherol, methysergide, bromocriptine, and aldomet.

Non-limiting examples of a compound capable of decreasing sFlt-1 expression levels or biological activity include a compound capable of specifically binding to sFlt-1, such as a purified sFlt-1 antibody or an sFlt-1 antigen-binding fragment; compounds that increase the level of a growth factor capable of binding to sFlt-1, such as nicotine, theophylline, adenosine, nifedipine, minoxidil, and magnesium sulfate, VEGF (e.g., VEGF121, VEGF165, or a modified form of VEGF), PlGF, or fragments thereof.

In preferred embodiments of the above method, a compound capable of decreasing soluble endoglin expression levels or biological activity or a compound capable of decreasing sFlt-1 expression levels or biological activity, or both, can also increase nitric oxide synthase (NOS) activity by at least 10%, 20%, 30%, 40%, 50%, 60%, 70%, 80%, 90%, or more. Assays for NOS activity are known in the art and described herein.

In a second aspect, the invention features a method of treating or preventing a pregnancy related hypertensive disorder in a subject, that includes the step of administering to the subject a compound capable of increasing the expression level or biological activity of NOS, for a time and in an amount sufficient to treat or prevent the pregnancy related hypertensive disorder in the subject. Desirably, the NOS is eNOS. In one embodiment, the compound is a compound that increases the phosphorylation of Ser 1177 of eNOS, such as VEGF (e.g., VEGF121, VEGF165, or a modified form of VEGF), or biologically active fragments thereof, or PlGF or biologically active fragments thereof. In another embodiment, the compound is a compound that increases the dephosphorylation of Thr495 of eNOS, such as TGF-β1 or TGF-β3, activin A, BMP-2, and BMP-7. In another embodiment, the compound is a compound that prevents a reduction in the levels of eNOS or increases the stability of eNOS.

Optionally, the method further includes administering to the subject a compound capable of reducing soluble endoglin expression or biological activity, wherein the administering is sufficient to treat or prevent the pregnancy related hypertensive disorder in the subject. Non-limiting examples of a compound capable of reducing soluble endoglin expression or biological activity include a purified antibody that specifically binds soluble endoglin or a soluble endoglin antigen-binding fragment or a compound that inhibits a proteolytic enzyme selected from the group consisting of a matrix metalloproteinase (MMP), cathepsin, and elastase, or growth factors such as TGF-β1, TGF-β3, activin A, BMP-2, BMP-7, or fragments thereof.

Optionally, the method further includes administering to the subject a compound capable of reducing sFlt-1 expression or biological activity, wherein the administering is sufficient to treat or prevent the pregnancy related hypertensive disorder in the subject. Non-limiting examples of a compound capable of reducing soluble endoglin expression or biological activity include a purified antibody that specifically binds sFlt-1 or a sFlt-1 antigen binding fragment, or a growth factor such as VEGF (e.g., VEGF121, VEGF165, or a modified form of VEGF), PlGF, or fragments thereof.

For any of the above methods, the method can further include the step of administering to a subject an anti-hypertensive compound. In preferred embodiments of any of the above methods, the subject is a pregnant human, a post-partum human, or a non-human (e.g., a cow, a horse, a sheep, a pig, a goat, a dog, and a cat).

As described below, we have discovered that deregulation of both the soluble endoglin/TGF-β and the sFlt-1/VEGF/PlGF signaling pathways can act together to further the pathology of the pregnancy related hypertensive disorder. Therefore, the invention also features combinations of the methods described herein with any of the therapeutic, diagnostic, or monitoring methods described in U.S. Patent Application Publication Numbers 20040126828, 20050025762, 20050170444, and 2006/0067937 and PCT Publication Numbers WO 2004/008946, WO 2005/077007, and WO 06/034507.

For the purpose of the present invention, the following abbreviations and terms are defined below.

By "alteration" is meant a change (increase or decrease). An alteration can include a change in the expression levels of a gene or polypeptide as detected by standard art known methods such as those described below. As used herein, an alteration includes a 10% change in expression levels, preferably a 25% change, more preferably a 40%, 50%, 60%, 70%, 80%, 90% or greater change in expression levels. "Alteration" can also indicate a change (increase or decrease) in the biological activity of any of the polypeptides of the invention (e.g., soluble endoglin, sFlt-1, VEGF, PlGF, eNOS, or TGFβ family member). As used herein, an alteration includes a 10% change in biological activity, preferably a 25% change, more preferably a 40%, 50%, 60%, 70%, 80%, 90% or greater change in biological activity. Examples of biological activity for soluble endoglin are angiogenesis and binding to substrates such as activin-A, BMP 2, BMP-7, TGF-β1 and TGF-β3. The biological activity of soluble endoglin can be measured by ligand binding assays, immunoassays, and angiogenesis assays that are standard in the art or are described herein. An example of such an assay is the in vitro matrigel endothelial tube formation assay in which antagonism of endoglin signaling led to massive loss of capillary formation (Li et al., *Faseb Journal* 14:55-64 (2000)). Examples of biological activity for eNOS include catalyzing the formation of nitric oxide or "NO" from oxygen and arginine. Examples of biological activity for TGF-β include regulation of growth, differentiation, motility, tissue remodeling, neurogenesis, wound repair, apoptosis, and angiogenesis in many cell types. Such activities can be measured by assays known in the art or described herein. TGF-β also inhibits cell proliferation in many cell types and can stimulate the synthesis of matrix proteins. Other examples of biological activity for PlGF or VEGF include binding to receptors as measured by immunoassays, ligand binding assays or Scatchard plot analysis, and induction of cell proliferation or migration as measured by BrdU labeling, cell counting experiments, or quantitative assays for DNA synthesis such as $^3$H-thymidine incorporation. Examples of biological activity for sFlt-1 include binding to PlGF and VEGF as measured by immunoassays, ligand binding assays, or Scatchard plot analysis. Additional examples of assays for biological activity for each of the polypeptides are described herein.

By "antisense nucleobase oligomer" is meant a nucleobase oligomer, regardless of length, that is complementary to the coding strand or mRNA of an endoglin gene. By a "nucleobase oligomer" is meant a compound that includes a chain of at least eight nucleobases, preferably at least twelve, and most preferably at least sixteen bases, joined together by linkage groups. Included in this definition are natural and non-natural oligonucleotides, both modified and unmodified, as well as oligonucleotide mimetics such as Protein Nucleic Acids, locked nucleic acids, and arabinonucleic acids. Numerous nucleobases and linkage groups may be employed in the nucleobase oligomers of the invention, including those described in U.S. Patent Publication Nos. 20030114412 (see for example paragraphs 27-45 of the publication) and 20030114407 (see for example paragraphs 35-52 of the publication), incorporated herein by reference. The nucleobase oligomer can also be targeted to the translational start and stop sites. Preferably the antisense nucleobase oligomer comprises from about 8 to 30 nucleotides. The antisense nucleobase oligomer can also contain at least 40, 60, 85, 120, or more consecutive nucleotides that are complementary to endoglin mRNA or DNA, and may be as long as the full-length mRNA or gene.

By "binding" is meant a non-covalent or a covalent interaction, preferably non-covalent, that holds two molecules together. For example, two such molecules could be a ligand and its receptor, an enzyme and an inhibitor of that enzyme, an enzyme and its substrate, or an antibody and an antigen. Non-covalent interactions include, but are not limited to, hydrogen bonding, ionic interactions among charged groups, van der Waals interactions, and hydrophobic interactions among non-polar groups. One or more of these interactions can mediate the binding of two molecules to each other. Binding may exhibit discriminatory properties such as specificity or selectivity.

By "body mass index" is meant a number, derived by using height and weight measurements, that gives a general indication of whether or not weight falls within a healthy range. The formula generally used to determine the body mass index is a person's weight in kilograms divided by a person's height in meters squared or weight (kg)/(height (m))$^2$.

By "compound" is meant any small molecule chemical compound (peptidyl or non-peptidyl), antibody, nucleic acid molecule, polypeptide, or fragments thereof. Compounds particularly useful for the therapeutic methods of the invention can alter, preferably decrease, the levels or biological activity of soluble endoglin by at least 10%, 20%, 30%, 40%, 50%, 60%, 70%, 80%, 90% or more.

By "chimeric antibody" is meant a polypeptide comprising at least the antigen-binding portion of an antibody molecule linked to at least part of another protein (typically an immunoglobulin constant domain).

By "double-stranded RNA (dsRNA)" is meant a ribonucleic acid molecule comprised of both a sense and an anti-sense strand. dsRNAs are typically used to mediate RNA interference.

By "endoglin" or "Eng," also known as CD105, is meant a mammalian growth factor that has endoglin biological activity (see Fonsatti et al., *Oncogene* 22:6557-6563, 2003; Fonsatti et al., *Curr. Cancer Drug Targets* 3:427-432, 2003; and Cheifetz et al., *J. Biol. Chem.* 267:19027-19030 (1992)) and is homologous to the protein defined by any of the following GenBank accession numbers: AAH29080 and NP_031958 (mouse); AAS67893 (rat); NP_000109, P17813, VSP_004233, CAA80673 (pig); and CAA50891 and AAC63386 (human), or described in U.S. Pat. No. 6,562,957. Endoglin is a homodimeric cell membrane glycoprotein which is expressed at high levels in proliferating vascular endothelial cells and in the syncytiotrophoblasts from placentas. There are two distinct isoforms of endoglin, L and S, which differ in their cytoplasmic tails by 47 amino acids. Both isoforms are included in the term endoglin as used herein. Endoglin binds to TGF-β family members and, in the presence of TGF-β, endoglin can associate with the TGF-β signaling receptors RI and RII, and potentiate the response to the growth factors. Endoglin biological activities include binding to TGF-β family members such as activin-A, BMP 2, BMP-7, TGF-β1 and TGF-β3; induction of angiogenesis, regulation of cell proliferation, attachment, migration, invasion; and activation of endothelial cells. Assays for endoglin biological activities are known in the art and include ligand binding assays or Scatchard plot analysis; BrdU labeling, cell counting experiments, or quantitative assays for DNA synthesis such as $^3$H-thymidine incorporation used to measure cell proliferation; and angiogenesis assays such as those described herein or in McCarty et al., *Intl. J. Oncol.* 21:5-10, 2002; Akhtar et al. *Clin. Chem.* 49:32-40, 2003; and Yamashita et al, *J. Biol. Chem.* 269:1995-2001, 1994).

By "soluble endoglin polypeptide" or "sEng" is meant any circulating, non-membrane bound form of endoglin which includes at least a part of the extracellular portion of the endoglin protein and is substantially identical (e.g., 60%, 70%, 80%, 90%, 995%, 96%, 97%, 98%, 99%, or 100%) to the amino acid sequence encoding the extracellular portion of the endoglin protein (see FIGS. 1 and 2B). Soluble endoglin can result from the cleavage of the membrane bound form of endoglin by a proteolytic enzyme. One potential cleavage site is at amino acid 437 of human endoglin producing a soluble endoglin polypeptide that includes amino acids 1-437 of the endoglin polypeptide, including the peptide leader sequence, which is typically cleaved off in the ER (see FIGS. 3A and 3B), or a protein that is substantially identical to amino acids 1-437 of the endoglin polypeptide. Additional forms of soluble endoglin contemplated by the invention include a protein substantially identical to amino acids 40 (glycine) to 406 (arginine) of the human endoglin shown in FIG. 30B, substantially identical to amino acids 1 to 587 of human endoglin (the entire extracellular domain, including the peptide leader sequence, commercially available from R&D Systems, catalog number 1097-EN), substantially identical to amino acids 40 to 587 of human endoglin shown in FIG. 30B (this is the entire extracellular domain with the peptide leader sequence excluded), any polypeptide that includes the peptides identified in bold and underlined in FIG. 30B, and any polypeptide that includes the regions or domains of soluble endoglin that are required for binding to TGF-β or TGF-β receptors. It should be noted that the numbering of both endoglin and soluble endoglin depends on whether the leader peptide sequence is included. The numbering of endoglin shown in FIG. 30B, starts at amino acid 26 (where the absent leader peptide sequence would be amino acids 1-25). Soluble endoglin can also include circulating degradation products or fragments that result from enzymatic cleavage of endoglin and that maintain endoglin biological activity. Preferred soluble endoglin polypeptides have soluble endoglin biological activity such as binding to substrates such as TGF-β family members or TGF-β receptors, inhibiting the biological activity of TGF-β family members, or reversing or inhibiting angiogenesis by at least 10%, 20%, 30%, 40%, 50%, 60%, 70%, 80%, 90%, or more. Examples of assays for measuring these activities are known in the art and described in U.S. Patent Application Publication Nos. 2006/0067937 and 20050267021 and PCT Publication No. WO 06/034507, incorporated herein by reference. For example, soluble endoglin biological activity can include the ability to reverse, reduce, or inhibit angiogenesis induced by TGF-β or the ability to reverse activation of Smad 2/3 or Smad 2/3 dependent transcriptional activation. Soluble endoglin polypeptides may be isolated from a variety of sources, such as from mammalian tissue or cells (e.g., placental tissue or cells), or prepared by recombinant or synthetic methods. The term soluble endoglin also encompasses modifications to the polypeptide, fragments, derivatives, analogs, and variants of the endoglin polypeptide, examples of which are described below.

By "endoglin nucleic acid" is meant a nucleic acid that encodes any of the endoglin proteins described above. For example, the gene for human endoglin consists of 14 exons, where exon 1 encodes the signal peptide sequence, exons 2-12 encode the extracellular domain (includes exon 9a and 9b), exon 13 encodes the transmembrane domain, and exon 14 encodes C-terminal cytoplasmic domain (see FIGS. 1, 2A, and 2B). Desirably, the endoglin nucleic acid encodes any of the soluble endoglin polypeptides described above or is substantially identical (60%, 65%, 70%, 75%, 80%, 85%, 90%, 95%, 96%, 97%, 98%, 99%, or 100%) to the nucleic acid sequence set forth in FIG. 2A. It should be noted that the circulating protein is predicted to lack the peptide leader sequence (amino acids 1-25).

By "expression" is meant the detection of a gene or polypeptide by standard art known methods. For example, polypeptide expression is often detected by western blotting, DNA expression is often detected by Southern blotting or polymerase chain reaction (PCR), and RNA expression is often detected by northern blotting, PCR, or RNAse protection assays. Methods to measure protein expression levels generally include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Exemplary assays are described in detail in U.S. Patent Application Publication No. 2006/0067937 and PCT Publication No. WO 06/034507. Any compound that decreases soluble endoglin levels by at least 10%, 20%, preferably 30%, more preferably at least 40% or 50%, and most preferably at least 60%, 70%, 80%, 90% or more is considered a therapeutic compound of the invention.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides or 10, 20, 30, 40, 50, 60, 70, 80, 90, 100, 150, 200, 250, 300, 350, 400, 450, 500, 550, 600, 640 amino acids or more. Exemplary fragments of soluble endoglin include from 1 to 437 amino acids (including the peptide leader sequence), 26 to 437 amino acids (excluding the leader sequence), from 40 to 406 amino acids, or from 1 to 587 amino acids, and from 1 to 1311, 10 to 1311, 80 to 1030, or 1 to 1761 nucleotides.

By "gestational age" is meant a reference to the age of the fetus, counting from the first day of the mother's last menstrual period usually referred to in weeks.

By "gestational hypertension" is meant the development of high blood pressure without proteinuria after 20 weeks of pregnancy.

By a "history of pre-eclampsia or eclampsia" is meant a previous diagnosis of pre-eclampsia or eclampsia or pregnancy induced hypertension in the subject themselves or in a related family member.

By "homologous" is meant any gene or protein sequence that bears at least 30% homology, more preferably 40%, 50%, 60%, 70%, 80%, and most preferably 90% or more homology to a known gene or protein sequence over the length of the comparison sequence. A "homologous" protein can also have at least one biological activity of the comparison protein. In general, for proteins, the length of comparison sequences will be at least 10 amino acids, preferably 20, 30, 40, 50, 60, 70, 80, 90, 100, 110, 120, 130, 140, 150, 200, 250, 300, 350, 400, 437, or at least 587 amino acids or more. For nucleic acids, the length of comparison sequences will generally be at least 25, 50, 100, 125, 150, 200, 250, 300, 350, 400, 450, 500, 550, 600, 650, 700, 800, 900, 1000, 1100, 1200, 1311, or at least 1761 nucleotides or more. "Homology" can also refer to a substantial similarity between an epitope used to generate antibodies and the protein or fragment thereof to which the antibodies are directed. In this case, homology refers to a similarity sufficient to elicit the production of antibodies that can specifically recognize the protein at issue.

By "humanized antibody" is meant an immunoglobulin amino acid sequence variant or fragment thereof that is capable of binding to a predetermined antigen. Ordinarily, the antibody will contain both the light chain as well as at least the variable domain of a heavy chain. The antibody also may include the CH1, hinge, CH2, CH3, or CH4 regions of the heavy chain. The humanized antibody comprises a framework region (FR) having substantially the amino acid sequence of a human immunoglobulin and a complementarity determining region (CDR) having substantially the amino acid sequence of a non-human immunoglobulin (the "import" sequences).

Generally, a humanized antibody has one or more amino acid residues introduced into it from a source that is non-human. In general, the humanized antibody will comprise substantially all of at least one, and typically two, variable domains (Fab, Fab', F(ab')$_2$, Fabc, Fv) in which all or substantially all of the CDR regions correspond to those of a non-human immunoglobulin and all or substantially all of the FR regions are those of a human immunoglobulin consensus sequence. The humanized antibody optimally will comprise at least a portion of an immunoglobulin constant region (Fc), typically that of a human immunoglobulin. By "complementarity determining region (CDR)" is meant the three hypervariable sequences in the variable regions within each of the immunoglobulin light and heavy chains. By "framework region (FR)" is meant the sequences of amino acids located on either side of the three hypervariable sequences (CDR) of the immunoglobulin light and heavy chains.

The FR and CDR regions of the humanized antibody need not correspond precisely to the parental sequences, e.g., the import CDR or the consensus FR may be mutagenized by substitution, insertion or deletion of at least one residue so that the CDR or FR residue at that site does not correspond to either the consensus or the import antibody. Such mutations, however, will not be extensive. Usually, at least 75%, preferably 90%, and most preferably at least 95% of the humanized antibody residues will correspond to those of the parental FR and CDR sequences.

By "hybridize" is meant pair to form a double-stranded molecule between complementary polynucleotide sequences, or portions thereof, under various conditions of stringency. (See, e.g., Wahl and Berger *Methods Enzymol.* 152:399, 1987; Kimmel, *Methods Enzymol.* 152:507, 1987.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196:180, 1977); Grunstein and Hogness (*Proc. Natl. Acad. Sci., USA* 72:3961, 1975); Ausubel et al. (*Current Protocols in Molecular Biology*, Wiley Interscience, New York, 2001); Berger and Kimmel (*Guide to Molecular Cloning Techniques*, 1987, Academic Press, New York); and Sambrook et al., *Molecular Cloning: A Laboratory Manual*, Cold Spring Harbor Laboratory Press, New York.

By "intrauterine growth retardation (IUGR)" is meant a syndrome resulting in a birth weight which is less that 10 percent of the predicted fetal weight for the gestational age of the fetus. The current World Health Organization criterion for low birth weight is a weight less than 2,500 gm (5 lbs. 8 oz.) or below the 10$^{th}$ percentile for gestational age according to U.S. tables of birth weight for gestational age by race, parity, and infant sex (Zhang and Bowes, *Obstet. Gynecol.* 86:200-208, 1995). These low birth weight babies are also referred to as "small for gestational age (SGA)". Pre-eclampsia is a condition known to be associated with IUGR or SGA.

By "metric" is meant a measure. A metric may be used, for example, to compare the levels of a polypeptide or nucleic acid molecule of interest. Exemplary metrics include, but are not limited to, mathematical formulas or algorithms, such as ratios. The metric to be used is that which best discriminates between levels of soluble endoglin, sFlt-1, VEGF, PlGF, or any combination thereof, in a subject having pregnancy related hypertensive disorder, such as pre-eclampsia or eclampsia, and a normal control subject. Depending on the metric that is used the diagnostic indicator of pregnancy related hypertensive disorder may be significantly above or below a reference value (e.g., from a control subject not having a pregnancy related hypertensive disorder). Soluble endoglin level is determined by measuring the amount of free, bound (i.e., bound to growth factor), or total (free+bound) soluble endoglin. sFlt-1 level is measured by measuring the amount of free, bound (i.e., bound to growth factor), or total sFlt-1 (bound+free). VEGF or PlGF levels are determined by measuring the amount of free PlGF or free VEGF (i.e., not bound to sFlt-1). One exemplary metric is [sFlt-1/(VEGF+PlGF)], also referred to as the pre-eclampsia anti-angiogenic index (PAAI). Another example is the following soluble endoglin anti-angiogenic index: (sFlt-1+0.25(soluble endoglin polypeptide))/PlGF. An increase in the value of the soluble endoglin anti-angiogenic index is a diagnostic indicator of pre-eclampsia or eclampsia. Yet another exemplary metric is the following: (soluble enodglin+sFlt-1)/PlGF. Any of the metrics of the invention can further include the BMI of the mother or GA of the infant. Any of the metrics can also include eNOS, TGF-β1 or β3 or PGI$_2$ levels as well.

By "nitric oxide synthase" or "NOS" is meant an enzyme that catalyzes the formation of nitric oxide (NO) from oxygen and arginine. NOS is a complex enzyme containing several cofactors, a heme group which is part of the catalytic site, an N-terminal oxygenase domain, which belongs to the class of haem-thiolate proteins, and a C-terminal reductase domain which is homologous to NADPH:P450 reductase. NOS produces NO by catalysing a five-electron oxidation of a guanidino nitrogen of L-arginine (L-Arg). Oxidation of L-Arg to L-citrulline occurs via two successive monooxygenation reactions producing N-hydroxy-L-arginine as an intermediate. The interdomain linker between the oxygenase and reductase domains contains a CaM-binding sequence. NO functions at low concentrations as a signal in many diverse physiological processes such as blood pressure control, neurotransmission, learning and memory, and at high concentrations as a defensive cytotoxin.

In mammals, three distinct genes encode NOS isozymes: neuronal (nNOS or NOS-1), cytokine-inducible (iNOS or NOS-2) and endothelial (eNOS or NOS-3). eNOS is membrane associated and eNOS localization to endothelial membranes is mediated by cotranslational N-terminal myristoylation and post-translational palmitoylation. In preferred embodiments of the invention, the NOS is eNOS.

By "pre-eclampsia anti-angiogenesis index (PAAI)" is meant the ratio of sFlt-1/VEGF+PlGF used as an indicator of anti-angiogenic activity. A PAAI greater than 10, more preferably greater than 20, is indicative of a pregnancy related hypertensive disorder, such as pre-eclampsia or risk of pre-eclampsia.

By "soluble endoglin anti-angiogenic index" is meant the ratio of (sFlt-1+0.25 soluble endoglin)/PlGF. For example, a value of 75, or higher, preferably 100 or higher, or more preferably 200 or higher is indicative of a pregnancy complication associated with hypertension, such as pre-eclampsia or eclampsia.

By "operably linked" is meant that a gene and a regulatory sequence(s) are connected in such a way as to permit gene expression when the appropriate molecules (e.g., transcriptional activator proteins) are bound to the regulatory sequence(s).

By "pharmaceutically acceptable carrier" is meant a carrier that is physiologically acceptable to the treated mammal while retaining the therapeutic properties of the compound with which it is administered. One exemplary pharmaceutically acceptable carrier substance is physiological saline. Other physiologically acceptable carriers and their formulations are known to one skilled in the art and described, for example, in Remington's Pharmaceutical Sciences, (20$^{th}$ edition), ed. A. Gennaro, 2000, Lippincott, Williams & Wilkins, Philadelphia, Pa.

By "placental growth factor (PlGF)" is meant a mammalian growth factor that is homologous to the protein defined by GenBank accession number P49763 and that has PlGF biological activity. PlGF is a glycosylated homodimer belonging to the VEGF family and can be found in two distinct isoforms through alternative splicing mechanisms. PlGF is expressed by cyto- and syncytiotrophoblasts in the placenta and PlGF biological activities include induction of proliferation, migration, and activation of endothelial cells, particularly trophoblast cells.

By "polymorphism" is meant a genetic variation, mutation, deletion or addition in a soluble endoglin, sFlt-1, PlGF, or VEGF nucleic acid molecule that is indicative of a predisposition to develop pre-eclampsia or eclampsia. Such polymorphisms are known to the skilled artisan and are described, for example, by Raab et al. (*Biochem. J.* 339:579-588, 1999) and Parry et al. (*Eur. J. Immunogenet.* 26:321-323, 1999). A polymorphism may be present in the promoter sequence, an open reading frame, intronic sequence, or untranslated 3' region of a gene. Known examples of such polymorphisms in the endoglin gene include a 6 base insertion of GGGGGA in intron 7 at 26 bases beyond the 3' end of exon 7 (*Ann. Neurol.* 41:683-6, 1997).

By "pregnancy related hypertensive disorder" is meant any condition or disease or pregnancy that is associated with or characterized by an increase in blood pressure. Included among these conditions are pre-eclampsia (including premature pre-eclampsia, severe pre-eclampsia), eclampsia, gestational hypertension, HELLP syndrome, (hemolysis, elevated liver enzymes, low platelets), abruption placenta, chronic hypertension, pregnancy with intra uterine growth restriction, and pregnancy with a small for gestational age (SGA) infant. It should be noted that although pregnancy with a SGA infant is not often associated with hypertension, it is included in this definition.

By "pre-eclampsia" is meant the multi-system disorder that is characterized by hypertension with proteinuria or edema, or both, glomerular dysfunction, brain edema, liver edema, or coagulation abnormalities due to pregnancy or the influence of a recent pregnancy. All forms of pre-eclampsia, such as premature, mild, moderate, and severe pre-eclampsia are included in this definition. Pre-eclampsia generally occurs after the 20$^{th}$ week of gestation. Pre-eclampsia is generally defined as some combination of the following symptoms: (1) a systolic blood pressure (BP)>140 mmHg and a diastolic BP>90 mmHg after 20 weeks gestation (generally measured on two occasions, 4-168 hours apart), (2) new onset proteinuria (1+ by dipstik on urinalysis, >300 mg of protein in a 24-hour urine collection, or a single random urine sample having a protein/creatinine ratio >0.3), and (3) resolution of hypertension and proteinuria by 12 weeks postpartum. Severe pre-eclampsia is generally defined as (1) a diastolic BP>110 mmHg (generally measured on two occasions, 4-168 hours apart) or (2) proteinuria characterized by a measurement of 3.5 grams or more protein in a 24-hour urine collection or two random urine specimens with at least 3+ protein by dipstick. In pre-eclampsia, hypertension and proteinuria generally occur within seven days of each other. In severe pre-eclampsia, severe hypertension, severe proteinuria and HELLP syndrome (hemolysis, elevated liver enzymes, low platelets) or eclampsia can occur simultaneously or only one symptom at a time. HELLP syndrome is characterized by evidence of thrombocytopenia (<100000 cells/µl), increased LDH (>600 IU/L) and increased AST (>70 IU/L). Occasionally, severe pre-eclampsia can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral edema and cerebral hemorrhage). The etiology of the seizures is thought to be secondary to the development of cerebral edema and focal spasm of small blood vessels in the kidney.

By "premature pre-eclampsia" is meant pre-eclampsia with onset of symptoms <37 weeks or <34 weeks.

By "prostacyclin" or "$PGI_2$" is meant a member of the family of lipid molecules known as eicosanoids. It is produced in endothelial cells from prostaglandin H2 (PGH2) by the action of the enzyme prostacyclin synthase and is mainly synthesized by vascular endothelium and smooth muscle. $PGI_2$ biological activity includes inhibition of platelet aggregation, relaxation of smooth muscle, reduction of systemic and pulmonary vascular resistance by direct vasodilation, and natriuresis in kidney.

By "protein" or "polypeptide" or "polypeptide fragment" is meant any chain of more than two amino acids, regardless of post-translational modification (e.g., glycosylation or phosphorylation), constituting all or part of a naturally occurring polypeptide or peptide, or constituting a non-naturally occurring polypeptide or peptide.

By "reference sample" is meant any sample, standard, or level that is used for comparison purposes. A "normal reference sample" can be a prior sample taken from the same subject, a sample from a pregnant subject not having any pregnancy related hypertensive disorder, such as pre-eclampsia or eclampsia, a sample from a pregnant subject not having a pregnancy related hypertensive disorder, such as pre-eclampsia or eclampsia, a subject that is pregnant but the sample was taken early in pregnancy (e.g., in the first or second trimester or before the detection of a pregnancy related hypertensive disorder, such as pre-eclampsia or eclampsia), a subject that is pregnant and has no history of a pregnancy related hypertensive disorder, such as pre-eclampsia or eclampsia, a subject that is not pregnant, a sample of a purified reference polypeptide at a known normal concentration (i.e., not indicative of a pregnancy related hypertensive disorder, such as pre-eclampsia or eclampsia). By "reference standard or level" is meant a value or number derived from a reference sample. A normal reference standard or level can be a value or number derived from a normal subject that is matched to the sample subject by at least one of the following criteria: gestational age of the fetus, maternal age, maternal blood pressure prior to pregnancy, maternal blood pressure during pregnancy, BMI of the mother, weight of the fetus, prior diagnosis of pre-eclampsia or eclampsia, and a family history of pre-eclampsia or eclampsia. A "positive reference" sample, standard or value is a sample or value or number derived from a subject that is known to have a pregnancy related hypertensive disorder, such as pre-eclampsia or eclampsia, that is matched to the sample subject by at least one of the following criteria: gestational age of the fetus, maternal age, maternal blood pressure prior to pregnancy, maternal blood pressure during pregnancy, BMI of the mother, weight of the fetus, prior diagnosis of a pregnancy related hypertensive disorder, and a family history of a pregnancy related hypertensive disorder By "reduce or inhibit" is meant the ability to cause an overall decrease preferably of 20% or greater, more preferably of 40%, 50%, 60%, 70%, 80%, 90% or greater change in the level of protein or nucleic acid, detected by the aforementioned assays (see "expression"), as compared to an untreated sample By "sample" is meant a tissue biopsy, cell, bodily fluid (e.g., blood, serum, plasma, urine, saliva, amniotic fluid, or cerebrospinal fluid) or other specimen obtained from a subject. Desirably, the biological sample includes soluble endoglin nucleic acid molecules or polypeptides or both.

By "small interfering RNAs (siRNAs)" is meant an isolated dsRNA molecule, preferably greater than 10 nucleotides (nt) in length, more preferably greater than 15 nucleotides in length, and most preferably greater than 19 nucleotides in length that is used to identify the target gene or mRNA to be degraded. A range of 19-25 nucleotides is the most preferred size for siRNAs. siRNAs can also include short hairpin RNAs in which both strands of an siRNA duplex are included within a single RNA molecule. siRNA includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides. Such alterations can include the addition of non-nucleotide material, such as to the end(s) of the 19, 20, 21, 22, 23, 24, or 25 nt RNA or internally (at one or more nucleotides of the RNA). In a preferred embodiment, the RNA molecules contain a 3' hydroxyl group. Nucleotides in the RNA molecules of the present invention can also comprise non-standard nucleotides, including non-naturally occurring nucleotides or deoxyribonucleotides. Collectively, all such altered RNAs are referred to as analogs of RNA. siRNAs of the present invention need only be sufficiently similar to natural RNA that it has the ability to mediate RNA interference (RNAi). As used herein, RNAi refers to the ATP-dependent targeted cleavage and degradation of a specific mRNA molecule through the introduction of small interfering RNAs or dsRNAs into a cell or an organism. As used herein "mediate RNAi" refers to the ability to distinguish or identify which RNAs are to be degraded.

By "soluble endoglin binding molecule" is meant a protein or small molecule compound that specifically binds a soluble endoglin polypeptide. A soluble endoglin binding molecule may be, for example, an antibody, antibody-related peptide, one or more CDR regions of a soluble endoglin binding antibody, or soluble endoglin interacting protein.

By "soluble Flt-1 (sFlt-1)" (also known as sVEGF-R1) is meant the soluble form of the Flt-1 receptor, that is homologous to the protein defined by GenBank accession number U01134, and that has sFlt-1 biological activity. The biological activity of an sFlt-1 polypeptide may be assayed using any standard method, for example, by assaying sFlt-1 binding to VEGF. sFlt-1 lacks the transmembrane domain and the cytoplasmic tyrosine kinase domain of the Flt-1 receptor. sFlt-1 can bind to VEGF and PlGF with high affinity, but it cannot induce proliferation or angiogenesis and is therefore functionally different from the Flt-1 and KDR receptors. sFlt-1 was initially purified from human umbilical endothelial cells and later shown to be produced by trophoblast cells in vivo. As used herein, sFlt-1 includes any sFlt-1 family member or isoform. sFlt-1 can also mean degradation products or fragments that result from enzymatic cleavage of the Flt-1 receptor and that maintain sFlt-1 biological activity. In one example, specific metalloproteinases released from the placenta may cleave the extracellular domain of Flt-1 receptor to release the N-terminal portion of Flt-1 into circulation.

By "specifically binds" is meant a compound or antibody which recognizes and binds a polypeptide of the invention but that does not substantially recognize and bind other molecules in a sample, for example, a biological sample, which naturally includes a polypeptide of the invention. In one example, an antibody that specifically binds soluble endoglin does not bind membrane bound endoglin. In another example, an antibody that specifically binds to soluble endoglin recognizes the extracellular domain of endoglin, particularly a region within amino acids 26 to 437 (excluding the peptide leader sequence), amino acids 40 to 406 of human endoglin (see FIG. 30B), or amino acids 26 to 587 (excluding the peptide leader sequence), that is unique to soluble endoglin but not the full-length endoglin. In another example, an antibody that specifically binds to soluble endoglin recognizes one or more of the amino acid sequences shown in bold and underlined in FIG. 30B.

By "subject" is meant a mammal, including, but not limited to, a human or non-human mammal, such as a cow, a horse, a sheep, a pig, a goat, a dog, or a cat. Included in this definition are pregnant, post-partum, and non-pregnant mammals.

By "substantially identical" is meant a nucleic acid or amino acid sequence that, when optimally aligned, for example using the methods described below, share at least 60%, 65%, 70%, 75%, 80%, 85%, 90%, 95%, 96%, 97%, 98%, 99%, or 100% sequence identity with a second nucleic acid or amino acid sequence, e.g., an endoglin or soluble endoglin sequence. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) *J Mol Biol* 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences will be at least 10 amino acids, preferably 20, 30, 40, 50, 60, 70, 80, 90, 100, 110, 120, 130, 140, 150, 200, 250, 300, 350, 400, 437, or at least 587 amino acids or more. For nucleic acids, the length of comparison sequences will generally be at least 25, 50, 100, 125, 150, 200, 250, 300, 350, 400, 450, 500, 550, 600, 650, 700, 800, 900, 1000, 1100, 1200, 1311, or at least 1761 nucleotides or more. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "symptoms of pre-eclampsia" is meant any of the following: (1) a systolic blood pressure (BP)>140 mmHg and a diastolic BP>90 mmHg after 20 weeks gestation, (2) new onset proteinuria (1+ by dipstik on urinanaysis, >300 mg of protein in a 24 hour urine collection, or random urine protein/creatinine ratio >0.3), and (3) resolution of hypertension and proteinuria by 12 weeks postpartum. The symptoms of pre-eclampsia can also include renal dysfunction and glomerular endotheliosis or hypertrophy. By "symptoms of eclampsia" is meant the development of any of the following symptoms due to pregnancy or the influence of a recent pregnancy: seizures, coma, thrombocytopenia, liver edema, pulmonary edema, and cerebral edema.

By "transforming growth factor β (TGF-β)" is meant a mammalian growth factor that has TGF-β biological activity and is a member of a family of structurally related paracrine polypeptides found ubiquitously in vertebrates, and prototypic of a large family of metazoan growth, differentiation, and morphogenesis factors (see, for review, Massaque et al. *Ann. Rev. Cell. Biol.* 6:597-641 (1990); Massaque et al. *Trends Cell Biol* 4:172-178 (1994); Kingsley *Gene Dev.* 8:133-146 (1994); and Sporn et al. *J. Cell. Biol.* 119:1017-1021 (1992). As described in Kingsley, supra, the TGF-β superfamily has at least 25 members, and can be grouped into distinct sub-families with highly related sequences. The most obvious sub-families include the following: the TGF-β sub-family, which comprises at least four genes that are much more similar to TGF-β1 than to other members of the TGF-β superfamily; the activin sub-family, comprising homo- or hetero-dimers or two sub-units, inhibinβ-A and inhibinβ-B. The decapentaplegic sub-family, which includes the mammalian factors BMP2 and BMP4, which can induce the formation of ectopic bone and cartilage when implanted under the skin or into muscles. The 60A sub-family, which includes a number of mammalian homologs, with osteoinductive activity, including BMP5-8. Other members of the TGF-β superfamily include the gross differentiation factor 1 (GDF-1), GDF-3/VGR-2, dorsalin, nodal, mullerian-inhibiting substance (MIS), and glial-derived neurotrophic growth factor (GDNF). It is noted that the DPP and 60A sub-families are related more closely to one another than to other members of the TGF-β superfamily, and have often been grouped together as part of a larger collection of molecules called DVR (dpp and vg1 related). Unless evidenced from the context in which it is used, the term TGF-β as used throughout this specification will be understood to generally refer to members of the TGF-β superfamily as appropriate. (Massague et al, *Annu. Rev. Biochem.* 67:753-91, 1998; Josso et al, *Curr. Op. Gen. Dev.*, 7:371-377, 1997). TGF-β functions to regulate growth, differentiation, motility, tissue remodeling, neurogenesis, would repair, apoptosis, and angiogenesis in many cell types. TGF-β also inhibits cell proliferation in many cell types and can stimulate the synthesis of matrix proteins.

By "therapeutic amount" is meant an amount that when administered to a patient suffering from pre-eclampsia or eclampsia is sufficient to cause a qualitative or quantitative reduction in the symptoms of pre-eclampsia or eclampsia as described herein. A "therapeutic amount" can also mean an amount that when administered to a patient suffering from pre-eclampsia or eclampsia is sufficient to cause a reduction in the expression levels of soluble endoglin or sFlt-1 or an increase in the expression levels of VEGF or PlGF as measured by the assays described herein.

By "treating" is meant administering a compound or a pharmaceutical composition for therapeutic purposes. To "treat disease" or use for "therapeutic treatment" refers to administering treatment to a subject already suffering from a disease to improve the subject's condition. Preferably, the subject is diagnosed as suffering from a pregnancy complication associated with hypertension, such as pre-eclampsia or eclampsia, based on identification of any of the characteristic symptoms described below or the use of the diagnostic methods described herein. To "prevent disease" refers to prophylactic treatment of a subject who is not yet ill, but who is susceptible to, or otherwise at risk of, developing a particular disease. Preferably a subject is determined to be at risk of developing pre-eclampsia or eclampsia using the diagnostic methods described herein. Thus, in the claims and embodiments, treating is the administration to a mammal either for therapeutic or prophylactic purposes.

By "trophoblast" is meant the mesectodermal cell layer covering the blastocyst that erodes the uterine mucosa and through which the embryo receives nourishment from the mother; the cells contribute to the formation of the placenta.

By "vascular endothelial growth factor (VEGF)" is meant a mammalian growth factor that is homologous to the growth factor defined in U.S. Pat. Nos. 5,332,671; 5,240,848; 5,194,596; and Charnock-Jones et al. (*Biol. Reproduction,* 48: 1120-1128, 1993), and has VEGF biological activity. VEGF exists as a glycosylated homodimer and includes at least four different alternatively spliced isoforms. The biological activity of native VEGF includes the promotion of selective growth of vascular endothelial cells or umbilical vein endothelial cells and induction of angiogenesis. As used herein, VEGF includes any VEGF family member or isoform (e.g., VEGF-A, VEGF-B, VEGF-C, VEGF-D, VEGF-E, VEGF189, VEGF165, or VEGF 121). Preferably, VEGF is the VEGF121 or VEGF165 isoform (Tischer et al., *J. Biol. Chem.* 266, 11947-11954, 1991; Neufed et al. *Cancer Metastasis* 15:153-158, 1996), which is described in U.S. Pat. Nos. 6,447,768; 5,219,739; and 5,194,596, hereby incorporated by reference. Also included are mutant forms of VEGF such as the KDR-selective VEGF and Flt-selective VEGF described in Gille et al. (*J. Biol. Chem.* 276:3222-3230, 2001). As used herein VEGF also includes any modified forms of VEGF such as those described in LeCouter et al. (*Science* 299:890-893, 2003). Although human VEGF is preferred, the invention is not limited to human forms and can include other animal forms of VEGF (e.g. mouse, rat, dog, or chicken).

By "vector" is meant a DNA molecule, usually derived from a plasmid or bacteriophage, into which fragments of DNA may be inserted or cloned. A recombinant vector will contain one or more unique restriction sites, and may be capable of autonomous replication in a defined host or vehicle organism such that the cloned sequence is reproducible. A vector contains a promoter operably linked to a gene or coding region such that, upon transfection into a recipient cell, an RNA is expressed.

Other features and advantages of the invention will be apparent from the following description of the preferred embodiments thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows the predicted cDNA sequence (SEQ ID NO: 1) of soluble endoglin. FIG. 2B shows the predicted amino acid sequence (SEQ ID NO: 2) of soluble endoglin which includes the signal peptide (amino acids 1-25). It should be noted that the sequence includes the leader peptide sequence that would normally be cleaved in the ER.

FIG. 27A shows the renal histology for the control group with no evidence of glomerular endotheliosis. FIG. 27B shows the renal histology for the soluble endoglin injected group with no evidence of glomerular endotheliosis. FIG. 27C shows the renal histology for sFlt1 injected rats showing moderate endotheliosis (shown by arrow head). FIG. 27D shows the renal histology for the soluble endoglin and sFlt1 injected rats showing extremely swollen glomeruli and severe glomerular endotheliosis with protein resorption droplets in the podocytes. All light micrographs were taken at 60× (original magnification).

FIG. 30B shows the sequence of human endoglin (SEQ ID NO: 5). Peptides identified by mass spec are shown in bold and underlined. The underlined amino acids represent the transmembrane domain of human cell surface endoglin. Note that the amino acid sequence numbering starts at 26 because amino acids 1-25 represents the leader peptide. Note that the sequence listed as SEQ ID NO: 5 in the sequence listing begins at amino acid 1 so that amino acid 26 in the figure is amino acid 1 in the sequence listing, amino acid 658 in the figure is amino acid 633 in the sequence listing. The numbering of the amino acids is adjusted depending on the reference sequence (i.e., amino acids 26 to 658 for sequences referring to FIG. 30B are the same as amino acids 1 to 633 for sequences referring to SEQ ID NO: 5).

FIG. 31 shows a series of photomicrographs showing soluble endoglin inhibits capillary formation and increases vascular permeability. Angiogenesis assays were performed using HUVEC in growth factor reduced Matrigel™ in the presence of 1 µg of recombinant soluble endoglin, sFlt1, or both, and endothelial tube lengths were quantified. A representative experiment (n=4) is shown with tube lengths in pixels indicated below the panels.

FIGS. 35A-D are a series of graphs and autoradiograms showing recombinant sEng attenuates TGF-β1 binding and activity and its effects on vasodilation via eNOS activation. FIG. 35A is a graph showing the microvascular responses of renal microvessels to 1 ng/ml of VEGF, TGF-β1 and the combination. The effects of 100 ng/ml each of sFlt1 and sEng on the combined response are shown. (n=4). Also shown is the blocking effect of L-NAME on TGF-β1 and VEGF stimulated responses. FIG. 35B is a representative autoradiogram and graph of a dose-dependent increase in [$I^{125}$] TGF-β1 binding to TβRII on mouse endothelial cells. Treatment with 5 nM recombinant soluble endoglin significantly reduced binding at 50 pM and 100 pM (*P<0.05 vs. untreated group). Competition with 40× excess cold TGF-β1 in cells treated with 100 pM [$I^{125}$] TGF-β1 abolished receptor binding and served as background control. FIG. 35C is a graph showing significantly increased TGF-β-induced activation of the Smad 2/3-dependent CAGA-Luc reporter construct transfected in HUVECs and inhibition by treatment with sEng. (n=3, **P<0.01 vs. sEng untreated group). FIG. 35D is a representative western blots and graph (n=4) showing significant dephosphorylation at eNOS Thr495 following treatment with TGF-β1 and attenuation by sEng (*P<0.05 vs. untreated). Phosphorylation was unchanged at Ser1177 and total levels of eNOS remained constant throughout the experiments.

DETAILED DESCRIPTION

Figure 1:
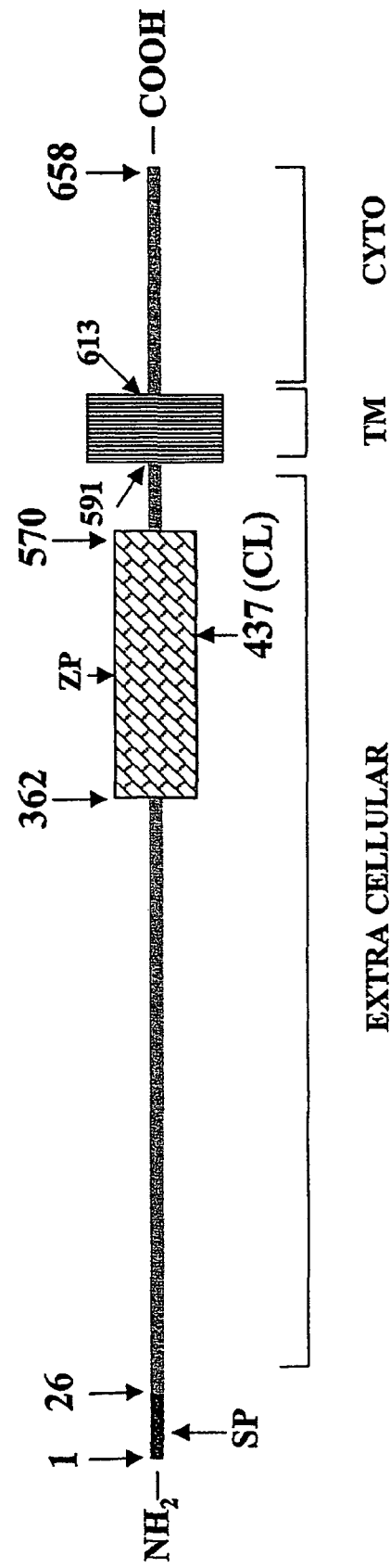
FIG. 1 is a schematic showing the endoglin protein. SP: signal peptide (also referred to as the peptide leader sequence), ZP: zona pellucida domain, CL: potential cleavage site (amino acid 437) for the release of soluble endoglin, TM: transmembrane domain, Cyto: cytoplasmic domain. Once the signal peptide is cleaved, the remaining mature protein starts at the glutamic acid residue at amino acid 26.

We have discovered that soluble endoglin levels are elevated in blood serum samples taken from women with a pregnancy related hypertensive disorder, such as pre-eclampsia or eclampsia. Soluble endoglin may be formed by cleavage of the extracellular portion of the membrane bound form by proteolytic enzymes. The lack of detection of alternate splice variants in placenta and the partial peptide sequence of purified soluble endoglin as described herein suggest that it is an N-terminal cleavage product of full-length endoglin. Excess soluble endoglin may be depleting the placenta of necessary amounts of these essential angiogenic and mitogenic factors. We have discovered that excess circulating concentrations of soluble endoglin and sFlt1 in patients with preeclampsia contribute to the pathogenesis of pre-eclampsia and other pregnancy related hypertensive disorder. We have also discovered that soluble endoglin interferes with TGF-β1 and TGF-β3 binding to its receptor leading to decreased signaling such as a reduction in eNOS activation in endothelial cells, thereby disrupting key homeostatic mechanisms necessary for maintenance of vascular health. These data suggest a crucial role for endoglin in linking TGF-β receptor activation to NO synthesis. In addition, we have discovered that soluble endoglin and sFlt1 act in concert to induce vascular damage and pregnancy related hypertensive disorders, such as pre-eclampsia or eclampisa, by interfering with TGF-β1 and VEGF signaling respectively, likely via inhibition of the downstream activation of eNOS.

The present invention features the use of therapeutic agents that interfere with soluble endoglin binding to growth factors, agents that reduce soluble endoglin expression or biological activity, or agents that increase levels of growth factors, can be used to treat or prevent pregnancy related hypertensive disorders, such as pre-eclampsia or eclampsia in a subject. Such agents include, but are not limited to, antibodies to soluble endoglin, oligonucleotides for antisense or RNAi that reduce levels of soluble endoglin, compounds that increase the levels of growth factors, compounds that prevent the proteolytic cleavage of the membrane bound form of endoglin thereby preventing the release of soluble endoglin, and small molecules that bind soluble endoglin and block the growth factor binding site. Additionally or alternatively, the invention features the use of any compound (e.g., polypeptide, small molecule, antibody, nucleic acid, and mimetic) that increases the level or biological activity of TGF-β, eNOS, and PGI$_2$ to treat or prevent pregnancy related hypertensive disorders, such as pre-eclampsia or eclampsia in a subject. Additionally, the invention features the use of any compound that decreases the level of sFlt-1 or increases the level or activity of VEGF or PlGF (see for example, U.S. Patent Application Publication Numbers 20040126828, 20050025762, and 20050170444 and PCT Publication Numbers WO 2004/008946 and WO 2005/077007) in combination with any of the therapeutic compounds described above to treat or prevent pregnancy related hypertensive disorders, such as pre-eclampsia or eclampsia in a subject. In addition, the invention features the use of soluble endoglin, eNOS, TGF-β, of PGI$_2$, either alone or in combination, as a diagnostic marker of pregnancy related hypertensive disorders, including pre-eclampsia and eclampsia.

While the detailed description presented herein refers specifically to soluble endoglin, TGF-β1, eNOS, sFlt-1, VEGF, or PlGF, it will be clear to one skilled in the art that the detailed description can also apply to family members, isoforms, and/or variants of soluble endoglin, TGF-β, eNOS, sFlt-1, VEGF, or PlGF.

Diagnostics

We have discovered that soluble endoglin levels are elevated in blood serum samples taken from women with a pregnancy related hypertensive disorder, such as pre-eclampsia or eclampsia. Soluble endoglin starts rising 6-10 weeks before clinical symptoms of preeclampsia. Accordingly, a diagnostic test measuring soluble endoglin and sFlt1, optionally in combination with PlGF, preferably free PlGF in the serum will have enhanced sensitivity and specificity, and provide a powerful tool in the prevention of preeclampsia-induced mortality. The diagnostic test can also include measuring the levels of free VEGF; TGF-β family members, preferably TGF-β1, TGF-β3, free activin-A, BMP2, BMP7; NOS, preferably eNOS; or PGI2, either alone or in any combination thereof.

While the methods described herein refer to pre-eclampsia and eclampsia specifically, it should be understood that the diagnostic and monitoring methods of the invention apply to any pregnancy related hypertensive disorder including, but not limited to, gestational hypertension, pregnancy with a small for gestational age (SGA) infant, HELLP, chronic hypertension, pre-eclampsia (mild, moderate, and severe), and eclampsia.

Levels of soluble endoglin, either free, bound, or total levels, are measured in a subject sample and used as an indicator of pre-eclampsia, eclampsia, or the propensity to develop such conditions.

A subject having pre-eclampsia, eclampsia, or a predisposition to such conditions will show an increase in the expression of a soluble endoglin polypeptide. The soluble endoglin polypeptide can include full-length soluble endoglin, degradation products, alternatively spliced isoforms of soluble endoglin, enzymatic cleavage products of soluble endoglin, and the like. An antibody that specifically binds a soluble endoglin polypeptide may be used for the diagnosis of pre-eclampsia or eclampsia or to identify a subject at risk of developing such conditions. One example of an antibody useful in the methods of the invention is a monoclonal antibody against the N-terminal region of endoglin that is commercially available from Santa Cruz Biotechnology, Inc. (cat #sc-20072). Additional examples include antibodies that specifically bind the extracellular domain of endoglin (e.g., amino acids 1 to 437 of endoglin, amino acids 1 to 587 of endoglin, or any of the amino acid sequences shown in bold and underlined in FIG. 30B). A variety of protocols for measuring an alteration in the expression of such polypeptides are known, including immunological methods (such as ELISAs and RIAs), and provide a basis for diagnosing pre-eclampsia or eclampsia or a risk of developing such conditions.

Increased levels of soluble endoglin are a positive indicator of pre-eclampsia or eclampsia. For example, if the level of soluble endoglin is increased relative to a reference (e.g., 10%, 20%, 30%, 40%, 50%, 60%, 70%, 80%, 90% or more), or increases over time in one or more samples from a subject, this is considered a positive indicator of pre-eclampsia or eclampsia. Additionally, any detectable alteration in levels of soluble endoglin, sFlt-1, VEGF, or PlGF relative to normal levels is indicative of eclampsia, pre-eclampsia, or the propensity to develop such conditions. Normally, circulating serum concentrations of soluble endoglin range from 2-7 ng/ml during the non-pregnant state and from 10-20 ng/ml during normal pregnancy. Elevated serum levels, greater than 15 ng/ml, preferably greater than 20 ng/ml, and most preferably greater than 25 ng/ml or more, of soluble endoglin is considered a positive indicator of pre-eclampsia or eclampsia.

In one embodiment, the level of soluble endoglin is measured in combination with the level of sFlt-1, VEGF, or PlGF polypeptide or nucleic acid, or any combination thereof. Methods for the measurement of sFlt-1, VEGF, and PlGF are described in U.S. Patent Application Publication Numbers 20040126828, 20050025762, and 20050170444 and PCT Publication Numbers WO 2004/008946 and WO 2005/077007, hereby incorporated by reference in their entirety. In additional preferred embodiments, the body mass index (BMI) and gestational age of the fetus is also measured and included the diagnostic metric.

In another embodiment, the level of TGF-β1, TGF-β3, or eNOS polypeptide or nucleic acid is measured in combination with the level of soluble endoglin, sFlt-1, VEGF, or PlGF polypeptide or nucleic acid. Antibodies useful for the measurement of TGF-β1 and β3 polypeptide levels are commercially available, for example, from Abcam, Abgent, BD Biosciences Pharmingen, Chemicon, GeneTex, and R&D Systems. The level of PGI$_2$ can also be used in combination with the level of any of the above polypeptides. PGI$_2$ levels can be determined, for example, using the PGI$_2$ receptor as a binding molecule in any of the diagnostic assays described above, or using, for example, the urinary prostacyclin colorimetric ELISA kit (Assay Designs). Antibodies useful for the measurement of eNOS polypeptide levels are commercially available, for example, from Research Diagnostics Inc., Santa Cruz, Cayman Chemicals, and BD Biosciences.

In one embodiment, a metric incorporating soluble endoglin, sFlt-1, VEGF, or PlGF, or any combination therein, is used to determine whether a relationship between levels of at least two of the proteins is indicative of pre-eclampsia or eclampsia. In one example, the metric is a PAAI (sFlt-1/VEGF+PlGF), which is used, in combination with soluble endoglin measurement, as an anti-angiogenic index that is diagnostic of pre-eclampsia, eclampsia, or the propensity to develop such conditions. If the level of soluble endoglin is increased relative to a reference sample (e.g., 1.5-fold, 2-fold, 3-fold, 4-fold, or even by as much as 10-fold or more), and the PAAI is greater than 10, more preferably greater than 20, then the subject is considered to have pre-eclampsia, eclampsia, or to be in imminent risk of developing the same. The PAAI (sFlt-1/VEGF+PlGF) ratio is merely one example of a useful metric that may be used as a diagnostic indicator. It is not intended to limit the invention. Virtually any metric that detects an alteration in the level of soluble endoglin, sFlt-1, PlGF, or VEGF, or any combination thereof, in a subject relative to a normal control may be used as a diagnostic indicator. Another example is the following soluble endoglin anti-angiogenic index: (sFlt-1+0.25(soluble endoglin polypeptide))/PlGF. An increase in the value of the soluble endoglin metric over time or compared to a reference sample or value is a diagnostic indicator of pre-eclampsia or eclampsia. A soluble endoglin index above 100, preferably above 200 is a diagnostic indicator of pre-eclampsia or eclampsia. Another example are the following indexes: (soluble endoglin+sFlt-1)/PlGF or sFlt-1× soluble endoglin. In addition, the metric can further include the level of TGF-β1, TGF-β3, PGI$_2$, or eNOS polypeptide. Any of the metrics can further include the BMI of the mother or the GA of the infant.

Standard methods may be used to measure levels of soluble endoglin, VEGF, PlGF, or sFlt-1 polypeptide in any bodily fluid, including, but not limited to, urine, serum, plasma, saliva, amniotic fluid, or cerebrospinal fluid. Preferably, free VEGF or free PlGF is measured. Such methods include immunoassay, ELISA, western blotting using antibodies directed to soluble endoglin, VEGF, PlGF or sFlt-1, and quantitative enzyme immunoassay techniques such as those described in Ong et al. (*Obstet. Gynecol.* 98:608-611, 2001) and Su et al. (*Obstet. Gynecol.*, 97:898-904, 2001). ELISA is the preferred method for measuring levels of soluble endoglin, VEGF, PlGF, or sFlt-1. Preferably, soluble endoglin is measured.

Oligonucleotides or longer fragments derived from an endoglin, sFlt-1, PlGF, or VEGF nucleic acid sequence may be used as a probe not only to monitor expression, but also to identify subjects having a genetic variation, mutation, or polymorphism in an endoglin, sFlt-1, PlGF, or VEGF nucleic acid molecule that are indicative of a predisposition to develop the pre-eclampsia or eclampsia. Such methods are described in detail in Abdalla et al., *Hum. Mutat.* 25:320-321 (2005), U.S. Patent Application Publication No. 2006/0067937 and PCT Publication No. WO 06/034507. Preferred oligonucleotides will hybridize at high stringency to the extracellular domain of endoglin or to any nucleic acid sequence encoding any of the peptides shown in bold and underlined in FIG. 30B.

The measurement of any of the nucleic acids or polypeptides described herein can occur on at least two different occasions and an alteration in the levels as compared to normal reference levels over time is used as an indicator of pre-eclampsia, eclampsia, or the propensity to develop such conditions.

In one example, the level of a soluble endoglin polypeptide or nucleic acid present in the bodily fluids of a subject having pre-eclampsia, eclampsia, or the propensity to develop such conditions may be increased by as little as 10%, 20%, 30%, or 40%, or by as much as 50%, 60%, 70%, 80%, 90%, 95%, 96%, 97%, 98%, 99% or more relative to levels in a normal control subject or relative to a previous sampling obtained from the same bodily fluids of the same subject. In another example, the level of a soluble endoglin polypeptide or nucleic acid in the bodily fluids of a subject having pre-eclampsia, eclampsia, or the propensity to develop such conditions may be altered by as little as 10%, 20%, 30%, or 40%, or by as much as 50%, 60%, 70%, 80%, 90%, 95%, 96%, 97%, 98%, 99% over time from one measurement to the next.

The level of sFlt-1, VEGF, or PlGF measured in combination with the level of soluble endoglin in the bodily fluids of a subject having pre-eclampsia, eclampsia, or the propensity to develop such conditions may be altered by as little as 10%, 20%, 30%, or 40%, or by as much as 50%, 60%, 70%, 80%, 90%, 95%, 96%, 97%, 98%, 99% or more relative to the level of sFlt-1, VEGF, or PlGF in a normal control. The level of sFlt-1, VEGF, or PlGF measured in combination with the level of soluble endoglin in the bodily fluids of a subject having pre-eclampsia, eclampsia, or the propensity to develop such conditions may be altered by as little as 10%, 20%, 30%, or 40%, or by as much as 50%, 60%, 70%, 80%, 90%, 95%, 96%, 97%, 98%, 99% over time from one measurement to the next.

In one embodiment, a subject sample of a bodily fluid (e.g., urine, plasma, serum, amniotic fluid, or cerebrospinal fluid) is collected early in pregnancy prior to the onset of pre-eclampsia symptoms. In another example, the sample can be a tissue or cell collected early in pregnancy prior to the onset of pre-eclampsia symptoms. Non-limiting examples of tissues and cells include placental tissue, placental cells, circulating endothelial cells, and leukocytes such as monocytes. In humans, for example, maternal blood serum samples are collected from the antecubital vein of pregnant women during the first, second, or third trimesters of the pregnancy. Preferably, the assay is carried out during the first trimester, for example, at 4, 6, 8, 10, or 12 weeks, or any interval therein, or during the second trimester, for example at 14, 16, 18, 20, 22, or 24 weeks, or any interval therein. In one example, the assay is carried out between 13 and 16 weeks of pregnancy. Such assays may also be conducted at the end of the second trimester or the third trimester, for example at 26, 28, 30, 32, 34, 36, or 38 weeks, or any interval therein. It is preferable that levels of soluble endoglin be measured twice during this period of time. For the diagnosis of post-partum pre-eclampsia or eclampsia, assays for soluble endoglin may be carried out postpartum. For the diagnosis of a predisposition to pre-eclampsia or eclampsia, the assay is carried out prior to the onset of pregnancy or prior to the development of symptoms of pre-eclampsia or eclampsia. In one example, for the monitoring and management of therapy, the assay is carried out during the pregnancy after the diagnosis of pre-eclampsia, and/or during therapy.

In one particular example, serial blood samples can be collected during pregnancy and the levels of soluble endoglin polypeptide determined by ELISA. In another example, a sample is collected during the second trimester and early in the third trimester and in increase in the level of soluble endoglin from the first sampling to the next is indicative of pre-eclampsia or eclampsia, or the propensity to develop either.

The invention also include the measurement of any ligands of soluble endoglin (e.g., TGF-β1, TGF-β3, activin-A, BMP-2, and BMP-7) ligand in a bodily fluid from a subject, preferably urine, and an alteration (e.g., increase or decrease) in the level of the soluble endoglin ligand is indicative of pre-eclampsia or eclampsia.

In veterinary practice, assays may be carried out at any time during the pregnancy, but are, preferably, carried out early in pregnancy, prior to the onset of pre-eclampsia symptoms. Given that the term of pregnancies varies widely between species, the timing of the assay will be determined by a veterinarian, but will generally correspond to the timing of assays during a human pregnancy.

The diagnostic methods described herein can be used individually or in combination with any other diagnostic method described herein for a more accurate diagnosis of the presence of, severity of, or estimated time of onset of pre-eclampsia or eclampsia. In addition, the diagnostic methods described herein can be used in combination with any other diagnostic methods determined to be useful for the accurate diagnosis of the presence of, severity of, or estimated time of onset of pre-eclampsia or eclampsia.

The diagnostic methods described herein can also be used to monitor and manage pre-eclampsia or eclampsia in a subject. In one example, a therapy is administered until the blood, plasma, or serum soluble endoglin level is less than 25 ng/ml or until the serum endoglin levels return to the baseline level determined before onset of pre-eclampsia or eclampsia. In another example, if a subject is determined to have an increased level of soluble endoglin relative to a normal control then the therapy can be administered until the serum PlGF level rises to approximately 400 pg/mL or a return to baseline level prior to onset of pre-eclampsia or eclampsia. In this embodiment, the levels of soluble endoglin, sFlt-1, PlGF, and VEGF, or any and all of these, are measured repeatedly as a method of not only diagnosing disease but monitoring the treatment and management of the pre-eclampsia and eclampsia.

Diagnostic Kits

The invention also provides for a diagnostic test kit. For example, a diagnostic test kit can include binding agents (e.g., polypeptides or antibodies) that specifically bind to soluble endoglin and means for detecting, and more preferably evaluating, binding between the binding agent and the soluble endoglin polypeptide. For detection, either the binding agent or the soluble endoglin polypeptide is labeled, and either the binding agent or the soluble endoglin polypeptide is substrate-bound, such that soluble endoglin polypeptide-binding agent interaction can be established by determining the amount of label attached to the substrate following binding between the binding agent and the soluble endoglin polypeptide. A conventional ELISA is a common, art-known method for detecting antibody-substrate interaction and can be provided with the kit of the invention. Soluble endoglin polypeptides can be detected in virtually any bodily fluid including, but not limited to urine, serum, plasma, saliva, amniotic fluid, or cerebrospinal fluid. The invention also provides for a diagnostic test kit that includes a soluble endoglin nucleic acid that can be used to detect and determine levels of soluble endoglin nucleic acids. A kit that determines an alteration, for example, an increase, in the level of soluble endoglin polypeptide relative to a reference, such as the level present in a normal control, is useful as a diagnostic kit in the methods of the invention.

The diagnostic kits of the invention can include antibodies or nucleic acids for the detection of sFlt-1, VEGF, or PlGF polypeptides or nucleic acids as described U.S. Patent Application Publication Numbers 20040126828, 20050025762, and 20050170444 and PCT Publication Numbers WO 2004/008946 and WO 2005/077007.

In another embodiment, the kit can also include binding agents for the detection of TGF-β1, TGF-β3, or eNOS polypeptide. Antibodies useful for the measurement of TGF-β1 and β3 polypeptide levels are commercially available, for example, from Abcam, Abgent, BD Biosciences Pharmingen, Chemicon, GeneTex, and R&D Systems. Antibodies useful for the measurement of eNOS polypeptide levels are commercially available, for example, from Research Diagnostics Inc., Santa Cruz, Cayman Chemicals, and BD Biosciences. Binding agents for the detection of $PGI_2$ levels can also be included and include for example the $PGI_2$ receptor, or fragments thereof, as a binding molecule in any of the diagnostic assays described above, or using, for example, the urinary prostacyclin colorimetric ELISA kit (Assay Designs). Antibodies useful for the measurement of eNOS polypeptide levels are commercially available, for example, from Research Diagnostics Inc. A kit that determines an alteration, for example, a decrease, in the level of eNOS, TGF-β1 or β3 polypeptide or $PGI_2$ relative to a reference, such as the level present in a normal control, is useful as a diagnostic kit in the methods of the invention.

Desirably, the kit includes any of the components needed to perform any of the diagnostic methods described above. For example, the kit desirably includes a membrane, where the soluble endoglin binding agent or the agent that binds the soluble endoglin binding agent is immobilized on the membrane. The membrane can be supported on a dipstick structure where the sample is deposited on the membrane by placing the dipstick structure into the sample or the membrane can be supported in a lateral flow cassette where the sample is deposited on the membrane through an opening in the cassette.

The diagnostic kits also generally include a label or instructions for the intended use of the kit components and a reference sample or purified proteins to be used to establish a standard curve. In one example, the kit contains instructions for the use of the kit for the diagnosis of a pregnancy related hypertensive disorder, such as pre-eclampsia, eclampsia, or the propensity to develop pre-eclampsia or eclampsia. In yet another example, the kit contains instructions for the use of the kit to monitor therapeutic treatment or dosage regimens for the treatment of pre-eclampsia or eclampsia. The diagnostic kit may also include a label or instructions for the use of the kit to determine the PAAI or soluble endoglin anti-angiogenesis index of the subject sample and to compare the PAAI or soluble endoglin anti-angiogenesis index to a reference sample value. It will be understood that the reference sample values will depend on the intended use of the kit. For example, the sample can be compared to a normal reference value, wherein an increase in the PAAI or soluble endoglin anti-angiogenesis index or in the soluble endoglin value is indicative of pre-eclampsia or eclampsia, or a predisposition to pre-eclampsia or eclampsia. In another example, a kit used for therapeutic monitoring can have a reference PAAI or soluble endoglin anti-angiogenesis index value or soluble endoglin value that is indicative of pre-eclampsia or eclampsia, wherein a decrease in the PAAI or soluble endoglin anti-angiogenesis index value or a decrease in the soluble endoglin value of the subject sample relative to the reference sample can be used to indicate therapeutic efficacy or effective dosages of therapeutic compounds. A standard curve of levels of purified protein within the normal or positive reference range, depending on the use of the kit, can also be included.

Therapeutics

The present invention features methods and compositions for treating or preventing pre-eclampsia or eclampsia in a subject. Given that levels of soluble endoglin are increased in subjects having pre-eclampsia, eclampsia, or having a predisposition to such conditions, any compound that decreases the expression levels and/or biological activity of a soluble endoglin polypeptide or nucleic acid molecule is useful in the methods of the invention. Such compounds include TGF-β1, TGF-β3, activin-A, BMP2, or BMP7, that can disrupt soluble endoglin binding to ligands; a purified antibody or antigen-binding fragment that specifically binds soluble endoglin; antisense nucleobase oligomers; and dsRNAs used to mediate RNA interference. Additional useful compounds include any compounds that can alter the biological activity of soluble endoglin, for example, as measured by an angiogenesis assay. Exemplary compounds and methods are described in detail below. These methods can also be combined with methods to decrease sFlt-1 levels or to increase VEGF or PlGF levels or decrease sFlt-1 levels as described in PCT Publication Number WO 2004/008946 and U.S. Patent Publication Nos. 20040126828 and 20050170444. In addition, any compound that increases the level or biological activity of TGF-β1 or 3, eNOS, or PGI2. Exemplary compounds and methods are described in detail below. It should be noted the results described herein indicate that the soluble endoglin and sFlt-1 pathways may function in a cooperative manner to further the pathogenesis of pre-eclampsia or eclampsia. Therefore, the invention includes any combination of any of the methods or compositions described herein for the treatment or prevention of a pregnancy related hypertensive disorder. For example, a compound that targets the soluble endoglin pathway (e.g., downregulates soluble endoglin expression or biological activity or upregulates TGF-β, eNOS, or PGI$_2$ expression or biological activity) can be used in combination with a compound that targets the sFlt-1 pathway (e.g., downregulates sFlt-1 expression or biological activity or upregulates VEGF or PlGF expression of biological activity) for the treatment or prevention of a pregnancy related hypertensive disorder.

Therapeutics Targeting the TGF-β Signaling Pathway

TGF-β is the prototype of a family of at least 25 growth factors which regulate growth, differentiation, motility, tissue remodeling, neurogenesis, wound repair, apoptosis, and angiogenesis in many cell types. TGF-β also inhibits cell proliferation in many cell types and can stimulate the synthesis of matrix proteins. Unless evidenced from the context in which it is used, the term TGF-β as used throughout this specification will be understood to generally refer to any and all members of the TGF-β superfamily as appropriate. Soluble endoglin binds several specific members of the TGF-β family including TGF-β1, TGF-β3, activin, BMP-2 and BMP-7, and may serve to deplete the developing fetus or placenta of these necessary mitogenic and angiogenic factor. The present invention features methods of increasing the levels of these ligands to bind to soluble endoglin and to neutralize the effects of soluble endoglin.

Soluble Endoglin Ligands as Therapeutic Compounds

In a preferred embodiment of the present invention, purified forms of any soluble endoglin ligand such as TGF-β family proteins, including but not limited to TGF-β1, TGF-β3, activin-A, BMP2, and BMP7, are administered to the subject in order to treat or prevent pre-eclampsia or eclampsia.

Purified TGF-β family proteins include any protein with an amino acid sequence that is homologous, more desirably, substantially identical to the amino acid sequence of TGF-β1 or TGF-β3, or any known TGF-β family member, that can induce angiogenesis. Non-limiting examples include human TGF-β1 (Cat #240-B-002) and human TGF-β3 (Cat #243-B3-002) from R & D Systems, MN.

Therapeutic Compounds that Inhibit Proteolytic Cleavage of Endoglin

We have identified a potential cleavage site in the extracellular domain of endoglin where a proteolytic enzyme could cleave the membrane bound form of endoglin, releasing the extracellular domain as a soluble form. Our sequence alignments of the cleavage site suggest that a matrix metalloproteinase (MMP) may be responsible for the cleavage and release of soluble endoglin. Alternatively, a cathepsin or an elastase may also be involved in the cleavage event. MMPs are also known as collagenases, gelatinases, and stromelysins and there are currently 26 family members known (for a review see Whittaker and Ayscough, *Cell Transmissions* 17:1 (2001)). A preferred MMP is MMP9, which is known to be up-regulated in placentas from pre-eclamptic patients (Lim et al., *Am. J Pathol.* 151:1809-1818, 1997). The activity of MMPs is controlled through activation of pro-enzymes and inhibition by endogenous inhibitors such as the tissue inhibitors of metalloproteinases (TIMPS). Inhibitors of MMPs are zinc binding proteins. There are 4 known endogenous inhibitors (TIMP 1-4), which are reviewed in Whittaker et al., supra. One preferred MMP inhibitor is the inhibitor of membrane type-MMP1 that has been shown to cleave betaglycan, a molecule that shares similarity to enodglin (Velasco-Loyden et al., *J. Biol. Chem.* 279:7721-7733 (2004)). In addition, a variety of naturally-occurring and synthetic MMP inhibitors have been identified and are also reviewed in Whittaker et al., supra. Examples include antibodies directed to MMPs, and various compounds including marimastat, batimastat, CT1746, BAY 12-9566, Prinomastat, CGS-27023A, D9120, BMS275291 (Bristol Myers Squibb), and trocade, some of which are currently in clinical trials. Given the potential role of MMPs, cathepsins, or elastases in the release and up-regulation of soluble endoglin levels, the present invention also provides for the use of any compound, such as those described above, known to inhibit the activity of any MMP, cathepsin, or elastase involved in the cleavage and release of soluble endoglin, for the treatment or prevention of pre-eclampsia or eclampsia in a subject.

Therapeutic Compounds that Increase Soluble Endoglin Binding Proteins

The present invention provides for the use of any compound known to stimulate or increase blood serum levels of soluble endoglin binding proteins, including but not limited to TGF-β1, TGF-β3, activin-A, BMP2, and BMP7, for the treatment or prevention of pre-eclampsia in a subject. These compounds can be used alone or in combination with the purified proteins described above or any of the other methods used to increase TGF-β family proteins protein levels described herein. In one example, cyclosporine is used at a dosage of 100-200 mg twice a day to stimulate TGF-β1 production.

Therapeutic Compounds that Alter the Anti-Angiogenic Activity of Soluble Endoglin Additional therapeutic compounds can be identified using angiogenesis assays. For example, pre-eclamptic serum having elevated levels of soluble endoglin are added to a matrigel tube formation assay will induce an anti-angiogenic state. Test compounds can then be added to the assay and a reversion in the anti-angiogenic state by 10%, 20%, 30%, 40%, 50%, 60%, 70%, 80%, 90% or more indicates that the compound can reduce the biological activity of soluble endoglin and is useful as a therapeutic compound.

Therapeutic Compounds that Increase the Levels or Biological Activity of NOS

NOS is a complex enzyme containing several cofactors, a heme group which is part of the catalytic site, an N-terminal oxygenase domain, which belongs to the class of haem-thiolate proteins, and a C-terminal reductase domain which is homologous to NADPH:P450 reductase. NOS produces NO by catalysing a five-electron oxidation of a guanidino nitrogen of L-arginine (L-Arg).

eNOS activation involves a coordinated increase in Ser1177 phosphorylation and Thr495 dephosphorylation. We have discovered that TGF-β1 dephosphorylates eNOS at Thr495, which is necessary to increase the Ca2+ sensitivity and enzyme activity and may work synergistically with VEGF, which activates eNOS by phosphorylating Ser1177.

Accordingly, any compound (e.g., polypeptide, nucleic acid molecule, small molecule compound, or antibody) that increases the level (e.g., by increasing stability, transcription or translation, or decreasing protein degradation) or biological activity of NOS, particularly eNOS, or any compound that prevents the downregulation of eNOS activity is useful in the methods of the invention. Such compounds include purified NOS, preferably eNOS, or biologically active fragments thereof, nucleic acids encoding NOS, preferably eNOS, or biologically active fragments thereof, statins, vanadate, hepatocyte growth factor, phosphoinositide 3-kinase (PI3K), Akt, VEGF, TGF-β1, or any other compound that increases Ser1177 phosphorylation or Thr495 dephosphorylation or both. Nitric oxide is synthesized from L-arginine by nitric oxide synthase located in endothelial and other cells. Nitric oxide can also be generated by application of various nitric oxide donors such as sodium nitroprusside, nitroglycerin, SIN-1, isosorbid mononitrate, isosorbid dinitrate, and the like. Accordingly, compounds that increase (e.g., by at least 10%, 20%, 30%, 40%, 50%, 60%, 70%, 80%, 90% or more) the level or biological activity of NOS can optionally be administered in combination with L-arginine or a nitric oxide donor (e.g., sodium nitroprusside, nitroglycerin, isosorbid-mononitrate, and isosorbo dinitrate). NOS activity can be assayed by standard methods known in the art, including but not limited to the citrulline assay and other assays described in U.S. Patent Application Publication No. 20050256199, the entire disclosure of which is herein incorporated by reference. The Thr495 residue of eNOS is located within the calmodulin (CaM)-binding domain of eNOS. Agonist-induced dephosphorylation of eNOS at Thr495 increases the binding of CaM to the enzyme (Fleming et al., *Circ Res.* 2001, 88: E68-75), thereby increasing its calcium sensitivity and activation. In addition to TGF-β1 described herein, other agonists that have been shown to cause Thr495 dephosphorylation of eNOS including bradykinin, histamine and VEGF. Thr495 dephosphorylation can be enhanced by the protein kinase C (PKC) inhibitor Ro 31-8220 (Calbiochem) or after PKC downregulation using phorbol 12-myristate 13-acetate (PMA) (Sigma Aldrich). Moreover, agonist-induced dephosphorylation of Thr495 has been shown to be $Ca^{2+}$/calmodulin-dependent and inhibitable by calyculin A (Sigma Aldrich), a protein phosphatase 1 (PP 1) inhibitor (Fleming I, et al. Circ Res. 2001, 88: E68-75). Additional compounds that effect eNOS dephosphorylation at Thr495 include histamine and bradykinin (Sigma Aldrich).

Therapeutic Compounds that Increase the Levels or Biological Activity of $PGI_2$ Prostacyclin is a member of the family of lipid molecules known as eicosanoids. It is produced in endothelial cells from prostaglandin H2 (PGH2) by the action of the enzyme prostacyclin synthase. $PGI_2$ biological activity includes inhibition of platelet aggregation, relaxation of smooth muscle, reduction of systemic and pulmonary vascular resistance by direct vasodilation, and natriuresis in kidney.

$PGI_2$ is an anti-thrombotic factor that is stimulated by both VEGF and TGF-β1. $PGI_2$ biological activity includes inhibition of platelet aggregation and relaxation of vascular smooth muscle and assays for $PGI_2$ biological activity include any platelet aggregation assay or other PGI2 assay known in the art such as those described in Jakubowski et al., *Prostaglandins* 47:404 (1994). The invention features the use of any compound that increases (e.g., by at least 10%, 20%, 30%, 40%, 50%, 60%, 70%, 80%, 90% or more) the level or activity of $PGI_2$, as measured by standard assays known in the art including but not limited to $PGI_2$ mimetics, iloprost, cicaprost, and aspirin. Additional compounds are known in the art and examples are described in U.S. Pat. No. 5,910,482, the entire disclosure of which is herein incorporated by reference.

Purified Proteins

For any of the purified proteins, or fragment thereof, the proteins are prepared using standard methods known in the art. Analogs or homologs of any of the therapeutic proteins described above are also included and can be constructed, for example, by making various substitutions of residues or sequences, deleting terminal or internal residues or sequences not needed for biological activity, or adding terminal or internal residues which may enhance biological activity. Amino acid substitutions, deletions, additions, or mutations can be made to improve expression, stability, or solubility of the protein in the various expression systems. Generally, substitutions are made conservatively and take into consideration the effect on biological activity. Mutations, deletions, or additions in nucleotide sequences constructed for expression of analog proteins or fragments thereof must, of course, preserve the reading frame of the coding sequences and preferably will not create complementary regions that could hybridize to produce secondary mRNA structures such as loops or hairpins which would adversely affect translation of the mRNA.

Any of the therapeutic compounds of the invention (e.g., polypeptide, antibodies, small molecule compounds) can also include any modified forms. Examples of post-translational modifications include but are not limited to phosphorylation, glycosylation, hydroxylation, sulfation, acetylation, isoprenylation, proline isomerization, subunit dimerization or multimerization, and cross-linking or attachment to any other proteins, or fragments thereof, or membrane components, or fragments thereof (e.g., cleavage of the protein from the membrane with a membrane lipid component attached). Modifications that provide additional advantages such as increased affinity, decreased off-rate, solubility, stability and in vivo or in vitro circulating time of the polypeptide, or decreased immunogenicity and include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Creighton, "Proteins: Structures and Molecular Properties," 2d Ed., W. H. Freeman and Co., N.Y., 1992; "Postranslational Covalent Modification of Proteins," Johnson, ed., Academic Press, New York, 1983; Seifter et al., *Meth. Enzymol.*, 182:626-646, 1990; Rattan et al., *Ann. NY Acad. Sci.*, 663:48-62, 1992) are also included. The peptidyl therapeutic compound of the invention can also include sequence variants of any of the compounds such as variants that include 1, 2, 3, 4, 5, greater than 5, or greater than 10 amino acid alterations such as substitutions, deletions, or insertions with respect to wild type sequence. Additionally, the therapeutic compound of the invention may contain one or more non-classical amino acids. Non-classical amino acids include, but are not limited to, to the D-isomers of the common amino acids, 2,4-diaminobutyric acid, α-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue.

In addition, chemically modified derivatives of the therapeutic compounds described herein, which may provide additional advantages such as increased solubility, stability and circulating time of the polypeptide, or decreased immunogenicity (see U.S. Pat. No. 4,179,337) are also included. The chemical moieties for derivitization may be selected from water soluble polymers such as, for example, polyethylene glycol, ethylene glycol/propylene glycol copolymers, carboxymethylcellulose, dextran, polyvinyl alcohol and the like. The compound may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72, (1996); Vorobjev et al., *Nucleosides Nucleotides* 18:2745-2750, (1999); and Caliceti et al., *Bioconjug. Chem.* 10:638-646, (1999), the disclosures of each of which are incorporated by reference.

Any of the therapeutic compounds of the present invention (e.g., polypeptide, antibodies, or small molecule compounds) may also be modified in a way to form a chimeric molecule comprising the therapeutic compound fused to another, heterologous polypeptide or amino acid sequence, such as an Fc sequence, a detectable label, or an additional therapeutic molecule. In one example, an anti-soluble endoglin antibody can be a peptide fused to an Fc fusion protein.

For any of the polypeptides, including antibodies, that are used in the methods of the invention, the nucleic acids encoding the polypeptides or antibodies, or fragments thereof, are also useful in the methods of the invention using standard techniques for gene therapy known in the art and described herein. The invention also includes mimetics, based on modeling the 3-dimensional structure of a polypeptide or peptide fragment and using rational drug design to provide potential inhibitor compounds with particular molecular shape, size and charge characteristics. Following identification of a therapeutic compound, suitable modeling techniques known in the art can be used to study the functional interactions and design mimetic compounds which contain functional groups arranged in such a manner that they could reproduced those interactions. The designing of mimetics to a known pharmaceutically active compound is a known approach to the development of pharmaceuticals based on a lead compound. This might be desirable where the active compound is difficult or expensive to synthesize or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property. The mimetic or mimetics can then be screened to see whether they reduce or inhibit soluble endoglin levels or biological activity and further optimization or modification can then be carried out to arrive at one or more final mimetics for in vivo or clinical testing.

Therapeutic Nucleic Acids

Recent work has shown that the delivery of nucleic acid (DNA or RNA) capable of expressing an endothelial cell mitogen such as VEGF to the site of a blood vessel injury will induce proliferation and reendothelialization of the injured vessel. While the present invention does not relate to blood vessel injury, these general techniques for the delivery of nucleic acid to endothelial cells can be used in the present invention for the delivery of nucleic acids encoding soluble endoglin binding proteins, such as TGF-$\beta$1, TGF-$\beta$3, activin-A, BMP2 and BMP7, or eNOS. The techniques can also be used for the delivery of nucleic acids encoding proteins, such as those described above, known to inhibit the activity of any MMP, cathepsin, or elastase involved in the cleavage and release of soluble endoglin, for the treatment or prevention of pre-eclampsia or eclampsia in a subject. These general techniques are described in U.S. Pat. Nos. 5,830,879 and 6,258,787 and are incorporated herein by reference.

In the present invention the nucleic acid may be any nucleic acid (DNA or RNA) including genomic DNA, cDNA, and mRNA, encoding a soluble endoglin binding proteins such as TGF-$\beta$1, TGF-$\beta$3, activin-A, BMP2 and BMP7, or eNOS. The nucleic acids encoding the desired protein may be obtained using routine procedures in the art, e.g. recombinant DNA, PCR amplification.

Modes for Delivering Nucleic Acids

For any of the nucleic acid applications described herein, standard methods for administering nucleic acids can be used. Examples are described in U.S. Patent Application Publication No. 20060067937 and PCT Publication No. WO 06/034507.

Therapeutic Nucleic Acids that Inhibit Soluble Endoglin Expression

The present invention also features the use of antisense nucleobase oligomers to downregulate expression of soluble endoglin mRNA directly. By binding to the complementary nucleic acid sequence (the sense or coding strand), antisense nucleobase oligomers are able to inhibit protein expression presumably through the enzymatic cleavage of the RNA strand by RNAse H. Preferably the antisense nucleobase oligomer is capable of reducing soluble endoglin protein expression in a cell that expresses increased levels of soluble endoglin. Preferably the decrease in soluble endoglin protein expression is at least 10% relative to cells treated with a control oligonucleotide, preferably 20% or greater, more preferably 40%, 50%, 60%, 70%, 80%, 90% or greater. Methods for selecting and preparing antisense nucleobase oligomers are well known in the art. For an example of the use of antisense nucleobase oligomers to downregulate VEGF expression see U.S. Pat. No. 6,410,322, incorporated herein by reference. Methods for assaying levels of protein expression are also well known in the art and include western blotting, immunoprecipitation, and ELISA.

The present invention also features the use of RNA interference (RNAi) to inhibit expression of soluble endoglin. RNA interference (RNAi) is a recently discovered mechanism of post-transcriptional gene silencing (PTGS) in which double-stranded RNA (dsRNA) corresponding to a gene or mRNA of interest is introduced into an organism resulting in the degradation of the corresponding mRNA. In the RNAi reaction, both the sense and anti-sense strands of a dsRNA molecule are processed into small RNA fragments or segments ranging in length from 21 to 23 nucleotides (nt) and having 2-nucleotide 3' tails. Alternatively, synthetic dsRNAs, which are 21 to 23 nt in length and have 2-nucleotide 3' tails, can be synthesized, purified and used in the reaction. These 21 to 23 nt dsRNAs are known as "guide RNAs" or "short interfering RNAs" (siRNAs).

The siRNA duplexes then bind to a nuclease complex composed of proteins that target and destroy endogenous mRNAs having homology to the siRNA within the complex. Although the identity of the proteins within the complex remains unclear, the function of the complex is to target the homologous mRNA molecule through base pairing interactions between one of the siRNA strands and the endogenous mRNA. The mRNA is then cleaved approximately 12 nt from the 3' terminus of the siRNA and degraded. In this manner, specific genes can be targeted and degraded, thereby resulting in a loss of protein expression from the targeted gene. siRNAs can also be chemically synthesized or obtained from a company that chemically synthesizes siRNAs (e.g., Dharmacon Research Inc., Pharmacia, or ABI).

The specific requirements and modifications of dsRNA are described in PCT Publication No. WO01/75164, and in U.S. Patent Application Publication No. 20060067937 and PCT Publication No. WO 06/034507, incorporated herein by reference.

Soluble Endoglin Based Therapeutic Compounds Useful in Early Pregnancy

Inhibition of full-length endoglin signaling has been shown to enhance trophoblast invasiveness in villous explant cultures (Caniggia I et al, *Endocrinology*, 1997, 138:4977-88). Soluble endoglin is therefore likely to enhance trophoblast invasiveness during early pregnancy. Accordingly, compositions that increase soluble endoglin levels early in pregnancy in a woman who does not have a pregnancy related hypertensive disorder or a predisposition to a pregnancy related hypertensive disorder may be beneficial for enhancing placentation. Examples of compositions that increase soluble endoglin levels include purified soluble endoglin polypeptides, soluble endoglin encoding nucleic acid molecules, and compounds or growth factors that increase the levels or biological activity of soluble endoglin.

Assays for Gene and Protein Expression

The following methods can be used to evaluate protein or gene expression and determine efficacy for any of the above-mentioned methods for increasing soluble endoglin binding protein levels, or for decreasing soluble endoglin protein levels.

Blood serum from the subject is measured for levels of soluble endoglin, using methods such as ELISA, western blotting, or immunoassays using specific antibodies. Blood serum from the subject can also be measured for levels of TGF-β1, TGF-β3, activin-A, BMP2, BMP7, or any protein ligand known to bind to soluble endoglin. Methods used to measure serum levels of proteins include ELISA, western blotting, or immunoassays using specific antibodies. In addition, in vitro angiogenesis assays can be performed to determine if the subject's blood has converted from an anti-angiogenic state to a pro-angiogenic state. Such assays are described above in Example 4. A result that is diagnostic of pre-eclampsia or eclampsia is considered an increase of at least 10%, 20%, preferably 30%, more preferably at least 40% or 50%, and most preferably at least 60%, 70%, 80%, 90% or more in the levels of soluble endoglin and a result indicating an improvement in the pre-eclampsia or eclampsia is a decrease of at least 10%, 20%, preferably 30%, more preferably at least 40% or 50%, and most preferably at least 60%, 70%, 80%, 90% or more in the levels of soluble endoglin. Alternatively or additionally, a result that is diagnostic of pre-eclampsia or eclampsia is considered a decrease of at least 10%, 20%, preferably 30%, more preferably at least 40% or 50%, and most preferably at least 60%, 70%, 80%, 90% or more in the levels of eNOS, $PGI_2$, TGF-β1, TGF-β3, activin-A, BMP2, BMP7, or any protein ligand known to bind to soluble endoglin and a result indicating an improvement in the pre-eclampsia or eclampsia is an increase of at least 10%, 20%, preferably 30%, more preferably at least 40% or 50%, and most preferably at least 60%, 70%, 80%, 90% or more in the levels of eNOS, $PGI_2$, TGF-β1, TGF-β3, activin-A, BMP2, BMP7, or any protein ligand known to bind to soluble endoglin. A result indicating an improvement in the pre-eclampsia or eclampsia can also be considered conversion by at least 10%, preferably 20%, 30%, 40%, 50%, and most preferably at least 60%, 70%, 80%, 90% or more from an anti-angiogenic state to a pro-angiogenic state using the in vitro angiogenesis assay.

Blood serum or urine samples from the subject can also be measured for levels of nucleic acids or polypeptides encoding eNOS, TGF-β1, TGF-β3, activin-A, BMP2, BMP7, or soluble endoglin. There are several art-known methods to assay for gene expression. Some examples include the preparation of RNA from the blood samples of the subject and the use of the RNA for northern blotting, PCR based amplification, or RNAse protection assays. A positive result is considered an increase of at least 10%, 20%, preferably 30%, more preferably at least 40% or 50%, and most preferably at least 60%, 70%, 80%, 90% or more in the levels of soluble endoglin, TGF-β1, TGF-β3, activin-A, BMP2, BMP7 nucleic acids.

Use of Antibodies for Therapeutic Treatment

The elevated levels of soluble endoglin found in the serum samples taken from pregnant women suffering from pre-eclampsia suggests that soluble endoglin is acting as a "physiologic sink" to bind to and deplete the trophoblast cells and maternal endothelial cells of functional growth factors required for the proper development and angiogenesis of the fetus or the placenta. The use of compounds, such as antibodies, to bind to soluble endoglin and neutralize the activity of soluble endoglin (e.g., binding to TGF-β1, TGF-β3, activin-A, BMP2, BMP7), may help prevent or treat pre-eclampsia or eclampsia, by producing an increase in free TGF-β1, TGF-β3, activin-A, BMP2, and BMP7. Such an increase would allow for an increase in trophoblast proliferation, migration and angiogenesis required for placental development and fetal nourishment, and for systemic maternal endothelial cell health.

The present invention provides antibodies that bind specifically to soluble endoglin. Preferably, the antibodies bind to the extracellular domain of endoglin or to the ligand binding domain. The antibodies are used to neutralize the activity of soluble endoglin and the most effective mechanism is believed to be through direct blocking of the binding sites for TGF-β1, TGF-β3, activin-A, BMP2, or BMP7, however, other mechanisms cannot be ruled out. Preferred antibodies can bind to any one or more of the peptide sequences indicated in bold and underlined in FIG. 30B or to any of the preferred fragments of soluble endoglin (e.g., amino acids 1 to 437, 4 to 437, 40 to 406, or 1 to 587 of human endoglin). Methods for the preparation and use of antibodies for therapeutic purposes are described in several patents including U.S. Pat. Nos. 6,054,297; 5,821,337; 6,365,157; and 6,165, 464; U.S. Patent Application Publication No. 2006/0067937; and PCT Publication No. WO 06/034507 and are incorporated herein by reference. Antibodies can be polyclonal or monoclonal; monoclonal humanized antibodies are preferred.

Therapeutic Uses of Antibodies

When used in vivo for the treatment or prevention of pre-eclampsia or eclampsia, the antibodies of the subject invention are administered to the subject in therapeutically effective amounts. Preferably, the antibodies are administered parenterally or intravenously by continuous infusion. The dose and dosage regimen depends upon the severity of the disease, and the overall health of the subject. The amount of antibody administered is typically in the range of about 0.001 to about 10 mg/kg of subject weight, preferably 0.01 to about 5 mg/kg of subject weight.

For parenteral administration, the antibodies are formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The antibodies typically are formulated in such vehicles at concentrations of about 1 mg/ml to 10 mg/ml.

Combination Therapies

Optionally, a therapeutic may be administered in combination with any other standard pre-eclampsia or eclampsia therapy; such methods are known to the skilled artisan and include the methods described in U.S. Patent Application Publication Numbers 20040126828, 20050025762, 20050170444, and 2006/0067937 and PCT Publication Numbers WO 2004/008946, WO 2005/077007, and WO 06/034507.

Desirably, the invention features the use of a combination of any one or more of the therapeutic agents described herein. Given our discovery that soluble endoglin and sFlt-1 may act in concert to induce vascular damage and pregnancy related hypertensive disorders by interfering with TGF-β1 and VEGF signaling pathway respectively, possibly converging on the NOS signaling pathway, therapeutic methods of the invention include the administration of a compound that decrease sFlt-1 levels or activity or increase VEGF or PlGF levels or activity in combination with a compound that decreases soluble endoglin levels or activity or increase TGF-β, NOS, or PGI2 levels or activity. It will be understood by the skilled artisan that any combination of any of the agents can be used for this purpose. For example, an antibody that specifically binds to soluble endoglin can be administered in combination with VEGF. In another example, a compound that increases TGF-β1 levels or activity can be administered in combination with a compound that increases VEGF or PlGF in order to target both the endoglin and the VEGF pathway. Alternatively, a combination of antibodies against both soluble endoglin and sFlt-1 may be used either directly or in an ex vivo approach (e.g., using a column that is lined with anti-soluble endoglin or sFlt-1 and circulating the patient's blood through the column). Any of these combinations can further include the administration of a compound that increases NOS levels or activity, preferably eNOS, in order to regulate the pathway downstream of the respective receptors.

In addition, the invention provides for the use of any chronic hypertension medications used in combination with any of the therapeutic methods described herein. Medications used for the treatment of hypertension during pregnancy include methyldopa, hydralazine hydrochloride, or labetalol. For each of these medications, modes of administration and dosages are determined by the physician and by the manufacturer's instructions.

Dosages and Modes of Administration

Preferably, the therapeutic is administered during pregnancy for the treatment or prevention of pre-eclampsia or eclampsia or after pregnancy to treat post-partum pre-eclampsia or eclampsia. Techniques and dosages for administration vary depending on the type of compound (e.g., chemical compound, purified protein, antibody, antisense, RNAi, or nucleic acid vector) and are well known to those skilled in the art or are readily determined.

Therapeutic compounds of the present invention may be administered with a pharmaceutically acceptable diluent, carrier, or excipient, in unit dosage form. Administration may be parenteral, intravenous, subcutaneous, oral or local by direct injection into the amniotic fluid. Intravenous delivery by continuous infusion is the preferred method for administering the therapeutic compounds of the present invention. The therapeutic compound may be in form of a solution, a suspension, an emulsion, an infusion device, or a delivery device for implantation, or it may be presented as a dry powder to be reconstituted with water or another suitable vehicle before use.

The composition can be in the form of a pill, tablet, capsule, liquid, or sustained release tablet for oral administration; or a liquid for intravenous, subcutaneous or parenteral administration; or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The compound may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The dosage and the timing of administering the compound depends on various clinical factors including the overall health of the subject and the severity of the symptoms of pre-eclampsia. In general, once pre-eclampsia or a predisposition to pre-eclampsia is detected, continuous infusion of the purified protein is used to treat or prevent further progression of the condition. Treatment can be continued for a period of time ranging from 1 to 100 days, more preferably 1 to 60 days, and most preferably 1 to 20 days, or until the completion of pregnancy. Dosages vary depending on each compound and the severity of the condition and are titrated to achieve a steady-state blood serum concentration ranging from 10 to 20 ng/ml soluble endoglin; and/or 1 to 500 pg/mL free VEGF or free PlGF, or both, preferably 1 to 100 pg/mL, more preferably 5 to 50 pg/mL and most preferably 5 to 10 pg/mL VEGF or PlGF, or 1-5 ng of sFlt-1.

The diagnostic methods described herein can be used to monitor the pre-eclampsia or eclampsia during therapy or to determine the dosages of therapeutic compounds. In one example, a therapeutic compound is administered and the PAAI is determined during the course of therapy. If the PAAI is less than 20, preferably less than 10, then the therapeutic dosage is considered to be an effective dosage. In another example, a therapeutic compound is administered and the soluble endoglin anti-angiogenic index is determined during the course of therapy. If the soluble endoglin anti-angiogenic index is less than 200, preferably less than 100, then the therapeutic dosage is considered to be an effective dosage.

Subject Monitoring

The disease state or treatment of a subject having pre-eclampsia, eclampsia, or a predisposition to such a condition can be monitored using the diagnostic methods, kits, and compositions of the invention. For example, the expression of a soluble endoglin polypeptide present in a bodily fluid, such as urine, plasma, amniotic fluid, or CSF, can be monitored. The soluble endoglin monitoring can be combined with methods for monitoring the expression of an sFlt-1, VEGF, or PlGF, TGF-β, or eNOS polypeptide or nucleic acid, or PGI2. Such monitoring may be useful, for example, in assessing the efficacy of a particular drug in a subject or in assessing disease progression. Therapeutics that decrease the expression or biological activity of a soluble endoglin nucleic acid molecule or polypeptide are taken as particularly useful in the invention.

Screening Assays

As discussed above, the level of a soluble endoglin nucleic acid or polypeptide is increased in a subject having pre-eclampsia, eclampsia, or a predisposition to such conditions. Based on these discoveries, compositions of the invention are useful for the high-throughput low-cost screening of candidate compounds to identify those that modulate the expression of a soluble endoglin polypeptide or nucleic acid molecule whose expression is altered in a subject having a pre-eclampsia or eclampsia.

Any number of methods are available for carrying out screening assays to identify new candidate compounds that alter the expression of a soluble endoglin nucleic acid molecule. Examples are described in detail in U.S. Patent Application Publication No. 20060067937 and PCT Publication No. WO 06/034507.

In one working example, candidate compounds may be screened for those that specifically bind to a soluble endoglin polypeptide. The efficacy of such a candidate compound is dependent upon its ability to interact with such a polypeptide or a functional equivalent thereof. Such an interaction can be readily assayed using any number of standard binding techniques and functional assays such as immunoassays or affinity chromatography based assays (e.g., those described in Ausubel et al., supra). In one embodiment, a soluble endoglin polypeptide is immobilized and compounds are tested for the ability to bind to the immobilized soluble endoglin using standard affinity chromatography based assays. Compounds that bind to the immobilized soluble endoglin can then be eluted and purified and tested further for its ability to bind to soluble endoglin both in vivo and in vitro or its ability to inhibit the biological activity of soluble endoglin.

In another example, a candidate compound is tested for its ability to decrease the biological activity of a soluble endoglin polypeptide by decreasing binding of a soluble endoglin polypeptide and a growth factor, such as TGF-β1, TGF-β3, activin-A, BMP-2 and BMP-7. These assays can be performed in vivo or in vitro and the biological activity of the soluble endoglin polypeptide can be assayed using any of the assays for any of the soluble endoglin activities known in the art or described herein. For example, cells can be incubated with a Smad2/3-dependent reporter construct. If desired, the cells can also be incubated in the presence of TGF-β to enhance the signal on the Smad2/3 dependent reporter construct. The cells can then be incubated in the presence of soluble endoglin which will reduce or inhibit TGF-β-induced activation of the Smad2/3 dependent reporter construct. Candidate compounds can be added to the cell and any compound that results in an increase of TGF-β-induced activation of the Smad2/3 dependent reporter in the soluble endoglin treated cells as compared to cells not treated with the compound, is considered a compound that may be useful for the treatment of pre-eclampsia or eclampsia.

In another example, the TGF-β-induced dephosphorylation of eNOS at Thr495 can also be used as an assay for changes in soluble endoglin biological activity. In this example, cells are incubated in the presence of soluble endoglin, which as shown in the experiments described below, inhibits the TGF-β1 dephosphorylation of Thr495 of eNOS. Candidate compounds are then added to the cells and the phosphorylation state of Thr495 is determined. Any compound that results in an increase of TGF-β-induced activation of Thr495 dephosphorylation in the soluble endoglin treated cells as compared to cells not treated with the compound, is considered a compound that may be useful for the treatment of pre-eclampsia or eclampsia.

EXAMPLES

The following examples are intended to illustrate the invention. They are not meant to limit the invention in any way.

Example 1

Increased Levels of Endoglin mRNA and Protein in Pregnant Women with Pre-Eclampsia In an attempt to identify novel secreted factors playing a pathologic role in pre-eclampsia, we performed gene expression profiling of placental tissue from 17 pregnant women with pre-eclampsia and 13 normal pregnant women using Affymetrix U95A microarray chips. We found that the gene for endoglin was upregulated in women with pre-eclampsia.

Figure 3:
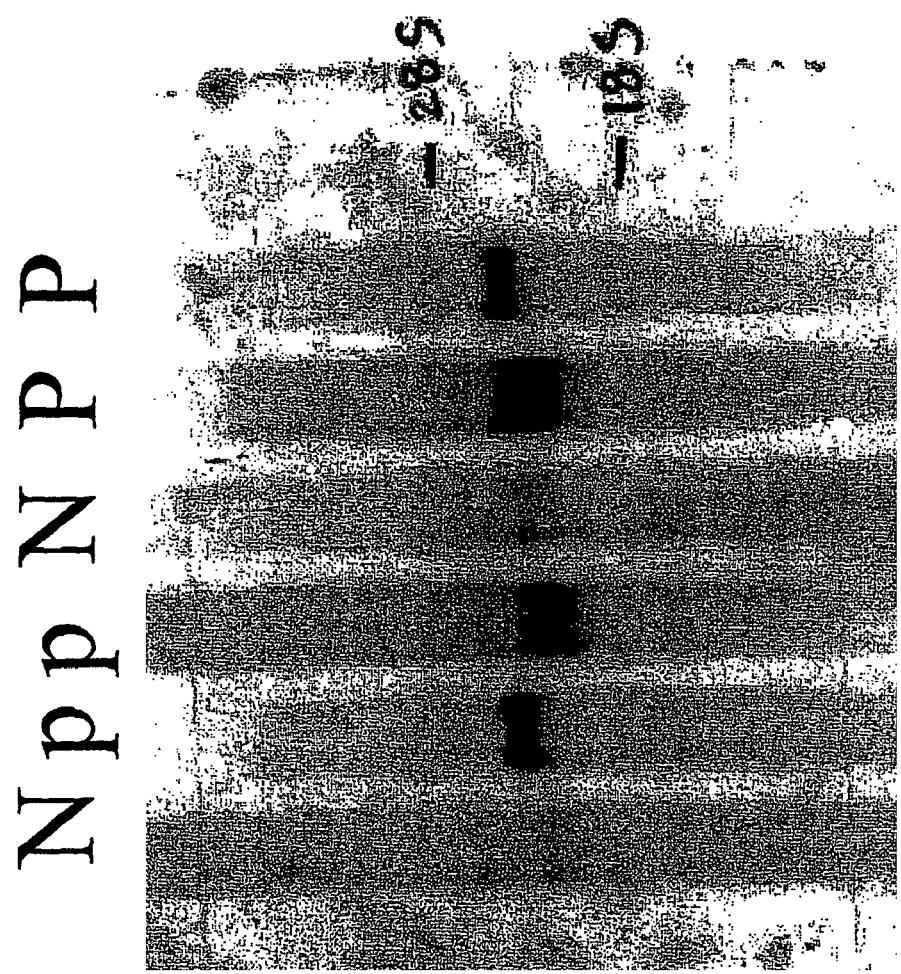
FIG. 3 is a Northern blot showing endoglin mRNA levels in placentas from normal pregnancies (N), placentas from pre-term pre-eclamptic pregnancies (p) and placentas from term pre-eclamptic pregnancies (P).

In order to confirm the upregulation of endoglin in pre-eclampsia, we performed Northern blots to analyze the placental endoglin mRNA levels (FIG. 3) and western blot analysis to measure serum protein levels of endoglin (FIG. 4) in pre-eclamptic pregnant women as compared with normotensive pregnant women. Pre-eclampsia was defined as (1) a systolic blood pressure (BP)>140 mmHg and a diastolic BP>90 mmHg after 20 weeks gestation, (2) new onset proteinuria (1+ by dipstik on urinalysis, >300 mg of protein in a 24 hour urine collection, or random urine protein/creatinine ratio >0.3, and (3) resolution of hypertension and proteinuria by 12 weeks postpartum. Patients with underlying hypertension, proteinuria, or renal disease were excluded. Patients were divided into mild and severe pre-eclampsia based on the presence or absence of nephrotic range proteinuria (>3 g of protein on a 24 hour urine collection or urine protein/creatinine ratio greater than 3.0). The mean urine protein/creatinine ratios in the mild pre-eclampsia group were 0.94+/−0.2 and in the severe pre-eclampsia group were 7.8+/−2.1. The mean gestational ages of the various groups were as follows: normal 38.8+/−0.2 weeks, mild pre-eclampsia 34+/−1.2 weeks, severe pre-eclampsia 31.3+/−0.6 weeks, and pre-term 29.5+/−2.0 weeks. Placental samples were obtained immediately after delivery. Four random samples were taken from each placenta, placed in RNAlater stabilization solution (Ambion, Austin, Tex.) and stored at −70° C. RNA isolation was performed using Qiagen RNAeasy Maxi Kit (Qiagen, Valencia, Calif.).

Northern blots probed with a 400 base pair probe in the coding region of endoglin (Unigene Hs.76753) corresponding to the N-terminal region (gene bank #BC014271) and an 18S probe as a normalization control showed an increase in placental endoglin mRNA (see Knebelmann et al., *Cancer Res.* 58:226-231 (1998)). Western blots probed with an antibody to the amino terminus of endoglin showed an increase in both placental and maternal serum levels of endoglin protein in pre-eclamptic pregnant women as compared to normotensive pregnant women.

Example 2

Figure 4:
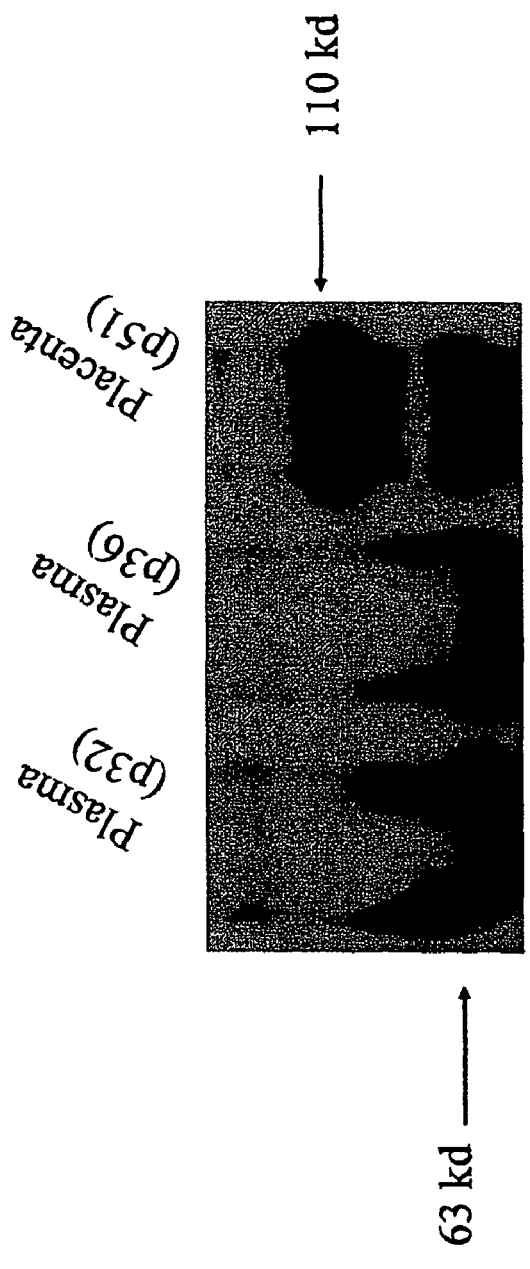
FIG. 4 is a western blot showing endoglin protein levels in the placenta. Samples are from two pre-eclamptic patients, p32 and p36, that presented to the Beth Israel Deaconess Medical Center in 2003 and maternal serum from a pregnant woman. The Western blot was probed using a N-terminal antibody obtained from Santa Cruz Biotechnology, Inc., (Santa Cruz, Calif.) that shows both the 110 kD band in the placenta and a smaller 63 kD band that is present in the placenta and the serum samples.
Figure 5:
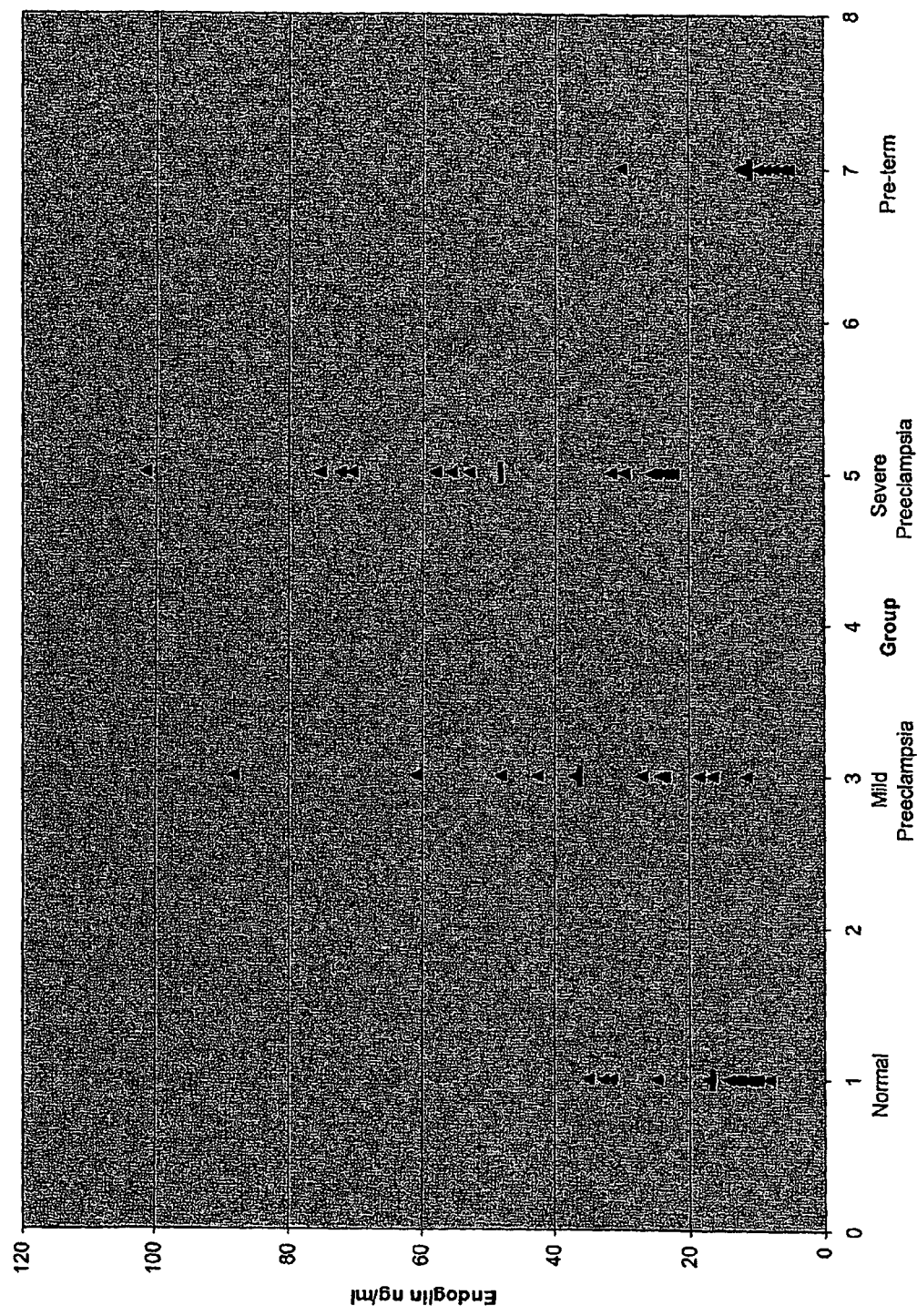
FIG. 5 is a graph that shows the circulating concentrations of soluble endoglin in women with normal pregnancy, mild pre-eclampsia, severe pre-eclampsia and non-pre-eclamptic pregnancies complicated by pre-term delivery. All blood specimens were obtained within 24 hours prior to delivery. Soluble endoglin was measured using an ELISA kit from R & D Systems, MN (Cat # DNDG00). These data show that soluble endoglin levels are significantly elevated in pre-eclamptic patients at the time of clinical disease.
Figure 30A:
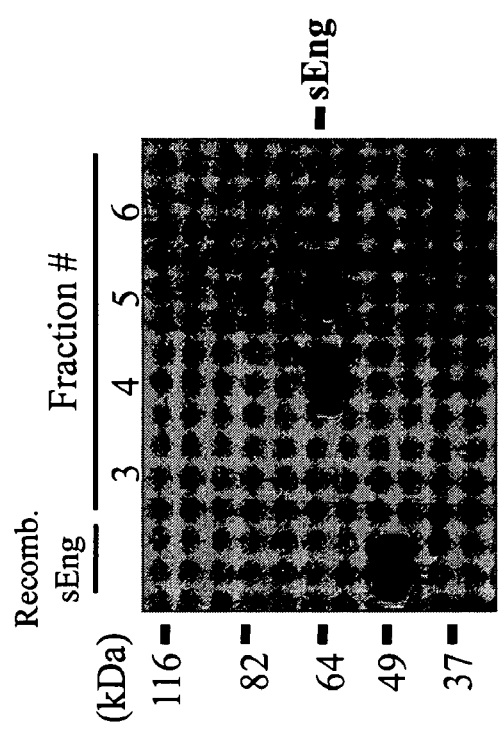
FIG. 30A is a western blot showing soluble endoglin after purification the serum of preeclamptic patients. Fractions 4 and 5 eluted from the 44G4-IgG (anti-Eng) Sepharose were run on SDS-PAGE under reducing conditions and tested by Western blot using a polyclonal antibody to endoglin. The eluted fractions were subjected to mass spectrometry analysis (3 runs).

Demonstration of a Soluble Endoglin Polypeptide in the Placentas and Serum of Pre-Eclamptic Patients The western blot analysis used to measure the levels of endoglin protein in placentas and serum from pre-eclamptic women suggested the presence of a smaller protein (approximately 63-65 kDa), that was present in the placenta and serum of pre-eclamptic pregnant women (FIGS. 4 and 30A). We have demonstrated that this smaller fragment is the extracellular domain of endoglin. This truncated version is likely to be shed from the placental syncitiotrophoblasts and endothelial cells and circulated in excess quantities in patients with pre-eclampsia. This soluble form of endoglin may be acting as an anti-angiogenic agent by binding to circulating ligands that are necessary for normal vascular health.

The predicted length of the soluble form of the protein is approximately 437 amino acids (including the peptide leader sequence, 412 amino acids without the leader sequence). sEng was purified from the serum of preeclamptic patients. Fractions 4 and 5 eluted from the 44G4-IgG (anti-Eng) Sepharose, were run on SDS-PAGE under reducing conditions and tested by Western blot using a polyclonal antibody to Eng. The eluted fractions were subjected to mass spectrometry analysis (3 runs) and the peptides identified are shown in (FIG. 30B). The purification and analysis by mass spectrometry revealed several Eng-specific peptides ranging from Gly40 to Arg406 indicating a soluble form (soluble endoglin) corresponding to the N-terminal region of the full-length protein bold on the sequence of human endoglin.

Example 3

Circulating Concentrations of Soluble Endoglin in Women with Normal Versus Pre-Eclamptic Pregnancies In order to compare the levels of circulating, soluble endoglin from the serum of normal, mildly pre-eclamptic, or severely pre-eclamptic women, we performed ELISA analysis on blood samples taken from these women. All the patients for this study were recruited at the Beth Israel Deaconess Medical Center after obtaining appropriate IRB-approved consents. Pre-eclampsia was defined as (1) Systolic BP>140 and diastolic BP>90 after 20 weeks gestation in a previously normotensive patient, (2) new onset proteinuria (1+ by dipstick on urinalysis or >300 mg of protein in a 24 hr urine collection or random urine protein/creatinine ratio >0.3), and (3) resolution of hypertension and proteinuria by 12 weeks postpartum. Patients with baseline hypertension, proteinuria, or renal disease were excluded. For the purposes of this study, patients were divided into mild and severe pre-eclampsia based on the absence or presence of nephrotic-range proteinuria (>3 g of protein on a 24 hour urine collection or urine protein to creatinine ratio greater than 3.0). HELLP syndrome was defined when patients had evidence of thrombocytopenia (<100000 cells/µl), increased LDH (>600 IU/L) and increased AST (>70 IU/L). Healthy pregnant women were included as controls. 8 patients with pre-term deliveries for other medical reasons were included as additional controls. Placental samples were obtained immediately after delivery. Serum was collected from pregnant patients at the time of delivery (0-12 hours prior to delivery of the placenta) after obtaining informed consent. These experiments were approved by the Institutional Review Board at the Beth Israel Deaconess Medical Center.

Figure 28:
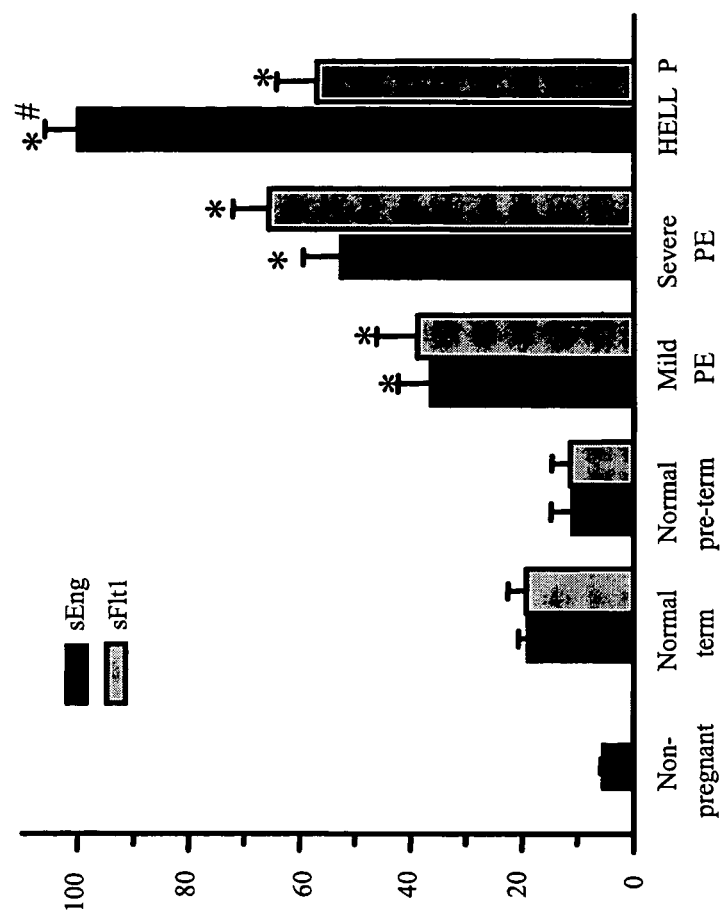
FIG. 28 is a graph showing the ELISA results for soluble endoglin (sEng) and sFlt1 in sera of patients with varying degrees of preeclampsia, control pregnancies and four non-pregnant healthy volunteers as described in Example 3. *$P<0.05$ compared to pre-term controls and #$P<0.05$ compared to severe preeclampsia.
Figure 29:
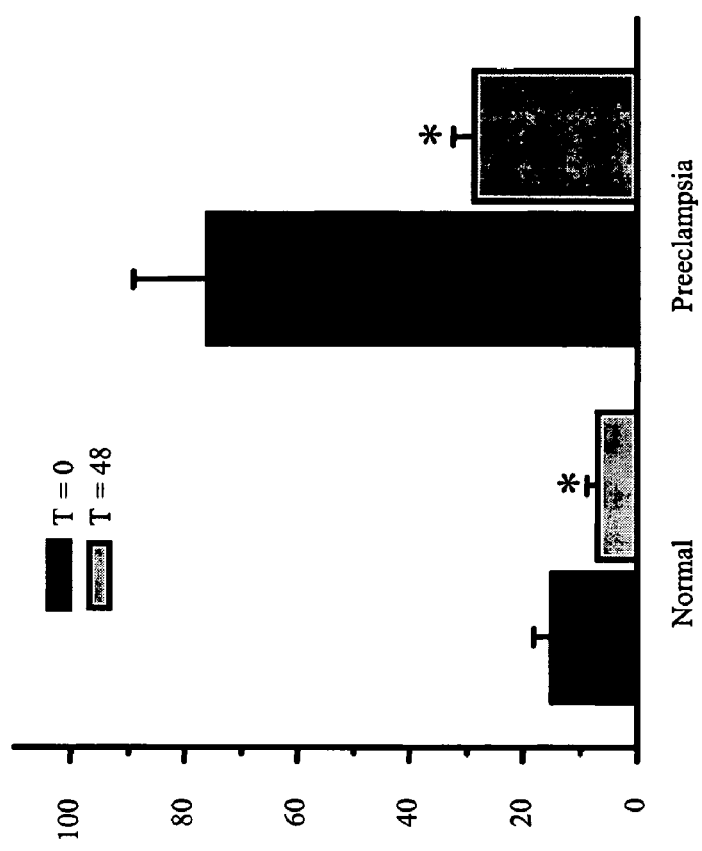
FIG. 29 is a graph showing ELISA results for soluble endoglin in a subset of pregnant patients (normal: n=6; preeclampsia: n=11) described in Example 3 with blood drawn pre- (0-12 hours) and post- (48 hours) delivery. *$P<0.05$ as compared to T=0 samples.

Using the serum specimens from patients described in Table 1, we measured the circulating concentrations of soluble endoglin in the various groups of pre-eclamptic patients and control pregnant patients. When pre-eclamptic patients were further sub-divided into those with and without HELLP, sEng concentrations were three-, five- and ten-fold higher in mild, severe and HELLP syndrome preeclamptics, respectively, compared to gestational age-matched pre-term controls (FIG. 28). Concentrations of sEng in pregnant patients correlated with those of sFlt1 ($R^2$=0.56), except in the HELLP group where sEng was higher than sFlt1. In a subset of patients, blood samples obtained 48 hours after placental delivery showed a 70% reduction in mean sEng circulating levels in preeclamptic and normal pregnant patients (FIG. 29).

TABLE 1

Clinical characteristics and circulating soluble endoglin in the various patient groups

|  | Normal (n = 30) | Mild pre-eclampsia (n = 11) | Severe pre-eclampsia, no HELLP (n = 17) | Severe pre-eclampsia with HELLP (n = 11) | Pre-term (n = 8) |
| --- | --- | --- | --- | --- | --- |
| Maternal age (yrs) | 32.43 | 33.18 | 29.5 | 33.73 | 31.88 |
| Gestational age (wks) | 38.65 | 31.91* | 29.06* | 26.52* | 30.99* |
| Primiparous (%) | 43.3 | 63.6 | 47.1 | 90.9 | 62.5 |
| Systolic blood pressure (mmHg) | 122 | 157* | 170* | 166* | 123 |
| Diastolic blood pressure (mmHg) | 72 | 99* | 104* | 103* | 77 |
| Proteinuria (g protein/g creatinine) | 0.37 | 2.5* | 8.64* | 5.16* | 0.6 |
| Uric acid (mg/dl) | 5.27 | 6.24 | 7.29* | 6.31 | 7.35 |
| Hematocrit (%) | 35.5 | 33.6 | 33.7 | 33.5 | 34.3 |
| Platelet count | 238 | 230 | 249 | 69.4* | 229 |
| Creatinine (mg/dl) | 0.55 | 0.62 | 0.62 | 0.64 | 0.67 |
| Soluble endoglin in (ng/ml) | 18.73 | 36.12* | 52.55** | 99.83*** | 10.9 |

*$P < 0.05$,
**$P < 0.005$

Figure 18:
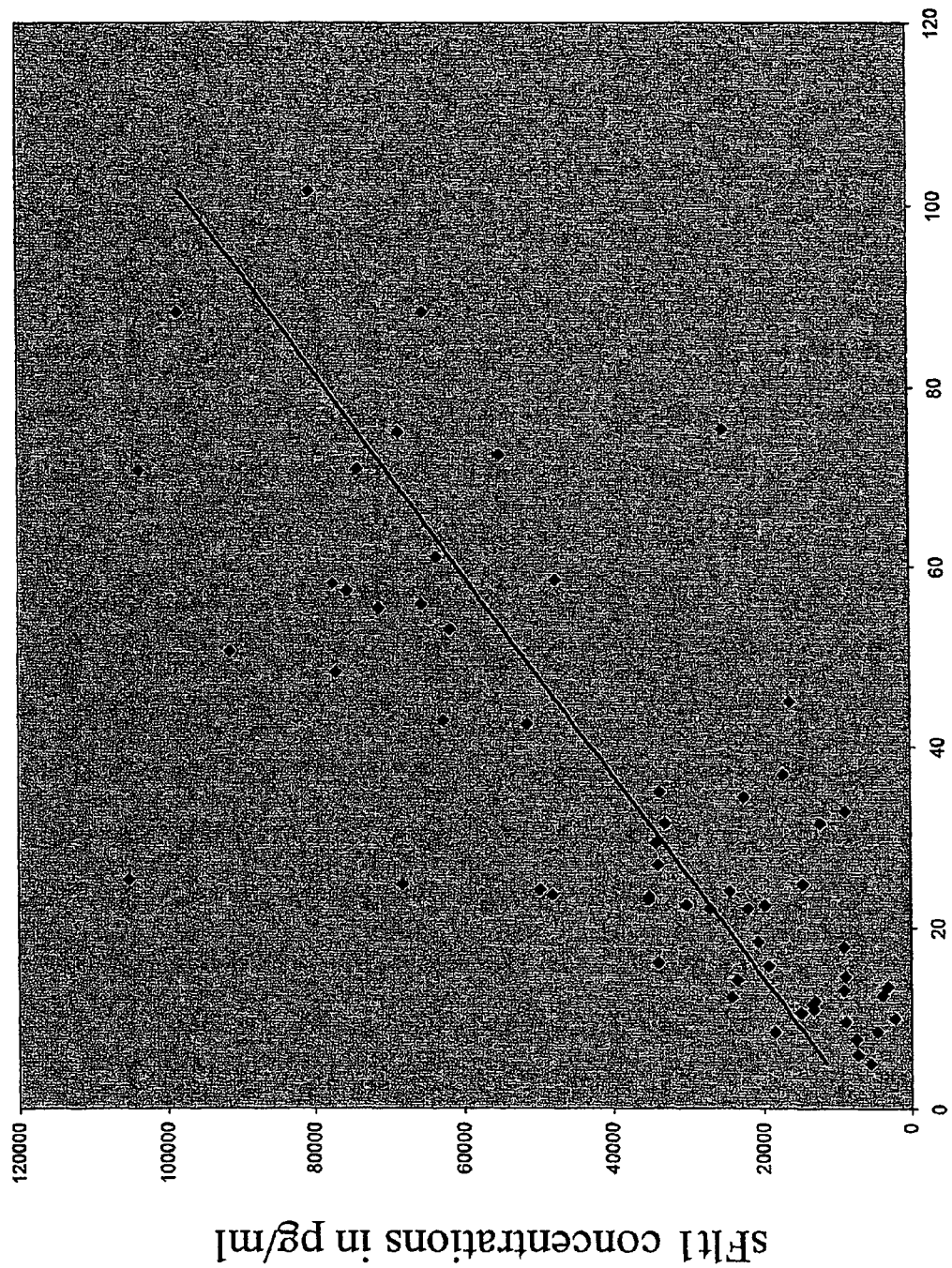
FIG. 18 is a graph showing the concentration of sFlt1 and soluble endoglin in the same pregnant patients plotted against each other.
Figure 19:
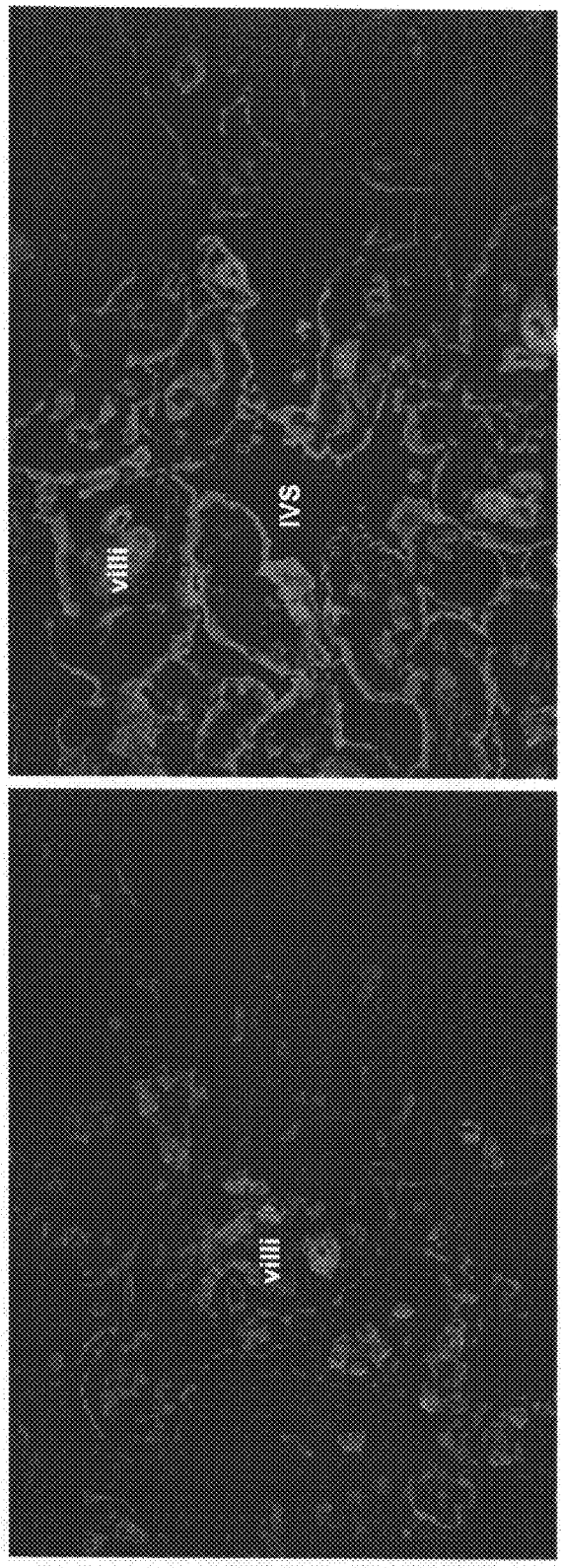
FIG. 19 shows photomicrographs of double immunofluorescence staining of endoglin (red) and smooth muscle actin (green) for pre-eclamptic placentas taken at 25.2 weeks. The antibody used to detect endoglin stains both full-length endoglin and the soluble endoglin. Control placentas for the appropriate gestational windows were derived from patients with pre-term labor.
Figure 20:
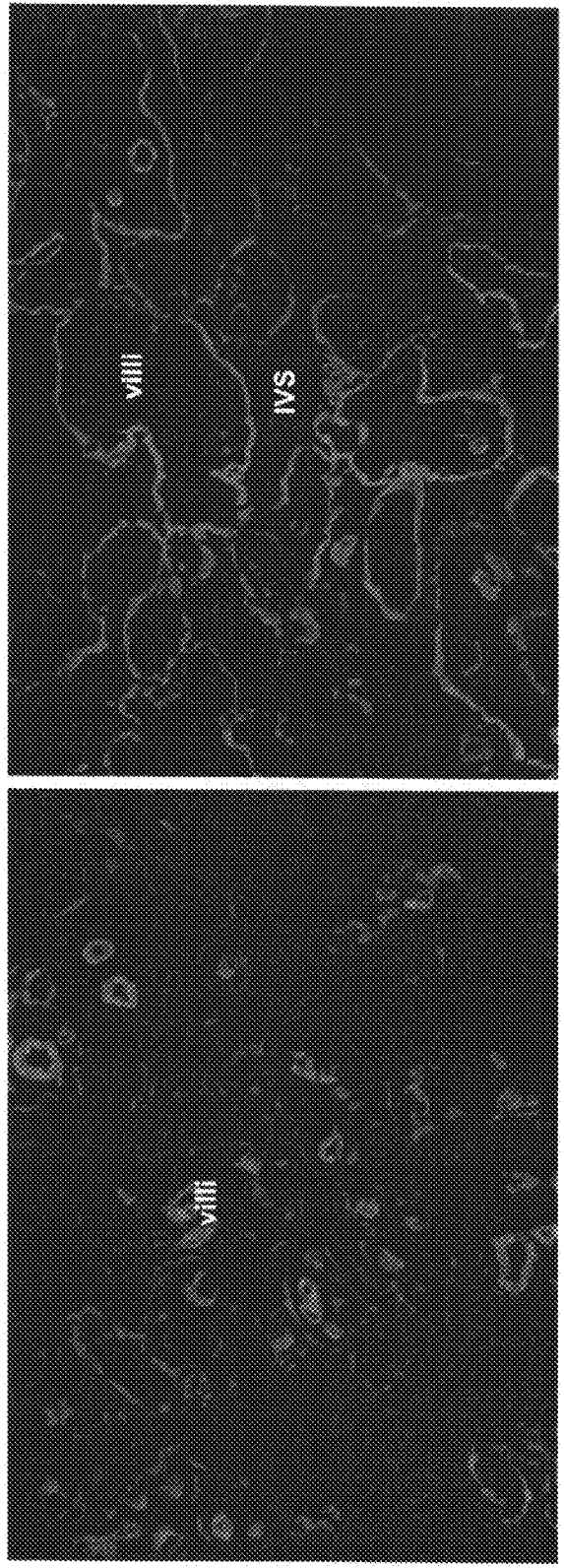
FIG. 20 shows photomicrographs of double immunofluorescence staining of endoglin (red) and smooth muscle actin (green) for pre-eclamptic placentas taken at 41.3 weeks. The antibody used to detect endoglin stains both full-length endoglin and the soluble endoglin. Control placentas for the appropriate gestational windows were derived from patients with pre-term labor.
Figure 21:
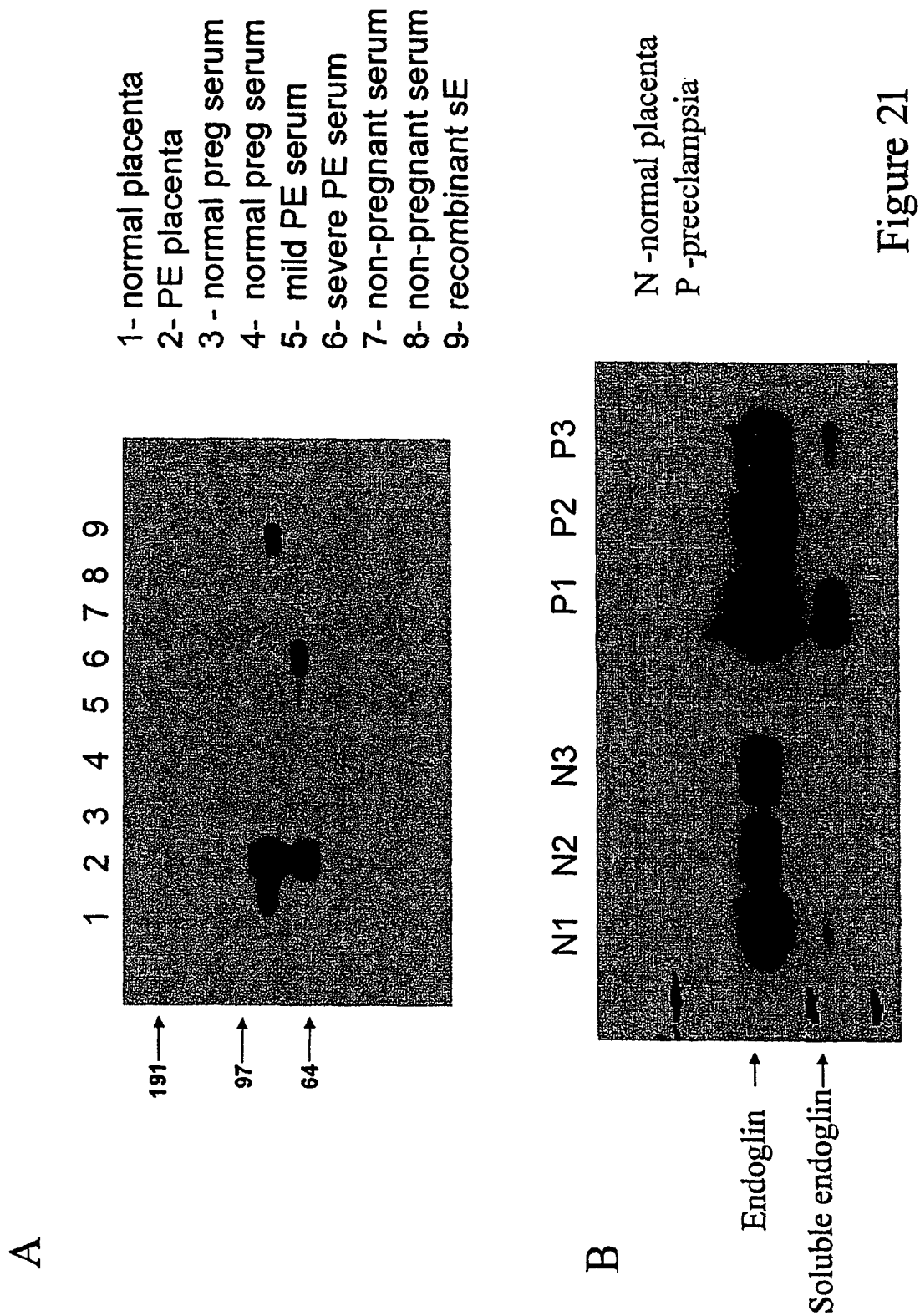
FIG. 21A shows an autoradiogram from immunoprecipitation and western blots experiments for endoglin using both pre-eclamptic placentas and serum.
FIG. 21B shows an autoradiogram from immunoprecipitation and western blots experiments for endoglin using pre-eclamptic placentas. The three different N and P samples represent individual patients. For both figures commercially available monoclonal antibodies were used for immunoprecipitation and polyclonal antibodies were used for the western blots. Both these antibodies were raised against the N-terminal region of the endoglin protein and detect both the full length and the truncated soluble endoglin protein.

The average serum concentrations of soluble endoglin was at least two fold higher in mild pre-eclampsia and 3-4 fold higher in patients with severe pre-eclampsia. In pre-eclamptic patients complicated with the HELLP syndrome, the concentration of soluble endoglin was at least 5-10 fold higher than gestational age matched control specimens. Additionally, the levels of soluble endoglin in pregnant patients correlate with the levels of sFlt-1 (FIG. 18). The R2 value for correlation was 0.6. (Note that the circulating concentrations of sFlt-1 reported here are at least 4-5 fold higher than previously published (Maynard et al., supra). This is due to a difference in the sensitivity of a new ELISA kit from R&D systems which lacks urea in the assay diluent and therefore gives consistently higher values than previously published.) In other words, patients with the highest levels of soluble endoglin also had the highest circulating levels of sFlt1. The origin of soluble endoglin is most likely the syncitiotrophoblast of the placenta as evidenced by the enhanced staining seen on our placental immunohistochemistry (FIGS. 19 and 20). These figures show that endoglin protein is expressed by the syncitiotrophoblasts and is vastly upregulated in pre-eclampsia. Our western blot data (FIGS. 21A and 21B) and the lack of detectable alternative splice variants by northern blot supports the notion that soluble endoglin is likely a shed form of the extracellular fomain of the membrane endoglin protein. It is approximately 65 kDA in size and is produced at elevated levels in pre-eclamptic placentas and it circulates in higher amounts in pre-eclamptic sera. This protein was present at much lower levels in the sera of normal pregnant women and barely detectable in non-pregnant women. Soluble endoglin expression in pre-eclamptic placenta was four-fold higher than in normal pregnancy (n=1−/group, P<0.01). Quantitation of sEng/Eng in these specimens showed no significant difference between normal (0.43) and preeclamptic (0.56) placentae (n=10/group, P=0.4), suggesting that sEng is derived from the full-length protein and that both Eng and sEng are similarly increased in preeclampsia.

The following methods were used for some of the experiments described in this example.

Immunohistochemistry

Immunohistochemistry on placental samples for endoglin and α-Smooth muscle actin (SMA) was done as reported by (Leach et al., Lancet 360:1215-1219 (2002)). Briefly, the frozen placenta section obtained from patients without preeclampsia (n=10) and with preeclampsia (n=10) slides were incubated with a serum-free protein blocking solution (DAKO) for 30 minutes at room temperature and then with the primary antibody at room temperature (mouse monoclonal anti-Endoglin: 1:50 dilution; DAKO) for 2 hours. The slides were then washed with phosphate buffered saline for 10 minutes. The secondary antibody, Rhodamine conjugated sheep anti-mouse IgG, 1:200 dilution (Biomeda) was applied for 1 hour. Sections were again washed with phosphate buffered saline and subsequently incubated with a 1:400 dilution of FITC-conjugated mouse anti-human SMA (Dako) for 30 minutes at room temperature. Immunoreactivity of Endoglin was reviewed using a SPOT advanced imaging system (RT SLIDER Diagnostic Instruments, Inc) by a pathologist who was blinded to the clinical diagnosis.

ELISA and Western Blots

ELISA was performed using a commercially available ELISA kit from R & D Systems, MN (for example, Cat #DNDG00) and as previously described (Maynard et al, J. Clin. Invest. 111:649-658, 2003). Western blots were performed essentially as described previously (Maynard et al, supra, and Kuo et al. Proc. Natl. Acad. Sci. 98:4605-4610 (2001))).

Immunoprecipitation (IP) Experiments

IP followed by western blots were used to identify and characterize soluble endoglin in the placental tissue and serum specimens from patients with pre-eclampsia. Human placental tissue was washed with cold PBS and lysed in homogenization buffer [10 mM Tris-HCl, pH 7.4; 15 mM NaCl; 60 mM KCl; 1 mM EDTA; 0.1 mM EGTA; 0.5% Nonidet P-40; 5% sucrose; protease mixture from Roche (Indianapolis, Ind.)] for 10 minutes. Placental lysates were then subjected to immunoprecipitation with an anti-human monoclonal mouse endoglin antibody (mAb P4A4, Santa Cruz Biotechnology, Inc., Santa Cruz, Calif.). Immunoaffinity columns were prepared by the directional coupling of 3-5 mg of the purified antibody to 2 ml protein A-Sepharose using an immunopure IgG orientation kit (Pierce Chemical Co., Rockford, Ill., USA) according to the manufacturer's instructions. Columns were then washed extensively with RIPA buffer containing protease mixture, and bound proteins were eluted with 0.1 mol/L glycine-HCl buffer, pH 2.8. The eluent was collected in 0.5-ml fractions containing 1 mol/L Tris-HCl buffer. Protein-containing fractions were pooled and concentrated 9- to 10-fold with CENTRICON Centrifugal Concentrator (Millipore Corp., Bedford, Mass., USA). The immunoprecipitated samples were separated on a 4-12% gradient gel (Invitrogen) and proteins were transferred to polyvinylidene difluoride (PVDF) membranes. Endoglin protein was detected by western blots using polyclonal anti-human rabbit endoglin primary antibody (H-300, Santa Cruz Biotechnology, Inc., Santa Cruz, Calif.).

Purification of Soluble Endoglin and Analysis by Mass Spectrometry

Serum (10 ml) from preeclamptic patients was sequentially applied onto CM Affi-gel blue and protein A Sepharose (Bio-Rad) columns to remove albumin and immunoglobulins, respectively. The flow through was slowly applied to a 2.5 ml column of mAb 44G4 IgG to human Eng, conjugated to Sepharose (Gougos et al., Int. Immuno. 4:83-92, (1992)). Bound fractions were eluted with 0.02 M diethylamine pH 11.4 and immediately neutralized with 1 M Tris pH 7.8. Fractions 4 and 5 with elevated absorbance at 280 nm were pooled, reduced with 10 mM DTT for 1 h at 57° C. and alkylated with 0.055 M iodoacetomide. The samples were then completely digested with trypsin (1:100). The lyophilized sample was resuspended in 0.1% tri-fluoroacetic acid and injected in a CapLC (Waters) HPLC instrument. Peptides were separated using a 75 µm Nano Series column (LC Packings) and analyzed using a Qstar XL MS/MS system. The data was searched using the Mascot search engine (Matrix Science) against the human protein database, NCBInr.

Example 4

Model Assay for Angiogenesis

An endothelial tube assay can be used an in vitro model of angiogenesis. Growth factor reduced Matrigel (7 mg/mL, Collaborative Biomedical Products, Bedford, Mass.) is placed in wells (100 µl/well) of a pre-chilled 48-well cell culture plate and is incubated at 37° C. for 25-30 minutes to allow polymerization. Human umbilical vein endothelial cells (30,000+ in 300 µl of endothelial basal medium with no serum, Clonetics, Walkersville, Md.) at passages 3-5 are treated with 10% patient serum, plated onto the Matrigel coated wells, and are incubated at 37° C. for 12-16 hours. Tube formation is then assessed through an inverted phase contrast microscope at 4× (Nikon Corporation, Tokyo, Japan) and is analyzed (tube area and total length) using the Simple PCI imaging analysis software.

Example 5

Soluble Endoglin Protein Levels as a Diagnostic Indicator of Pre-Eclampsia and Eclampsia in Women (Romero Study)

This study was designed to evaluate whether soluble endoglin is altered during clinical pre-eclampsia and whether it can be used to predict pre-eclampsia and eclampsia in women.

This study was done under collaboration with Dr. Roberto Romero, at the Wayne State University/NICHD Perinatology Branch, Detroit, Mich. A retrospective longitudinal case-control study was conducted using a banked biological sample database as previously described in Chaiworapongsa et al. (The Journal of Maternal-Fetal and Neonatal Medicine, Jan. 2005, 17 (1):3-18). All women were enrolled in the prenatal clinic at the Sotero del Rio Hospital, Santiago, Chile, and followed until delivery. Prenatal visits were scheduled at 4-week intervals in the first and second trimester, and every two weeks in the third trimester until delivery. Plasma samples were selected from each patient only once for each of the following six intervals: (1) 7-16 weeks, (2) 16-24 weeks, (3) 24-28 weeks, (4) 28-32 weeks, (5) 32-37 weeks, and (6) >37 weeks of gestation. For each pre-eclamptic case, one control was selected by matching for gestational age (+/−2 weeks) at the time of clinical diagnosis of pre-eclampsia. The clinical criteria for the diagnosis of pre-eclampsia were the same as previously described in Chaiworapongsa et al, supra.

Measurement of Plasma Endoglin Levels

The plasma samples stored at −70° C. were thawed and plasma soluble endoglin levels were measured in one batch using the commercially available ELISA kits from R&D systems, Minneapolis, Minn. (Catalog #DNDG00).

Statistical Analysis

Analysis of covariance was used to assess the difference in plasma concentrations of soluble endoglin between patients destined to develop pre-eclampsia and in normal pregnancy after adjusting for gestational age at blood sampling and intervals of sample storage. Chi-square or Fisher's exact tests were employed for comparisons of proportions. The statistics package used was SPSS V.12 (SPSS Inc., Chicago, Ill.). Significance was assumed for a p value of less than 0.05.

Results

The clinical characteristics of the study population are described in Table 2. The group with pre-eclampsia included more nulliparous women and delivered earlier than the control group. Importantly, the birth weights of the fetuses were smaller in the pre-eclamptic group and there were a higher proportion of women carrying small-for-gestational-age (SGA) infants.

TABLE 2

Clinical characteristics of the study population

| | Normal pregnancy n = 44 | Pre-eclampsia n = 44 | p |
|---|---|---|---|
| Age (y) | 29 ± 6 | 26 ± 6 | 0.04* |
| Nulliparity | 11 (25%) | 30 (68.2%) | <0.001* |
| Smoking | 10 (22.7%) | 1 (2.3%) | 0.007* |
| GA at delivery (weeks) | 39.7 ± 1.1 | 36.9 ± 2.7 | <0.001* |
| Birthweight (grams) | 3,372 ± 383 | 2,710 ± 766 | <0.001* |
| Birthweight <10$^{th}$ percentile | 0 | 16 (36.4%) | <0.001* |

Value expressed as mean ± sd or number (percent)
GA: gestational age

The clinical characteristics of patients with pre-eclampsia are described in Table 3. Thirty-two (72%) of the patients had severe pre-eclampsia, while 10 patients had severe early-onset pre-eclampsia defined as onset <34 weeks.

TABLE 3

Clinical characteristics of patients with pre-eclampsia

| Blood pressure (mmHg) | |
|---|---|
| Systolic | 155 ± 15 |
| Diastolic | 100 ± 8 |
| Mean arterial pressure | 118 ± 9 |
| Proteinuria (dipstick) | 3 ± 0.8 |
| Aspartate aminotransferase$^\alpha$ (SGOT) (U/L) | 29 ± 31 |
| Platelet count$^\beta$ (×10$^3$) (µ/L) | 206 ± 59 |
| Severe pre-eclampsia | 32 (72.7%) |
| GA at pre-eclampsia diagnosed ≦ 34 weeks | 10 (22.7%) |
| GA at pre-eclampsia diagnosed ≧ 37 weeks | 27 (61.4%) |

Value expressed as mean ± sd or number (percent)
$^\alpha$(n = 26);
$^\beta$(n = 42)

The serum soluble endoglin levels in the controls and the pre-eclamptic women measured in the 6 gestational age windows are shown in Table 4. Amongst the pre-eclamptics, their specimens were divided into two groups—clinical pre-eclampsia (samples taken at the time of symptoms of pre-eclampsia) and preclinical pre-eclampsia (samples taken prior to clinical symptoms). The data shows that at mid-pregnancy (24-28 weeks of gestation), serum soluble endoglin concentrations start rising in women destined to develop pre-eclampsia and become at least 3 fold higher than controls by 28-32 weeks of gestation. Blood samples taken from women with clinical pre-eclampsia show a very dramatic (nearly 10-15 fold) elevation when compared to gestational age matched controls.

To examine the relationship between plasma soluble endoglin concentrations and the interval to clinical diagnosis of pre-eclampsia, plasma samples of pre-eclamptic patients at different gestational ages were stratified according to the interval from blood sampling to clinical diagnosis into five groups: (1) at clinical diagnosis, (2) 2-5.9 weeks before clinical manifestation, (3) 6-10.9 weeks before clinical manifestation, (4) 11-15.9 weeks before clinical manifestation, and (5) 16-25 weeks before clinical manifestation. The data shown in Table 5 demonstrates that the plasma soluble endoglin levels start going up at 6-10.9 weeks before onset of symptoms in pre-eclamptics and are at least 3 fold higher at 2-5.9 weeks before symptoms in women destined to develop pre-eclampsia.

TABLE 4

Plasma soluble endoglin concentrations in normal pregnancy and pre-eclampsia

|  | Normal pregnancy | p | Pre-clinical samples Pre-eclampsia | p | Clinical samples Pre-eclampsia | $p^\beta$ |
|---|---|---|---|---|---|---|
| $1^{st}$ blood sampling (7.1-16 weeks) | | | | | | |
| Soluble Endoglin (ng/ml) | 3.89 ± .928 | 0.9 | 3.96 ± 1.28 | | | |
| Gestational age (weeks) | 12.3 ± 2.2 | 0.2 | 11.6 ± 2.4 | | | |
| Range | 8.4-15.9 | | 7.7-15.1 | | | |
|  | n = 37 | | n = 34 | | | |
| $2^{nd}$ blood sampling (16.1-24 weeks) | | | | | | |
| Soluble Endoglin (ng/ml) | 3.36 ± 1.11 | 0.1 | 3.79 ± 1.37 | | | |
| Gestational age (weeks) | 19.4 ± 1.7 | 0.06 | 20.2 ± 2.1 | | | |
| Range | 16.3-23.4 | | 16.7-24.0 | | | |
|  | n = 44 | | n = 36 | | | |
| $3^{rd}$ blood sampling (24.1-28 weeks) | | | | | | |
| Soluble Endoglin (ng/ml) | 3.18 ± .729 | 0.009* | 5.27 ± 4.12 | | | |
| Gestational age (weeks) | 25.9 ± 1.3 | 0.2 | 26.4 ± 1.1 | | | |
| Range | 24.1-28.0 | | 24.6-28.0 | | | |
|  | n = 38 | | n = 29 | | | |
| $4^{th}$ blood sampling (28.1-32 weeks) | | | | | | |
| Soluble Endoglin (ng/ml) | 3.7 ± 1.1 | <0.001* | 10.2 ± 9.8 | 0.01* | 96.1 ± 25.7 | 0.05 |
| Gestational age (weeks) | 29.9 ± 1.1 | 1.0 | 30.2 ± 1.0 | 1.0 | 30.4 ± 1.4 | 1.0 |
| Range | 28.3-32.0 | | 28.7-32.0 | | 29.4-31.4 | |
|  | n = 42 | | n = 33 | | n = $2^\delta$ | |
| $5^{th}$ blood sampling (32.1-36.9 weeks) | | | | | | |
| Soluble Endoglin (ng/ml) | 5.79 ± 2.42 | 0.003* | 10.51 ± 6.59 | <0.00 | 43.14 ± 25.6 | <0.00 |
| Gestational age (weeks) | 34.7 ± 1.3 | 1.0 | 34.8 ± 1.5 | 1* | 34.5 ± 1.2 | 1* |
| Range | 32.4-36.6 | | 32.6-36.7 | 1.0 | 32.6-36.6 | 1.0 |
|  | n = 37 | | n = 20 | | n = 13 | |
| $6^{th}$ blood sampling (>=37 weeks) | | | | | | |
| Soluble Endoglin (ng/ml) | 8.9 ± 4.5 | | — | | 15.23 ± 10.61 | 0.006 |
| Gestational age (weeks) | 39.4 ± 1.0 | | | | 38.8 ± 1.1 | * |
| Range | 37.0-40.7 | | | | 37.6-41.4 | 0.05 |
|  | n = 27 | | | | n = 27 | |

$p^\beta$: compared between samples at clinical manifestation of pre-eclampsia and normal pregnancy Value expressed as mean ± sd $^\delta$2 pre-eclamptic patients had no blood samples available at clinical manifestation

TABLE 5

Plasma soluble endoglin concentrations in normal and pre-eclamptic pregnant women.

| Blood sampling | Normal pregnancy | Pre-eclampsia | p |
|---|---|---|---|
| *At clinical manifestation* | | | |
| Soluble Endoglin (ng/ml) | 7.63 ± 4.22 | 27.72 ± 26.20 | <0.001* |
| Gestational age (weeks) | 37.2 ± 3.0 | 37.1 ± 2.7 | 0.9 |
| Range | 28.9-40.7 | 29.4-41.4 | |
|  | n = 42 | n = 42[δ] | |
| *2-5.9 weeks before clinical manifestation* | | | |
| Soluble Endoglin (ng/ml) | 4.67 ± 2.32 | 15.07 ± 10.15 | <0.001* |
| Gestational age (weeks) | 31.6 ± 3.8 | 32.8 ± 2.8 | 0.2 |
| Range | 24.1-36.3 | 27.1-36.7 | |
|  | n = 27 | n = 27 | |
| Interval before clinical manifestation (weeks) |  | 3.8 ± 1.1 | |
| *6-10.9 weeks before clinical manifestation* | | | |
| Soluble Endoglin (ng/ml) | 3.61 ± 1.05 | 5.89 ± 3.07 | <0.001* |
| Gestational age (weeks) | 28.5 ± 2.9 | 28.5 ± 2.9 | 0.9 |
| Range | 19.7-32.6 | 19.6-34.4 | |
|  | n = 37 | n = 37 | |
| Interval before clinical manifestation (weeks) |  | 8.3 ± 1.4 | |
| *11-15.9 weeks before clinical manifestation* | | | |
| Soluble Endoglin (ng/ml) | 3.35 ± 0.77 | 3.57 ± 0.92 | 0.5 |
| Gestational age (weeks) | 24.5 ± 3.1 | 24.2 ± 3.3 | 0.8 |
| Range | 17.6-27.9 | 17.7-28.0 | |
|  | n = 19 | n = 19 | |
| Interval before clinical manifestation (weeks) |  | 13.2 ± 1.3 | |
| *16-25 weeks before clinical manifestation* | | | |
| Soluble Endoglin (ng/ml) | 3.44 ± 1.07 | 3.69 ± 1.18 | 0.3 |
| Gestational age (weeks) | 17.6 ± 3.5 | 16.5 ± 4.5 | 0.2 |
| Range | 9.1-23.4 | 8.0-22.7 | |
|  | n = 42 | n = 42 | |
| Interval before clinical manifestation (weeks) |  | 20.6 ± 3.6 | |

Value expressed as mean ± sd
[δ]2 pre-eclamptic patients had no blood samples available at clinical manifestation To examine the diagnostic potential of plasma soluble endoglin concentrations to identify those destined to develop pre-eclampsia, patients were stratified into early onset pre-eclampsia (PE<34 weeks) and late onset pre-eclampsia (PE>34 weeks). For patients with early-onset pre-eclampsia, the mean plasma soluble endoglin levels was significantly higher in pre-eclampsia (before clinical diagnosis) than in normal pregnancy starting around 16-24 weeks of gestation (Table 6) with very dramatic differences in 24-28 week and 28-32 week gestational windows. In contrast, for patients with late-onset pre-eclampsia, plasma soluble endoglin concentrations in pre-clinical pre-eclampsia was significantly higher than in normal pregnancy only at 28-32 weeks with very dramatic differences at 32-36 week of gestation (Table 7).

TABLE 6

Plasma soluble endoglin concentrations in normal pregnant women and patients who developed clinical Pre-eclampsia at 34 weeks of gestation or less.

|  | Normal pregnancy | p | Pre-clinical samples Pre-eclampsia | p | Clinical samples pre-eclampsia[δ] | p[β] |
|---|---|---|---|---|---|---|
| *1st blood sampling (7.1-16 weeks)* | | | | | | |
| Soluble Endoglin (ng/ml) | 3.89 ± .928 | 0.7 | 3.81 ± 1.11 | | | |
| Gestational age (weeks) | 12.3 ± 2.2 | 0.4 | 11.6 ± 2.6 | | | |
| Range | 8.4-15.9 |  | 8.0-15.1 | | | |
|  | n = 37 |  | n = 8 | | | |
| *2nd blood sampling (16.1-24 weeks)* | | | | | | |
| Soluble Endoglin (ng/ml) | 3.36 ± 1.11 | 0.02* | 4.60 ± 1.72 | | | |
| Gestational age (weeks) | 19.4 ± 1.7 | 0.7 | 19.8 ± 2.9 | | | |
| Range | 16.3-23.4 |  | 17.3-23.9 | | | |
|  | n = 44 |  | n = 7 | | | |
| *3rd blood sampling (24.1-28 weeks)* | | | | | | |
| Soluble Endoglin (ng/ml) | 3.189 ± .729 | 0.001* | 10.22 ± 6.17 | | | |
| Gestational age (weeks) | 25.9 ± 1.3 | 0.03* | 26.8 ± 0.6 | | | |
| Range | 24.1-28.0 |  | 26.0-27.3 | | | |
|  | n = 38 |  | n = 6 | | | |
| *4th blood sampling (28.1-32 weeks)* | | | | | | |
| Soluble Endoglin (ng/ml) | 3.70 ± 1.10 | 0.01* | 17.66 ± 8.9 | 0.008* | 96.10 ± 25.76 | 0.05 |
| Gestational age (weeks) | 29.9 ± 1.1 | 1.0 | 29.7 ± 1.1 | 1.0 | 30.4 ± 1.4 | 1.0 |
| Range | 28.3-32.0 |  | 28.7-31.3 |  | 29.4-31.4 | |
|  | n = 42 |  | n = 6 |  | n = 2[δ] | |

TABLE 6-continued

Plasma soluble endoglin concentrations in normal pregnant women and patients who developed clinical Pre-eclampsia at 34 weeks of gestation or less.

|  | Normal pregnancy | p | Pre-clinical samples Pre-eclampsia | p | Clinical samples pre-eclampsia[b] | p[β] |
|---|---|---|---|---|---|---|
| | | | 5th blood sampling (32.1-36.9 weeks) | | | |
| Soluble Endoglin (ng/ml) | 5.79 ± 2.42 | | | | 53.38 ± 32.09 | 0.001* |
| Gestational age (weeks) | 34.7 ± 1.3 | | | | 33.5 ± 0.5 | <0.001* |
| Range | 32.4-36.6 | | | | 32.6-34.0 | |
| | n = 37 | | | | n = 6 | | p[β]: compared between samples at clinical manifestation of pre-eclampsia and normal pregnancy Value expressed as mean ± sd

[b]2 pre-eclamptic patients had no blood samples available at clinical manifestation

TABLE 7

Plasma soluble endoglin concentrations in normal pregnant women and pre-eclamptics (34 weeks of gestation)

|  | Normal pregnancy | p | Pre-clinical samples Pre-eclampsia | p | Clinical samples Pre-eclampsia | p[β] |
|---|---|---|---|---|---|---|
| | | | 1st blood sampling (7.1-16 weeks) | | | |
| Soluble Endoglin (ng/ml) | 3.89 ± .928 | 0.9 | 4.01 ± 1.35 | | | |
| Gestational age (weeks) | 12.3 ± 2.2 | 0.2 | 11.6 ± 2.4 | | | |
| Range | 8.4-15.9 | | 7.7-15.1 | | | |
| | n = 37 | | n = 26 | | | |
| | | | 2nd blood sampling (16.1-24 weeks) | | | |
| Soluble Endoglin (ng/ml) | 3.36 ± 1.11 | 0.4 | 3.59 ± 1.23 | | | |
| Gestational age (weeks) | 19.4 ± 1.7 | 0.04* | 20.3 ± 1.9 | | | |
| Range | 16.3-23.4 | | 16.7-24.0 | | | |
| | n = 44 | | n = 29 | | | |
| | | | 3rd blood sampling (24.1-28 weeks) | | | |
| Soluble Endoglin (ng/ml) | 3.18 ± .729 | 0.1 | 3.98 ± 2.13 | | | |
| Gestational age (weeks) | 25.9 ± 1.3 | 0.4 | 26.3 ± 1.1 | | | |
| Range | 24.1-28.0 | | 24.6-28.0 | | | |
| | n = 38 | | n = 23 | | | |
| | | | 4th blood sampling (28.1-32 weeks) | | | |
| Soluble Endoglin (ng/ml) | 3.70 ± 1.10 | 0.001* | 8.57 ± 9.45 | | | |
| Gestational age (weeks) | 29.9 ± 1.1 | 0.2 | 30.3 ± 1.0 | | | |
| Range | 28.3-32.0 | | 28.7-32.0 | | | |
| | n = 42 | | n = 27 | | | |
| | | | 5th blood sampling (32.1-36.9 weeks) | | | |
| Soluble Endoglin (ng/ml) | 5.79 ± 2.42 | <0.001* | 10.51 ± 6.59 | 0.001* | 34.36 ± 16.30 | <0.001* |
| Gestational age (weeks) | 34.7 ± 1.3 | 1.0 | 34.8 ± 1.5 | 0.9 | 35.4 ± 0.9 | 0.7 |
| Range | 32.4-36.6 | | 32.6-36.7 | | 34.3-36.6 | |
| | n = 37 | | n = 20 | | n = 7 | |
| | | | 6th blood sampling (>=37 weeks) | | | |
| Soluble Endoglin (ng/ml) | 8.98 ± 45.12 | | — | | 15.23 ± 10.61 | 0.006* |
| Gestational age (weeks) | 39.4 ± 1.0 | | | | 38.8 ± 1.1 | 0.05 |
| Range | 37.0-40.7 | | | | 37.6-41.4 | |
| | n = 27 | | | | n = 27 | | p[β]: compared between samples at clinical manifestation of pre-eclampsia and normal pregnancy Value expressed as mean ± sd Summary The results of these experiments demonstrate that women with clinical pre-eclampsia have very high levels of circulating soluble endoglin when compared to gestational age matched controls. The results also demonstrate that women destined to develop pre-eclampsia (pre-clinical pre-eclampsia) have higher plasma soluble endoglin levels than those who are predicted to have a normal pregnancy. The increase in soluble endoglin levels is detectable at least 6-10 weeks prior to onset of clinical symptoms. Finally, these results demonstrate that both early onset and late onset pre-eclampsia have elevated circulating soluble endoglin concentrations, but the alterations are more dramatic in the early onset pre-eclampsia.

Example 6

Soluble Endoglin Protein Levels as a Diagnostic Indicator of Pre-Eclampsia and Eclampsia in Women (CPEP Study)

As described above, we have discovered that soluble endoglin, a cell surface receptor for the pro-angiogenic protein TGF-β and expressed on endothelium and syncytiotrophoblast, is upregulated in pre-eclamptic placentas. In the experiments described above, we have shown that in pre-eclampsia excess soluble endoglin is released from the placenta into the circulation through shedding of the extracellular domain; soluble endoglin may then synergize with sFlt1, an anti-angiogenic factor which binds placental growth factor (PlGF) and VEGF, to cause endothelial dysfunction. To test this hypothesis, we compared serum concentrations of soluble endoglin, sFlt1, and free PlGF throughout pregnancy in women who developed pre-eclampsia and in those women with other pregnancy complication such as gestational hypertension (GH) and pregnancies complicated by small-for-gestational (SGA) infants to those of women with normotensive control pregnancies. This study was done in collaboration with the Dr. Richard Levine at the NIH.

There were two principal objectives of this study. The first objective was to determine whether, in comparison with normotensive controls, elevated serum concentrations of soluble endoglin, sFlt1, and reduced levels of PlGF can be detected before the onset of pre-eclampsia and other gestational disorders such as gestational hypertension or pregnancies complicated by small-for-gestational (SGA) infants. The second objective was to describe the time course of maternal serum concentrations of soluble endoglin, sFlt-1, and free PlGF with respect to gestational age in women with pre-eclampsia, gestational hypertension, or SGA with separate examination of specimens obtained before and after onset of clinical symptoms, and in normotensive controls.

Methods

Clinical Information

This study was a case control study of pregnancy complications (premature pre-eclampsia, term pre-eclampsia, gestational hypertension, pregnancies with SGA infants, normotensive control pregnancies) nested within the cohort of 4,589 healthy nulliparous women who participated in the Calcium for Pre-eclampsia Prevention trial (CPEP). 120 random cases were selected from each of the study groups. The study methods were identical to the nested case control study recently performed for pre-eclampsia (Levine et al, *N. Eng. J. Med.* 2004, 350:672-83). From each woman blood specimens were obtained before study enrollment (13-21 wks), at 26-29 weeks, at 36 weeks, and on suspicion of hypertension or proteinuria. All serum specimens collected at any time during pregnancy before onset of labor and delivery were eligible for the study. Cases included 120 women who developed term pre-eclampsia, gestational hypertension, or SGA and who delivered a liveborn or stillborn male baby without known major structural or chromosomal abnormalities, and from whom a baseline serum specimen was obtained. For premature pre-eclampsia, defined as (PE<37 weeks) all 72 patients from the CPEP cohort were studied. The clinical criterion for the diagnosis of pre-eclampsia is described in Levine et al., (2004), supra. All cases of gestational hypertension were required to have a normal urine protein measurement within the interval from 1 day prior to onset of gestational hypertension through 7 days following. SGA was defined as <10th and <5th (severe SGA) percentile, using Zhang & Bowes' tables of birthweight for gestational age, specific for race, nulliparity, and infant gender. Controls were randomly selected from women without pre-eclampsia or gestational hypertension or SGA who delivered a liveborn or stillborn baby without known major structural malformations or chromosomal anomalies and matched, one control to one case, by the clinical center, gestational age at collection of the first serum specimen (±1 wk), by freezer storage time (±1 year), and by number of freeze-thaws. A total of 1674 serum specimens were studied. Matching by gestational age was done to control for gestational age-related differences in levels of sFlt-1, VEGF, and PlGF. Matching for freezer storage time was done to minimize differences due to possible degradation during freezer storage. Matching by clinical center was done to control for the fact that pre-eclampsia rates differed significantly between centers, perhaps due to differences in the pathophysiology of the disease. In addition, the centers may have used slightly different procedures for collecting, preparing, and storing specimens. Matching by number of thaws was also performed to ensure that cases and controls will have been subjected equally to freeze thaw degradation.

ELISA Measurements

ELISA for the various angiogenic markers were performed at the Karumanchi laboratory by a single research assistant that was blinded to the clinical outcomes.

Commercially available ELISA kits for soluble endoglin (DNDG00), sFlt1 (DVR100), PlGF (DPG00) were obtained from R&D systems, (Minneapolis, Minn.).

Statistical Analysis

T-test was used for the comparison of the various measurements after logarithmic transformation to determine significance. $P<0.05$ was considered as statistically significant.

Results

Figure 6:
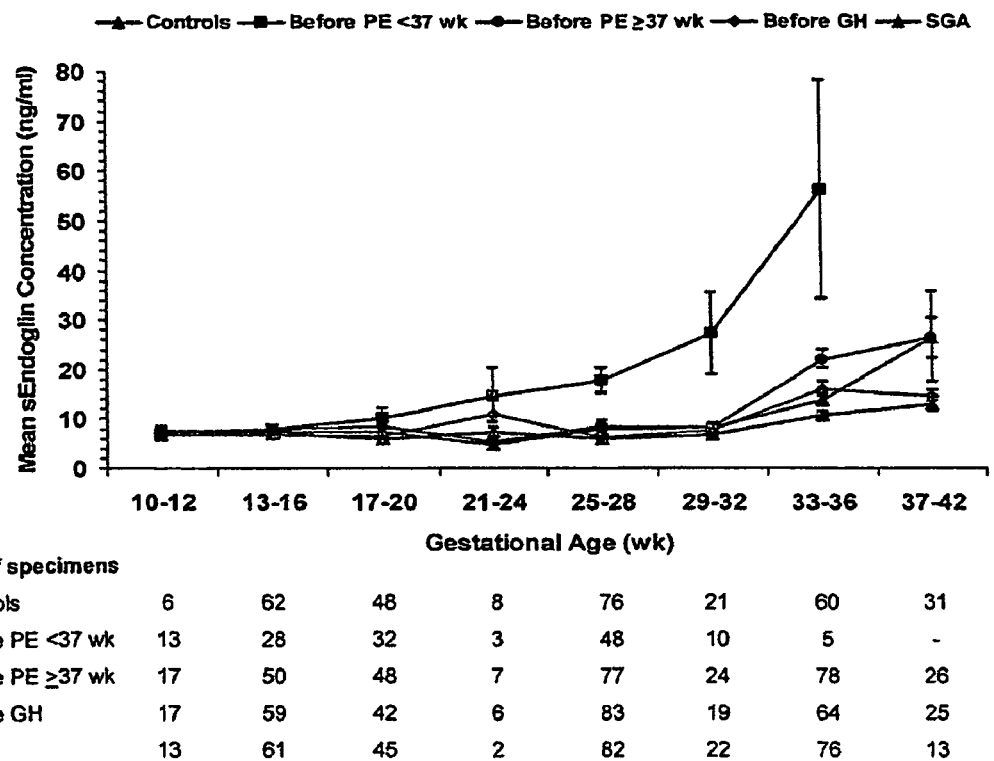
FIG. 6 is a graph showing the mean soluble endoglin concentration for the five different study groups of pregnant women throughout pregnancy during the various gestational age group windows.
Figure 7:
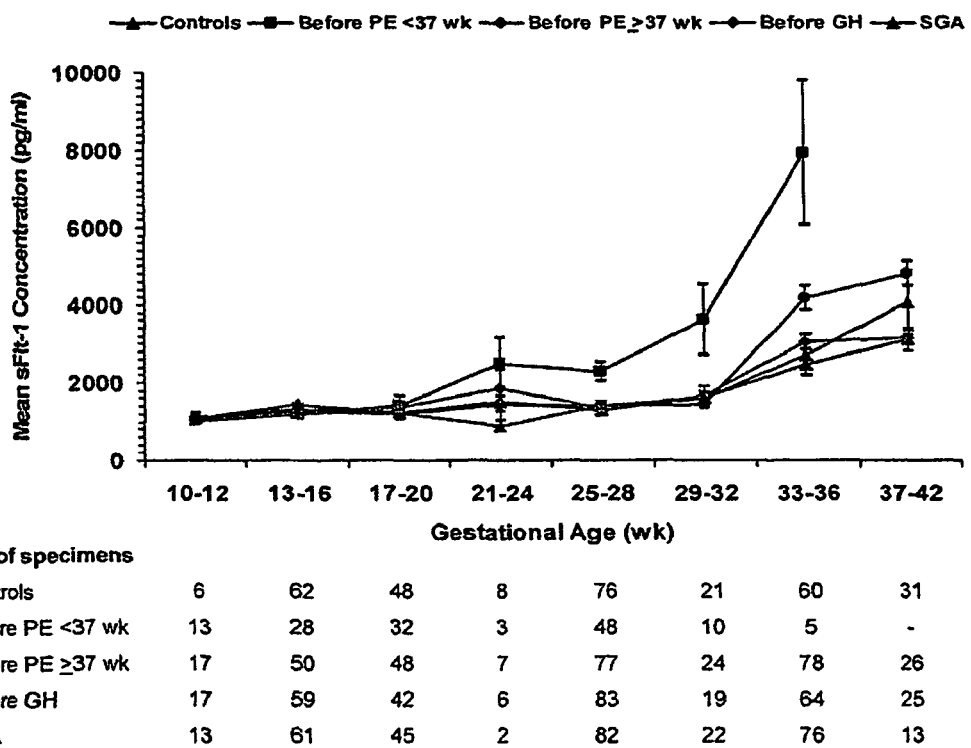
FIG. 7 is a graph showing the mean sFlt1 concentrations for the five different study groups of pregnant women throughout pregnancy during the various gestational age group windows.
Figure 8:
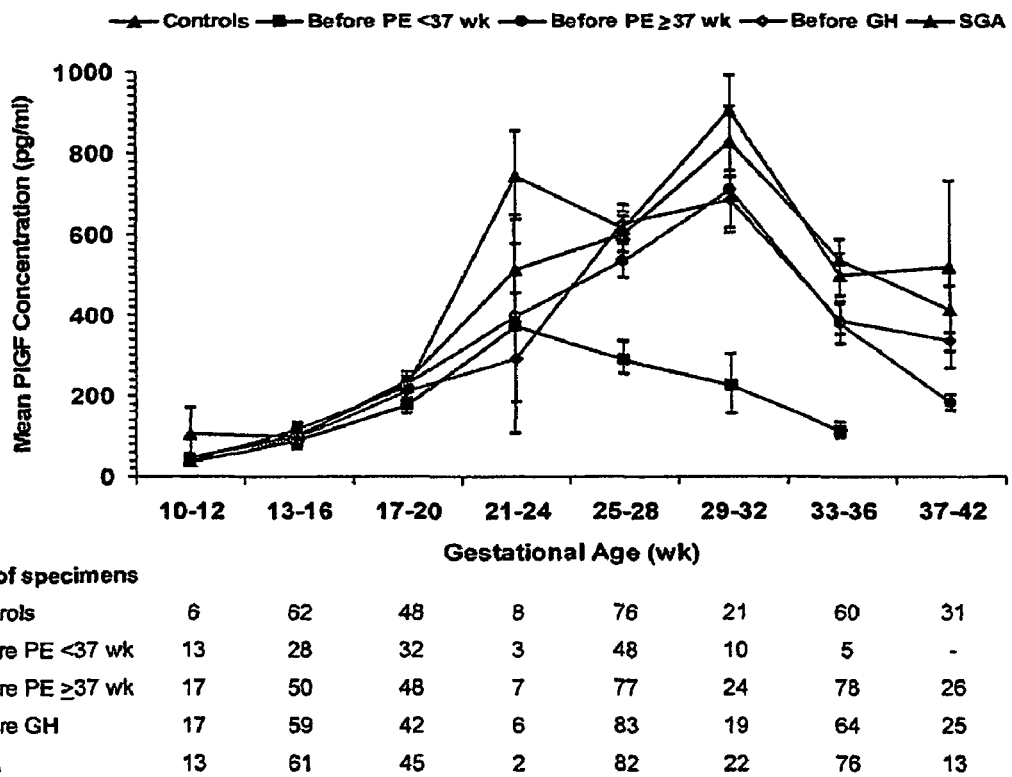
FIG. 8 is a graph showing the mean PlGF concentrations for the five different study groups of pregnant women throughout pregnancy during the various gestational age group windows.

The mean soluble endoglin (FIG. 6), sFlt1 (FIG. 7) and PlGF (FIG. 8) concentrations for the five different study groups of pregnant women throughout pregnancy during the various gestational age group windows as described in the methods are shown in FIGS. 6-8. For the pre-eclampsia groups and gestational hypertensive groups, specimens taken after onset of clinical symptoms are not shown here. Compared with gestational age-matched control specimens, soluble endoglin and sFlt1 increased and free PlGF decreased beginning 9-11 weeks before preterm pre-eclampsia, reaching levels 5-fold (46.4 vs 9.8 ng/ml, P<0.0001) and 3-fold higher (6356 vs 2316 pg/ml, P<0.0001) and 4-fold lower (144 vs 546 pg/ml, P<0.0001), respectively, after pre-eclampsia onset. For term pre-eclampsia, soluble endoglin increased beginning 12-14 weeks, free PlGF decreased beginning 9-11 weeks, and sFlt1 increased <5 weeks before pre-eclampsia onset. Serum concentrations of sFlt1 and free PlGF did not differ significantly between pregnancies with SGA or average for gestation age/large for gestation age (AGA/LGA) infants from 10-42 weeks of gestation. Serum soluble endoglin was modestly increased in SGA pregnancies beginning at 17-20 weeks (7.2 vs 5.8 ng/ml, P=0.03), attaining concentrations of 15.7 and 43.7 ng/ml at 37-42 weeks for mild and severe SGA, respectively, as compared with 12.9 ng/ml in AGA/LGA pregnancies (severe SGA vs AGA/LGA, P=0.002). In the gestational hypertension study, compared with GA-matched control specimens, modest increases in soluble endoglin were apparent <1-5 weeks before gestational hypertension, reaching levels 2-fold higher for soluble endoglin (29.7 vs 12.5 ng/ml, P=0.002) after onset of gestational hypertension. The adjusted odds ratio for subsequent preterm PE for specimens obtained at 21-32 weeks which were in the highest quartile of control soluble endoglin concentrations (>7.2 ng/ml), as compared to all other quartiles, was 9.8 (95% CI 4.5-21.5).

Figure 9:
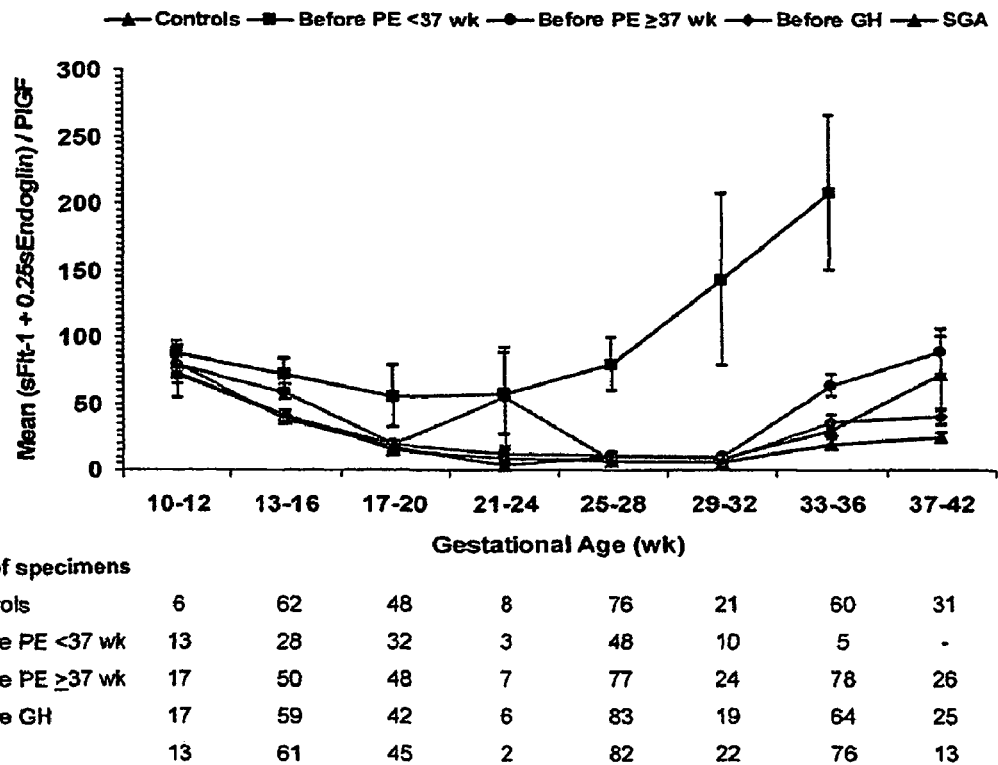
FIG. 9 is a graph showing the values for the soluble endoglin anti-angiogenic index for pre-eclampsia anti-angiogenesis for samples taken prior to clinical symptoms.

The soluble endoglin anti-angiogenic index for pre-eclampsia was defined as (sFlt1+0.25 soluble endoglin)/PlGF. The index was calculated throughout the various gestational age groups for the five different study groups. The soluble endoglin anti-angiogenic index for pre-eclampsia anti-angiogenesis for samples taken prior to clinical symptoms is shown in FIG. 9. Elevated values for the soluble endoglin anti-angiogenic index were noted as early as 17-20 weeks of pregnancies and seemed to get more dramatic with advancing gestation in severe pre-mature pre-eclampsia. In term pre-eclampsia, SGA and GH, there was a modest elevation during the end of pregnancy (33-36 weeks) when compared to control women.

Figure 10:
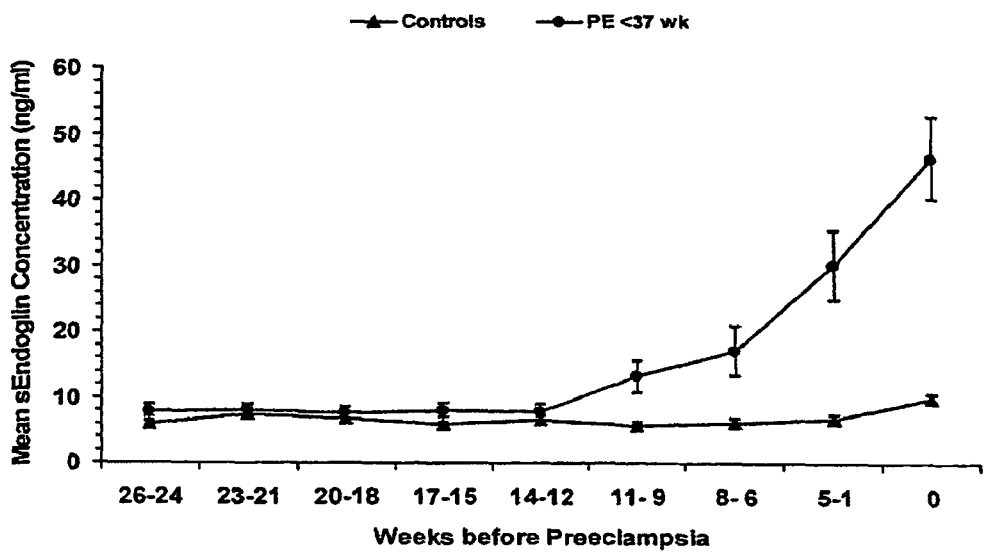
FIG. 10 is a graph showing the mean concentrations of soluble endoglin according to the number of weeks before clinical premature pre-eclampsia (PE<37 weeks).
Figure 11:
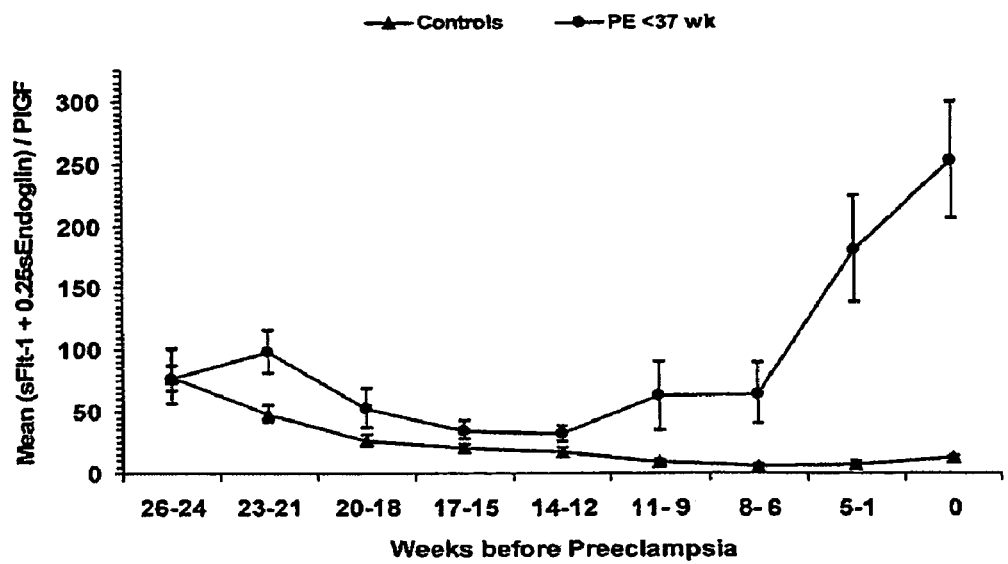
FIG. 11 is a graph showing the soluble endoglin anti-angiogenic index values according to the number of weeks before clinical premature pre-eclampsia (PE<37 weeks).

FIGS. 10 and 11 depict the mean concentrations of soluble endoglin (FIG. 10) and soluble endoglin anti-angiogenic index (FIG. 11) according to the number of weeks before clinical premature pre-eclampsia (PE<37 weeks). Even as early 9-11 weeks prior to the onset of premature pre-eclampsia, there was a 2-3 fold elevation in soluble endoglin and soluble endoglin anti-angiogenic index in women destined to develop pre-eclampsia with dramatic elevations (>5 fold) in 1-5 weeks preceding clinical symptoms.

Figure 12:
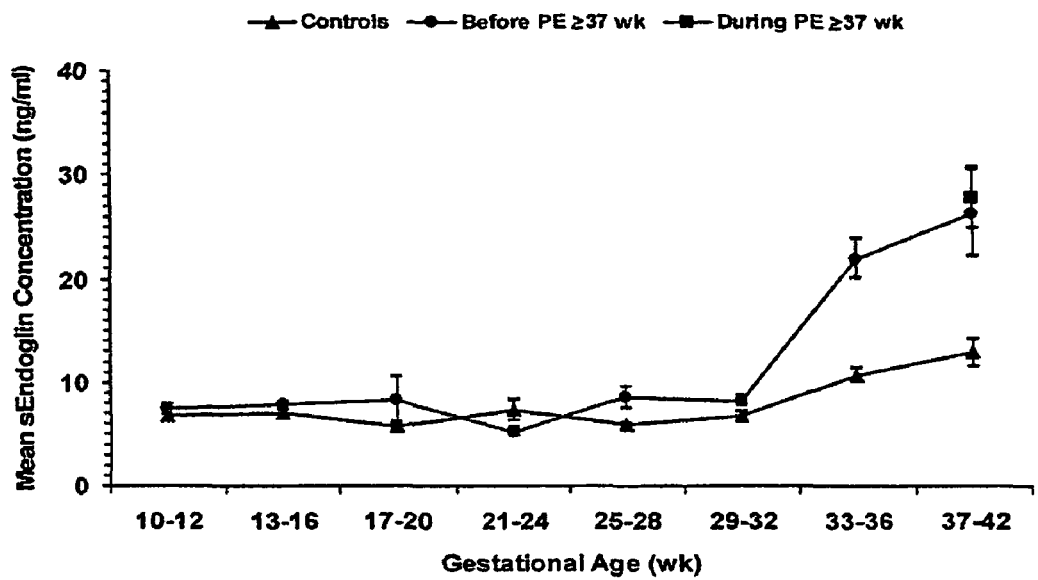
FIG. 12 is a graph showing the alteration in soluble endoglin levels throughout pregnancy for term pre-eclampsia (PE>37 weeks) before and after symptoms.
Figure 13:
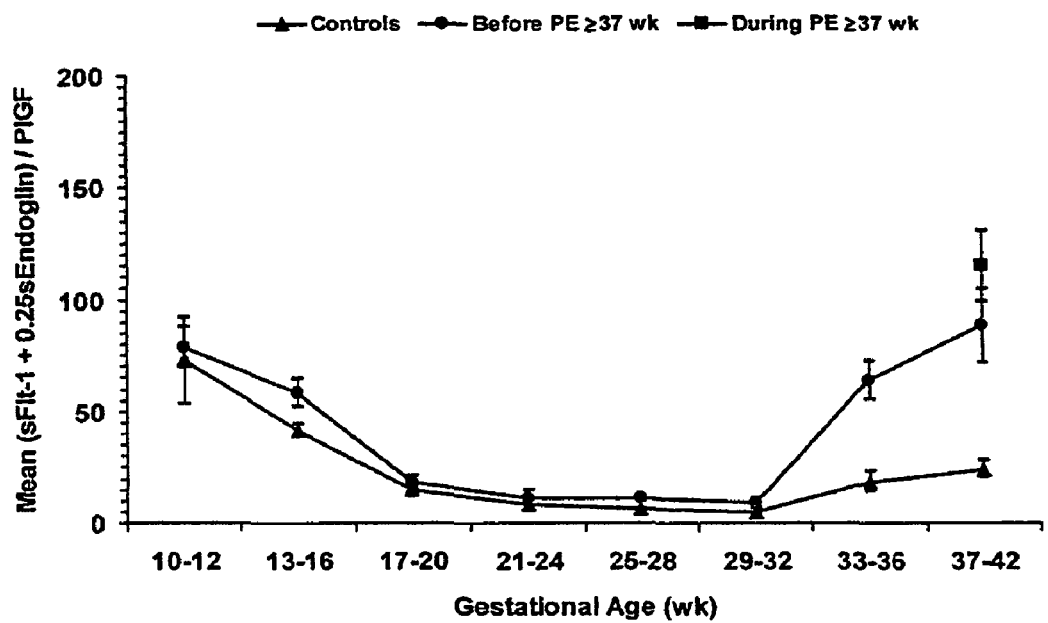
FIG. 13 is a graph showing the alteration in the soluble endoglin anti-angiogenic index levels throughout pregnancy for term pre-eclampsia (PE>37 weeks) before and after symptoms.

FIGS. 12 and 13 show the alteration in soluble endoglin (FIG. 12) and the soluble endoglin anti-angiogenic index (FIG. 13) throughout pregnancy for term pre-eclampsia (PE>37 weeks) before and after symptoms. Elevation in soluble endoglin and the soluble endoglin anti-angiogenic index are noted starting at 33-36 weeks of pregnancy reaching on average 2-fold higher levels at the time of clinical pre-eclampsia.

Figure 14:
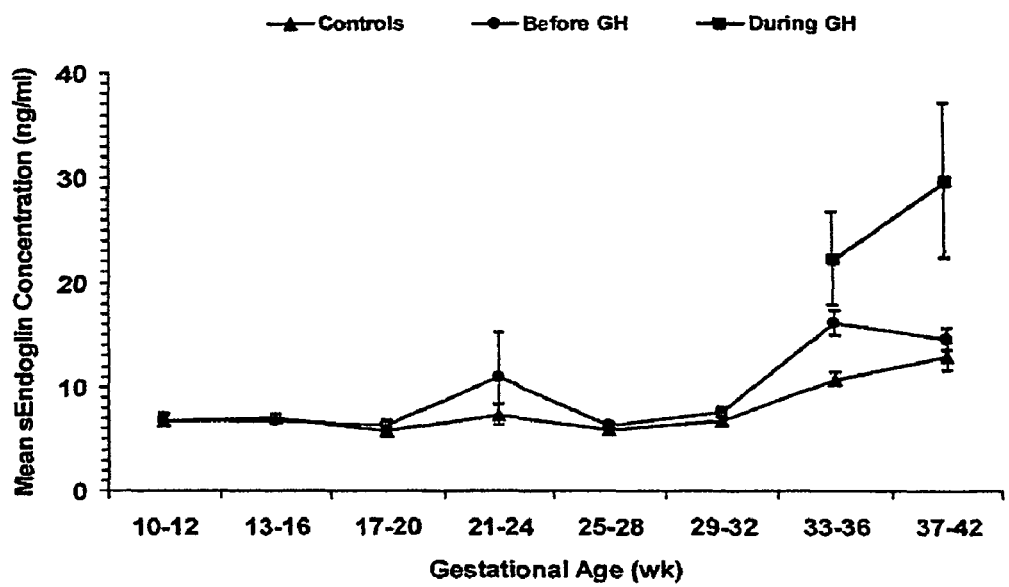
FIG. 14 is a graph showing the soluble endoglin levels detected in women during gestational hypertension and before gestational hypertension (1-5 weeks preceding gestational hypertension (during weeks 33-36 of pregnancy)) and normotensive controls.
Figure 15:
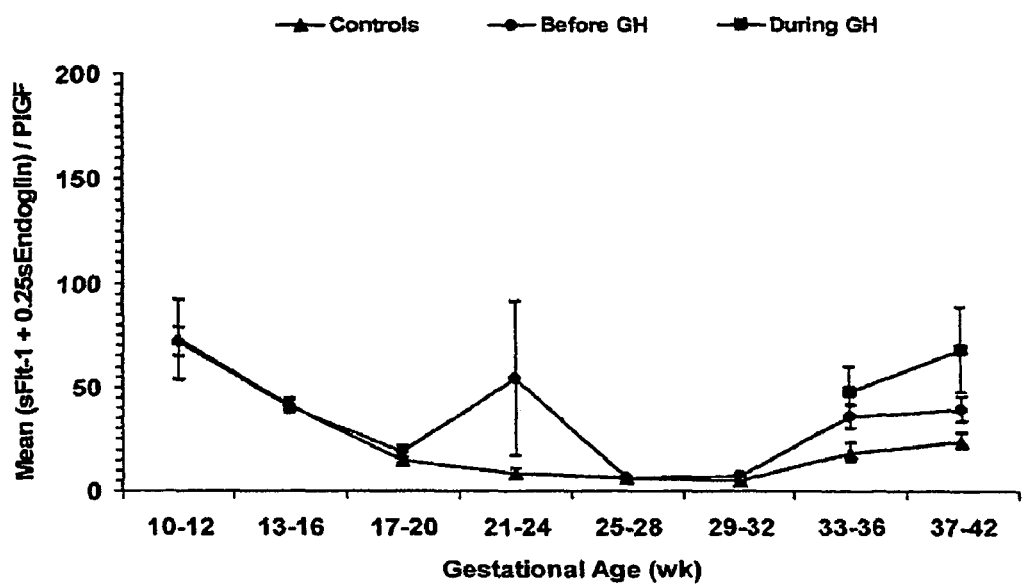
FIG. 15 is a graph showing the soluble endoglin anti-angiogenic index levels in women during gestational hypertension and before gestational hypertension (1-5 weeks preceding gestational hypertension (during weeks 33-36 of pregnancy)) and normotensive controls.

FIGS. 14 and 15 show a modest elevation in soluble endoglin (FIG. 14) and the soluble endoglin anti-angiogenic index (FIG. 15) detected in women during gestational hypertension, and 1-5 weeks preceding gestational hypertension (during 33-36 week of pregnancy) when compared to normotensive controls.

Figure 16:
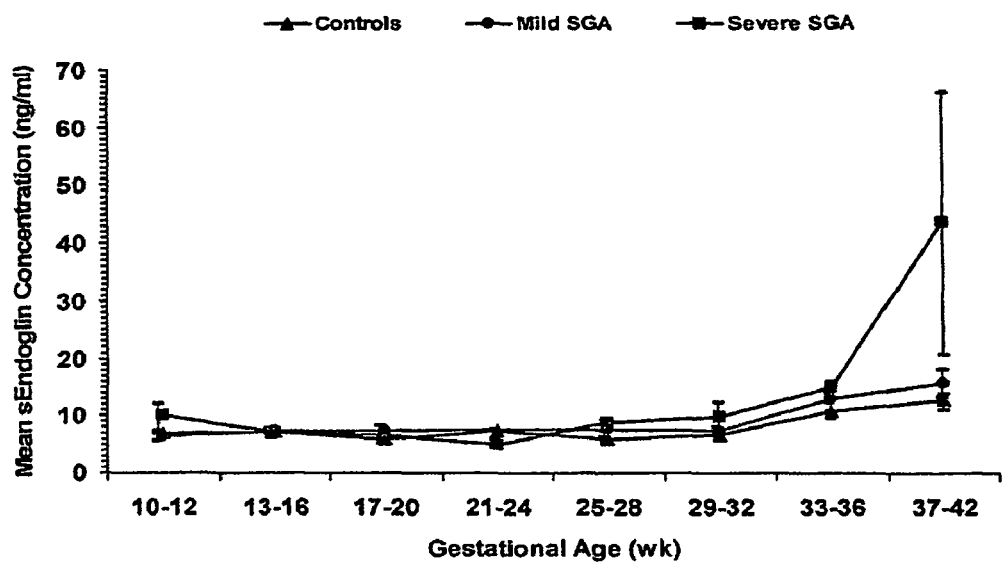
FIG. 16 is a graph showing the soluble endoglin levels detected during the 33-36 week gestational windows in women with severe SGA, mild SGA, and normotensive controls.
Figure 17:
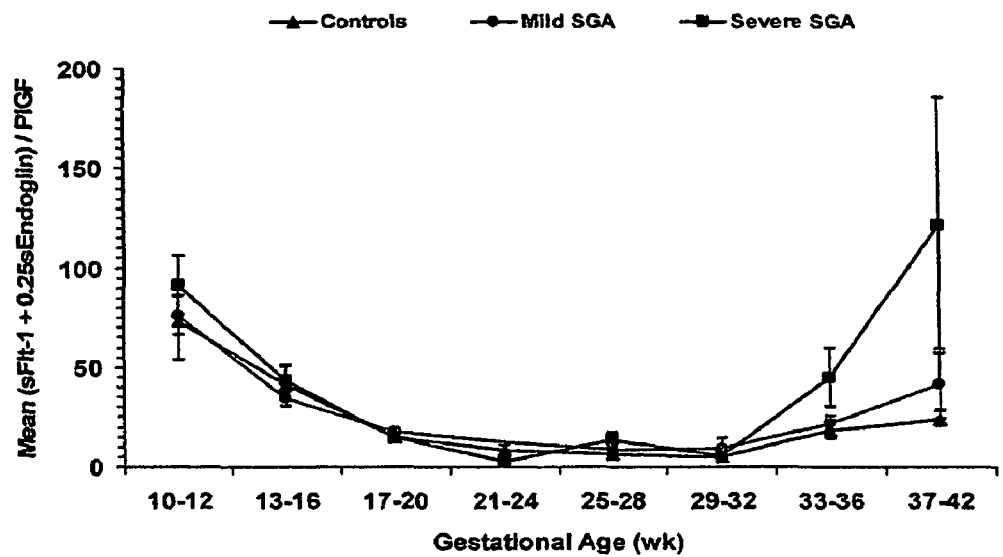
FIG. 17 is a graph showing the soluble endoglin anti-angiogenic index levels detected during the 33-36 week gestational windows in women with severe SGA, mild SGA, and normotensive controls.

FIGS. 16 and 17 show a modest elevations in soluble endoglin (FIG. 16) and the soluble endoglin anti-angiogenic index (FIG. 17) detected during the 33-36 week gestational windows in women with severe SGA and not in all women with SGA when compared to control pregnancies.

Summary

The results of this study show that the soluble endoglin levels and soluble endoglin anti-angiogenic index levels, when measured prior to 33 weeks of pregnancy, was dramatically elevated in women destined to develop premature pre-eclampsia and in women with clinical premature pre-eclampsia (PE<37 weeks) when compared to normal control pregnancy. Therefore, soluble endoglin levels and soluble endoglin anti-angiogenic index levels (prior to 33 weeks) can not only be used for the diagnosis of premature pre-eclampsia, but also for the prediction of pre-eclampsia. It appears that elevations in soluble endoglin levels and soluble endoglin anti-angiogenic index levels start as early as 10-12 weeks prior to symptoms of pre-eclampsia.

The soluble endoglin levels and soluble endoglin anti-angiogenic index levels were also significantly elevated in term pre-eclampsia (PE>37 weeks) and modestly elevated in gestational hypertension and severe SGA when measured late in pregnancy (33-36 week gestational windows). Therefore, soluble endoglin levels and soluble endoglin anti-angiogenic index levels can also be used to identify other pregnancy complications such as SGA and gestation hypertension when measured after 33 weeks of pregnancy.

Example 7

Involvement of Soluble Endoglin in the Pathogenesis of Pre-Eclampsia

We have shown that endoglin, a cell surface receptor for the pro-angiogenic protein TGF-β and expressed on endothelium and syncytiotrophoblast, is upregulated in pre-eclamptic placentas. We have also shown that in pre-eclampsia, excess soluble endoglin is released from the placenta into the circulation through shedding of the extracellular domain. The experiments described below were designed to test the hypothesis that soluble endoling may synergize with sFlt1, an anti-angiogenic factor which binds placental growth factor (PlGF) and VEGF, to cause endothelial dysfunction.

Materials and Methods

Reagents

Recombinant Human endoglin, human sFlt1, mouse endoglin, mouse sFlt1, human TGF-β1, human TGF-β3, mouse VEGF were obtained from R&D systems (Minneapolis, Minn.). Mouse monoclonal antibody (catalog #sc 20072) and polyclonal antibody (sc 20632) against the N-terminal region of human endoglin was obtained from Santa Cruz Biotechnology, Inc. ELISA kits for human sFlt1, mouse sFlt1 and human soluble endoglin were obtained from R&D systems, MN.

Generation of Adenoviruses

Adenoviruses against sFlt1 and control adenovirus (CMV) have been previously described (Maynard et al, *J. Clin. Invest.* 111: 649:658 (2003)) and were generated at the Harvard Medical Core facility in collaboration with Dr. Richard Mulligan. To create the soluble endoglin adenovirus, we used the Adeasy Kit (Stratagene). Briefly, human soluble endoglin (encoding the entire extracellular region of the endoglin protein) was PCR amplified using human cDNA full length endoglin clone (Invitrogen, CA) as the template and the following oligonucleotides as primers: forward 5'-ACG AAG CTT GAA ACA GTC CAT TGT GAC CTT-3' (SEQ ID NO: 3) and reverse 5'TTA GAT ATC TGG CCT TTG CTT GTG CAA CC-3' (SEQ ID NO: 4). Amplified PCR fragments were initially subcloned into pSecTag2-B (Invitrogen, CA) and the DNA sequence was confirmed. A mammalian expression construct encoding His-tagged human soluble endoglin was PCR amplified using pSecTag2 B-soluble endoglin as the template and subcloned into pShuttle-CMV vector (Stratagene; Kpn1 and Sca1 sites), an adenovirus transfer vector, for adenovirus generation. Adenovirus expressing soluble endoglin (sE) was then generated using the standard protocol per manufacturer instructions and confirmed for expression by western blotting. The confirmed clone was then amplified on 293 cells and purified on a CsCl2 density gradient as previously described (Kuo et al, *Proc. Natl. Acad. Sci. USA* 98:4605-4610 (2001)). The final products were titered by an optical absorbance method (Sweeney et al, *Virology,* 2002, 295:284-288). The titer is expressed as plaque forming units (pfu)/mL based on a formula derived from previous virus preps that were titered using the standard plaque dilution based titration assay kit (BD Biosciences Clontech, Palo Alto, Calif., Cat. No. K1653-1) and the optical absorbance method.

Western Blots

Western blots were used for checking the expression of adenoviral-infected transgenes in the rat plasma as described elsewhere (Maynard et al, supra).

Immunoprecipitation (IP) Experiments

IP followed by western blots were used to identify and characterize soluble endoglin in the placental tissue and serum specimens from patients with pre-eclampsia. Human placental tissue was washed with cold PBS and lysed in homogenization buffer [10 mM Tris-HCl, pH 7.4; 15 mM NaCl; 60 mM KCl; 1 mM EDTA; 0.1 mM EGTA; 0.5% Nonidet P-40; 5% sucrose; protease mixture from Roche (Indianapolis, Ind.)] for 10 minutes. Placental lysates were then subjected to immunoprecipitation with an anti-human monoclonal mouse endoglin antibody (Santa Cruz Biotechnology, Inc., Santa Cruz, Calif.). Immunoaffinity columns were prepared by the directional coupling of 3-5 mg of the purified antibody to 2 ml protein A-Sepharose using an immunopure IgG orientation kit (Pierce Chemical Co., Rockford, Ill., USA) according to the manufacturer's instructions. Columns were then washed extensively with RIPA buffer containing protease mixture, and bound proteins were eluted with 0.1 mol/L glycine-HCl buffer, pH 2.8. The eluent was collected in 0.5-ml fractions containing 1 mol/L Tris-HCl buffer. Protein-containing fractions were pooled and concentrated 9- to 10-fold with CENTRICON Centrifugal Concentrator (Millipore Corp., Bedford, Mass., USA). The immunoprecipitated samples were separated on a 4-12% gradient gel (Invitrogen) and proteins were transferred to polyvinylidene difluoride (PVDF) membranes. Endoglin protein was detected by western blots using rabbit polyclonal antibody to human endoglin (Santa Cruz Biotechnology, Inc., Santa Cruz, Calif.).

Endothelial Tube Assay

Growth factor reduced matrigel (7 mg/mL, Collaborative Biomedical Products, Bedford, Mass.) was placed in wells (100l/well) of a pre-chilled 48-well cell culture plate and incubated at 37° C. for 30 minutes to allow polymerization. HUVEC cells (30,000+in 300 µl of endothelial basal medium with no serum, Clonetics, Walkersville, Md.) were treated with various combinations of recombinant protein (soluble endoglin, sFlt1, or both) and plated onto the Matrigel coated wells, and incubated at 37° C. for 12-16 hours. Tube formation was then assessed through an inverted phase contrast microscope at 4× (Nikon Corporation, Tokyo, Japan) and quantitatively analyzed (tube area and total length) using the Simple PCI imaging analysis software.

Microvascular Permeability Experiments

Balb-C mice were injected through the retro-orbital venous plexus with $1\times10^8$ pfu of adenovirus expressing GFP or soluble endoglin or sFlt1 or combinations and microvascular permeability assay was performed 48 hours later. Mice were anesthetized by IP injection of 0.5 ml Avertin. 100 ml of 1% Evans blue dye (in PBS) was injected into the tail vein. 40 minutes later, mice were perfused via heart puncture with PBS containing 2 mM EDTA for 20 minutes. Organs (brain, lung, liver, kidney) were harvested and incubated in formamide for 3 days to elute Evans blue dye. OD of formamide solution was measured using 620 nm wave length.

Renal Microvascular Reactivity Experiments

Microvascular reactivity experiments were done as described previously (Maynard et al., supra) using rat renal microvessels (70-170 µm internal diameter). In all experimental groups, the relaxation responses of kidney microvessels were examined after pre-contraction of the microvessels with U46619 (thromboxane agonist) to 40-60% of their baseline diameter at a distending pressure of 40 mmHg. Once the steady-state tone was reached, the responses to various reagents such as TGF-β1 or TGF-β3 or VEGF were examined in a standardized order. All drugs were applied extraluminally.

Animal Models

Both pregnant and non-pregnant Sprague-Dawley rats were injected with $2\times10^9$ pfu of adenoviruses (Ad CMV or Ad sFlt1 or Ad sE or Ad sFlt1+Ad sE) by tail vein injections. Pregnant rats were injected at day 8-9 of pregnancy (early second trimester) and blood pressure measured at day 16-17 of pregnancy (early third trimester). Blood pressures were measured in the rats after anesthesia with pentobarbital sodium (60 mg/kg, i.p.). The carotid artery was isolated and cannulated with a 3-Fr high-fidelity microtip catheter connected to a pressure transducer (Millar Instruments, Houston, Tex.). Blood pressure was recorded and averaged over a 10-minute period. Blood, tissue and urine samples were then obtained before euthanasia. Plasma levels were measured on the day of blood pressure measurement (day 8 after injection of the adenoviruses), recognizing that 7-10 days after adenoviral injection corresponds to the peak level of expression of these proteins. Circulating sFlt-1 and soluble endoglin levels were confirmed initially by western blotting and then quantified using commercially available murine ELISA kits (R & D Systems, Minneapolis, Minn.). Urinary albumin was measured both by both standard dipstick and quantified by competitive enzyme-linked immunoassay using a commercially available rat albumin ELISA kit (Nephrat kit, Exocell Inc, Philadelphia, Pa.). Urinary creatinine was measured by a picric acid colorimetric procedure kit (Metra creatinine assay kit, Quidel Corp, San Diego, Calif.). AST and LDH were measured using the commercially available kits (Thermo Electron, Louisville, Colo.). Platelet counts from rat blood were measured using an automated hemocytometer (Hemavet 850, Drew Scientific Inc, Oxford, Conn.). A peripheral smear of the blood with Wright's stain was performed for the detection of schistocytes in circulating blood. After the measurement of blood pressure and collection of specimens, the rats were sacrificed and organs harvested for histology. The litter was counted and individual placentas and fetuses weighed. Harvested kidneys were placed in Bouin's solution, paraffin embedded, sectioned and stained with H&E, PAS or Masson's trichrome stain.

Statistical Comparisons

Results are presented as mean±standard error of mean (SEM) and comparisons between multiple groups were made by analysis of variance using ANOVA. Significant differences are reported when $p<0.05$.

Results

Figure 22:
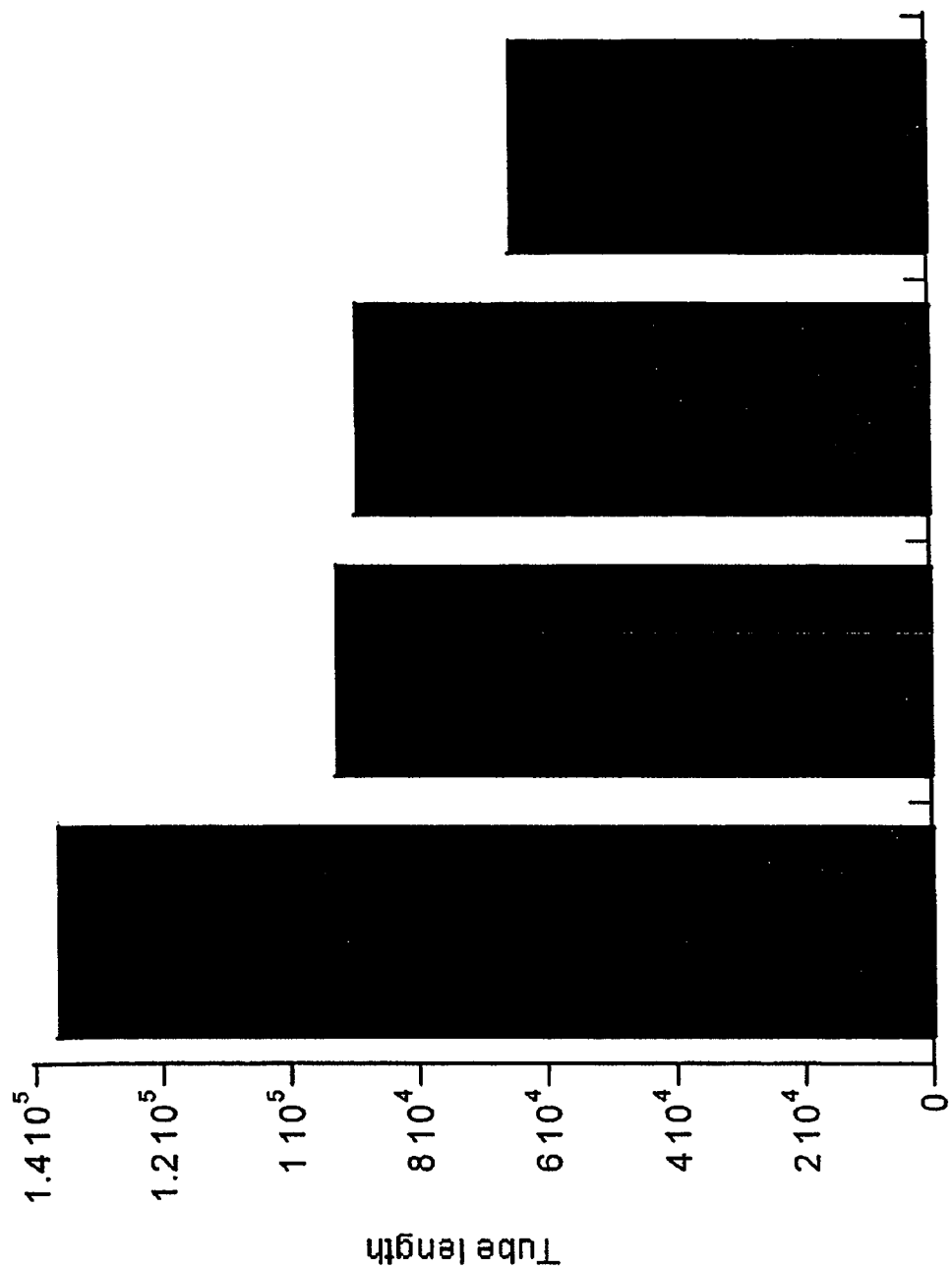
FIG. 22 is a graph showing the results of angiogenesis assays using HUVECs in growth factor reduced matrigels. Angiogenesis assays were performed in the presence of soluble endoglin or sFlt1 or both and the endothelial tube lengths quantitated. C—represents control, E—represents 1 µg/ml of soluble endoglin and S represents 1 µg/ml of sFlt1. E+S represent the combination of 1 µg/ml of E+1 µg/ml of sFlt1. Data represents a mean of three independent experiments.
Figure 23:
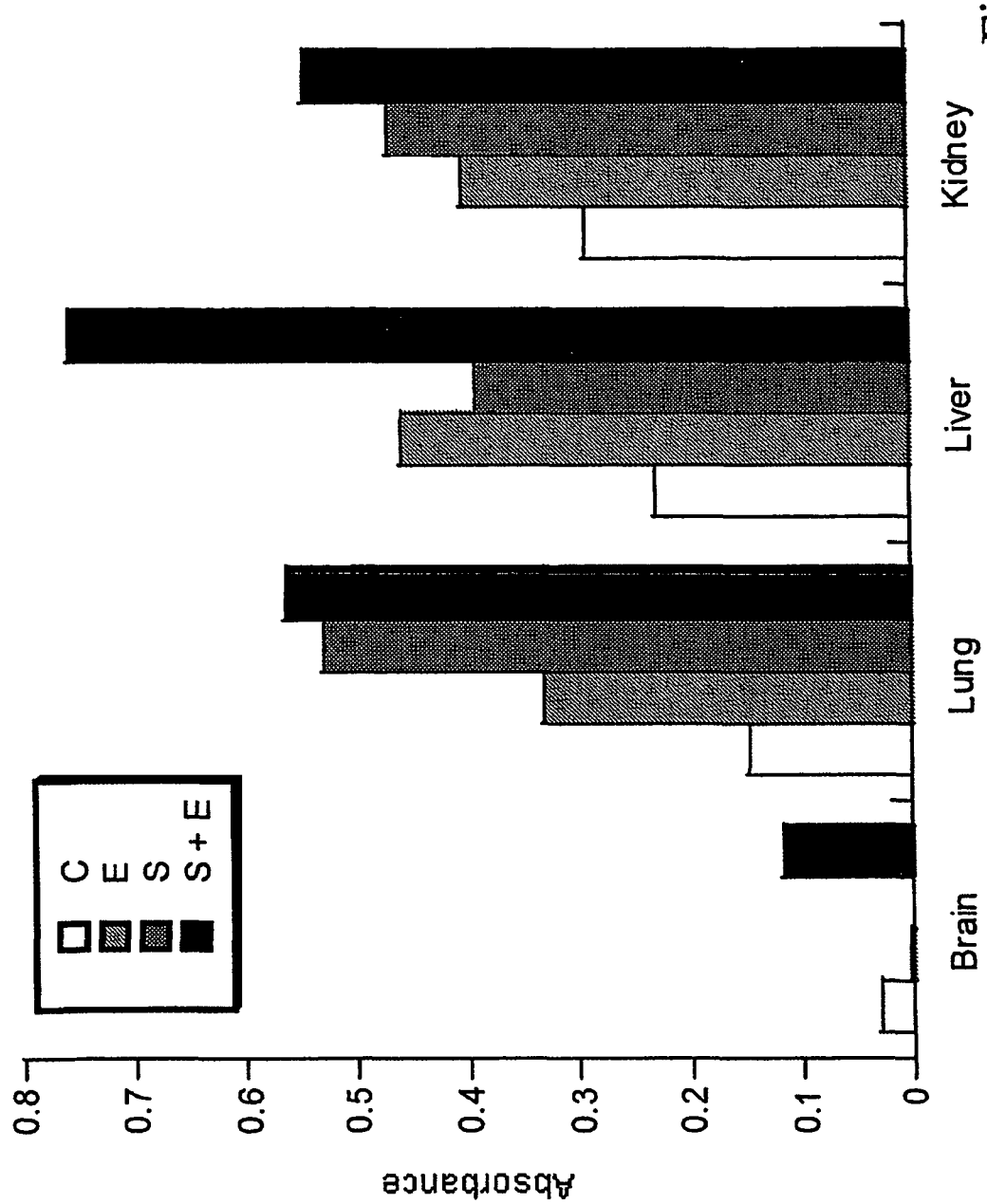
FIG. 23 is a graph showing the microvascular permeability in several organ beds assessed using Evans blue leakage in mice as described in the materials and methods. C-control (GFP), E-soluble endoglin, S-sFlt1 and S+E-sFlt1+ soluble endoglin. Data represents a mean of 4 independent experiments.

Soluble Endoglin is an Anti-Angiogenic Molecule and Induces Vascular Dysfunction We used an in vitro model of angiogenesis to understand the function of the soluble endoglin. Soluble endoglin modestly inhibits endothelial tube formation, that is further enhanced by the presence of sFlt1 (FIG. 22 and FIG. 31). In pre-eclampsia, it has been reported that in addition to endothelial dysfunction, there is also enhanced microvascular permeability as evidenced by edema and enhanced leakage of Evan's blue bound albumin extracellularly. In order to see if soluble endoglin induces microvascular leak, we used mice treated for 48 hours with soluble endoglin and sFlt adenoviruses. A combination of soluble endoglin and sFlt1 induced a dramatic increase in albumin leakage in the lungs, liver and the kidney and a modest leakage in the brain as demonstrated using Evan's blue assay (FIG. 23). Soluble endoglin alone induced a modest leakage in the liver. Importantly, the combination of soluble endoglin and sFlt-1 showed an additive effect in the liver, indicating that these soluble receptors may act in concert to disrupt endothelial integrity and induce significant vascular damage and leak. These data suggest that soluble endoglin and sFlt1 combination are potent anti-angiogenic molecules and can induce significant vascular leakage.

Figure 24:
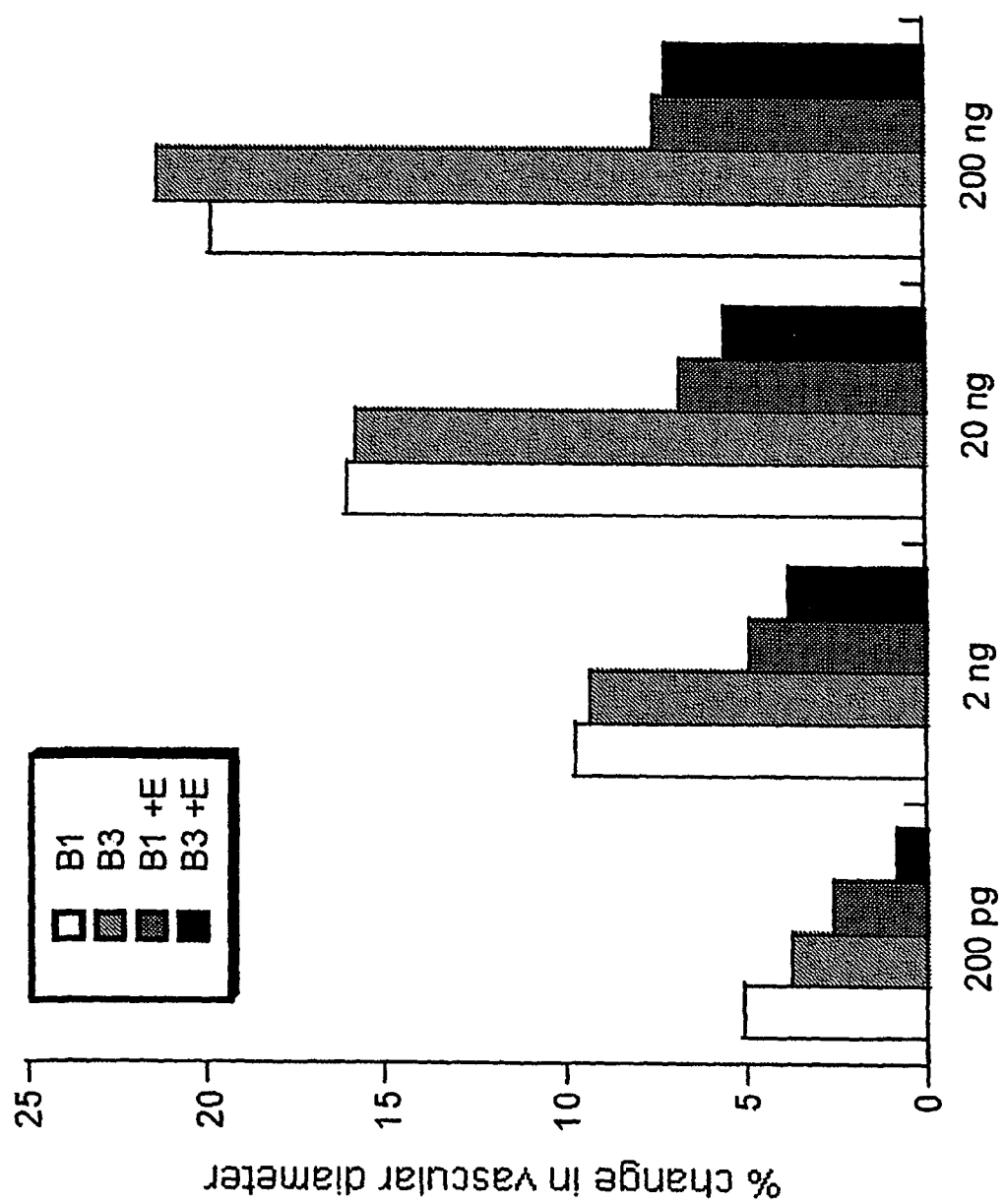
FIG. 24 is a graph showing the percent change in rat renal microvessel diameter when subjected to microvascular reactivity experiments in the presence of TGF-β1 (B1) and TGF-β3 (B3) from doses ranging from 200 pg/ml-200 ng/ml. These same experiments were repeated in the presence of soluble endoglin (E) at 1 µg/ml. These data presented are a mean of 4 independent experiments.
Figure 25:
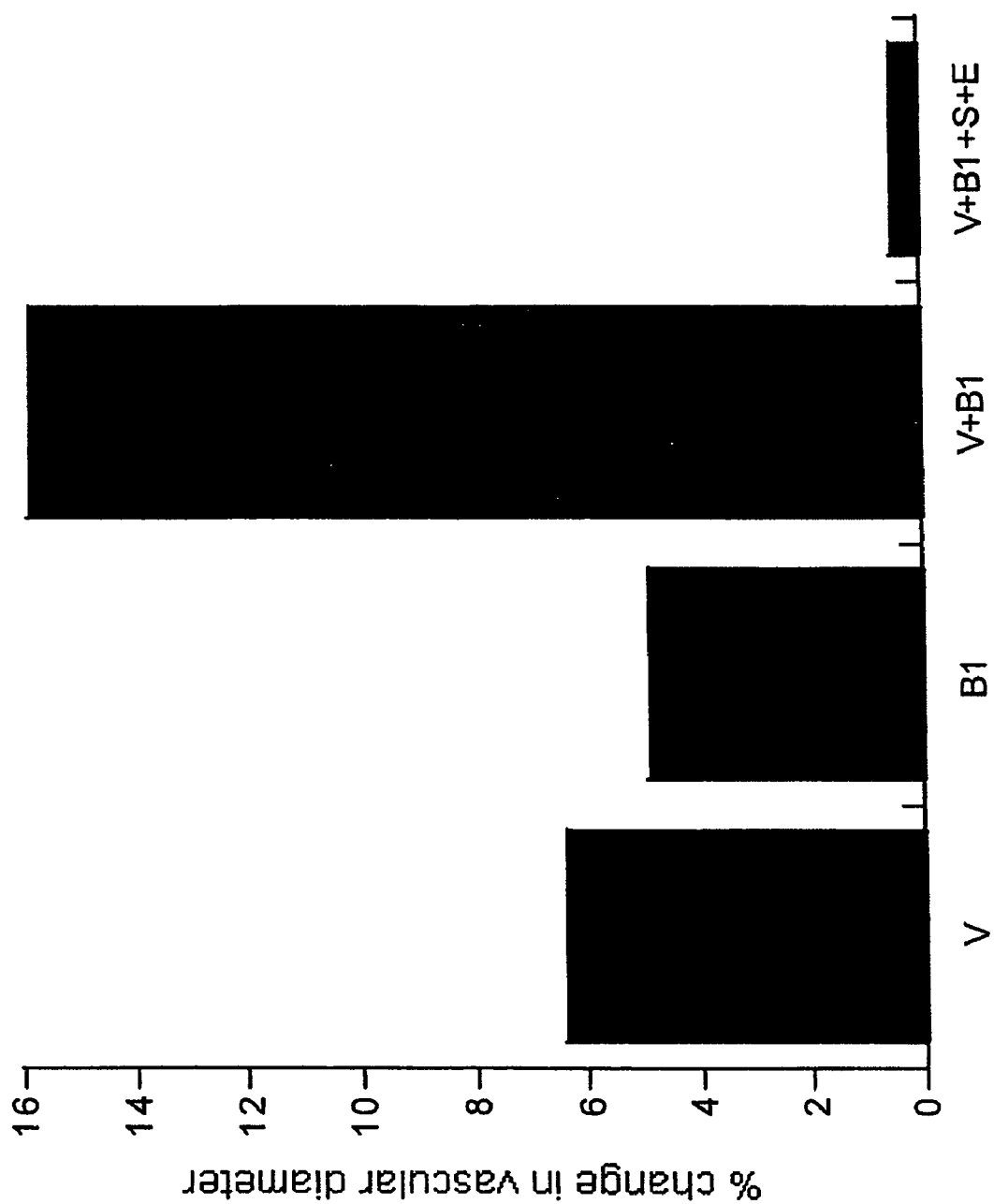
FIG. 25 is a graph showing the percent change in the vascular diameter of renal microvessels in the presence of 1 ng/ml of VEGF (V), TGF-β1 (B1) and the combination (V+B1). Also shown is the effect of this combination in the presence of 1 µg/ml each of sFlt1 (S) and soluble endoglin (E) (V+B1+S+E). The data represents a mean of 4 independent experiments.
Figure 32:
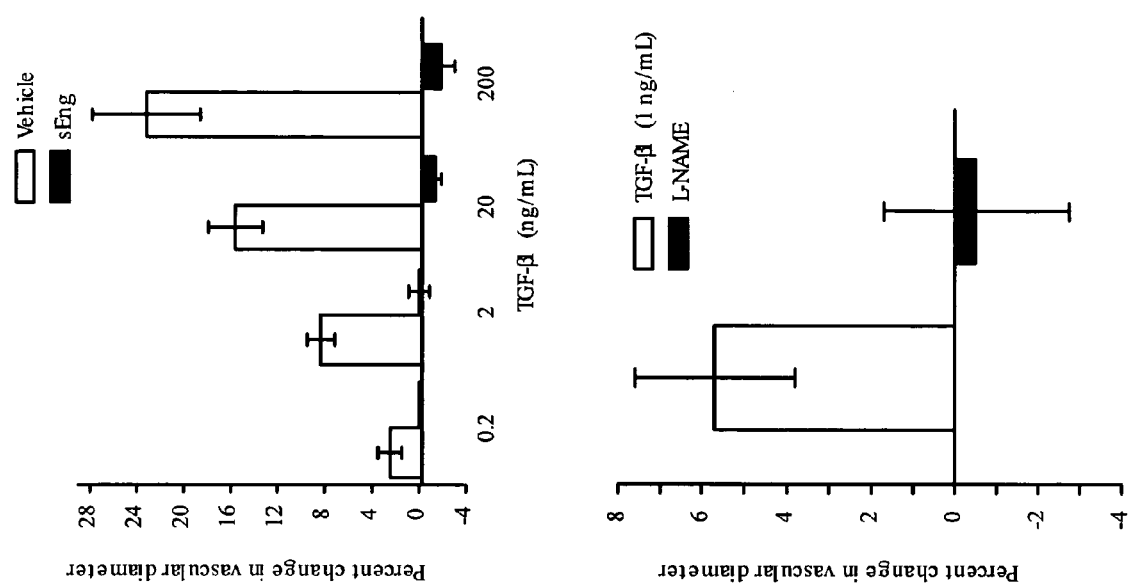
FIG. 32 is a series of graphs showing inhibition of TGF-β1-mediated vascular reactivity in mesenteric vessels by soluble endoglin. Microvascular reactivity of rat mesenteric microvessels was measured in the presence of TGF-β1 or TGF-β3 from 200 pg/ml to 200 ng/ml. The experiments were repeated in the presence of recombinant soluble endoglin at 1 μg/ml. The mean±SE of 4 independent experiments is shown (upper panel). Also shown is the blocking effect of L-NAME on TGFβ1 at 1 ng/ml (lower panel).
Figure 33:
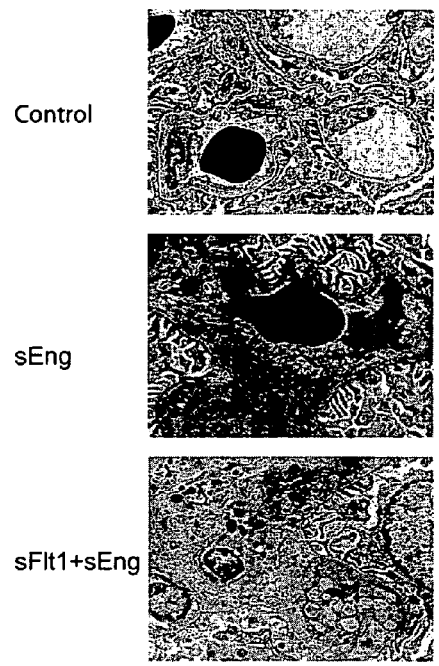
FIG. 33 is a series of photomicrographs showing glomerular endotheliosis in pregnant rats. Electron micrographs (EM) of glomeruli from a control pregnant rat (upper panel), soluble endoglin (sEng)-treated pregnant rat (middle panel) and the combination group—soluble endoglin (sEng)+sFlt1 (lower panel) are shown. These photos were taken at 6200× (original magnification) for the upper and middle panel and 5000× (original magnification) for the lower panel.
Figure 34:
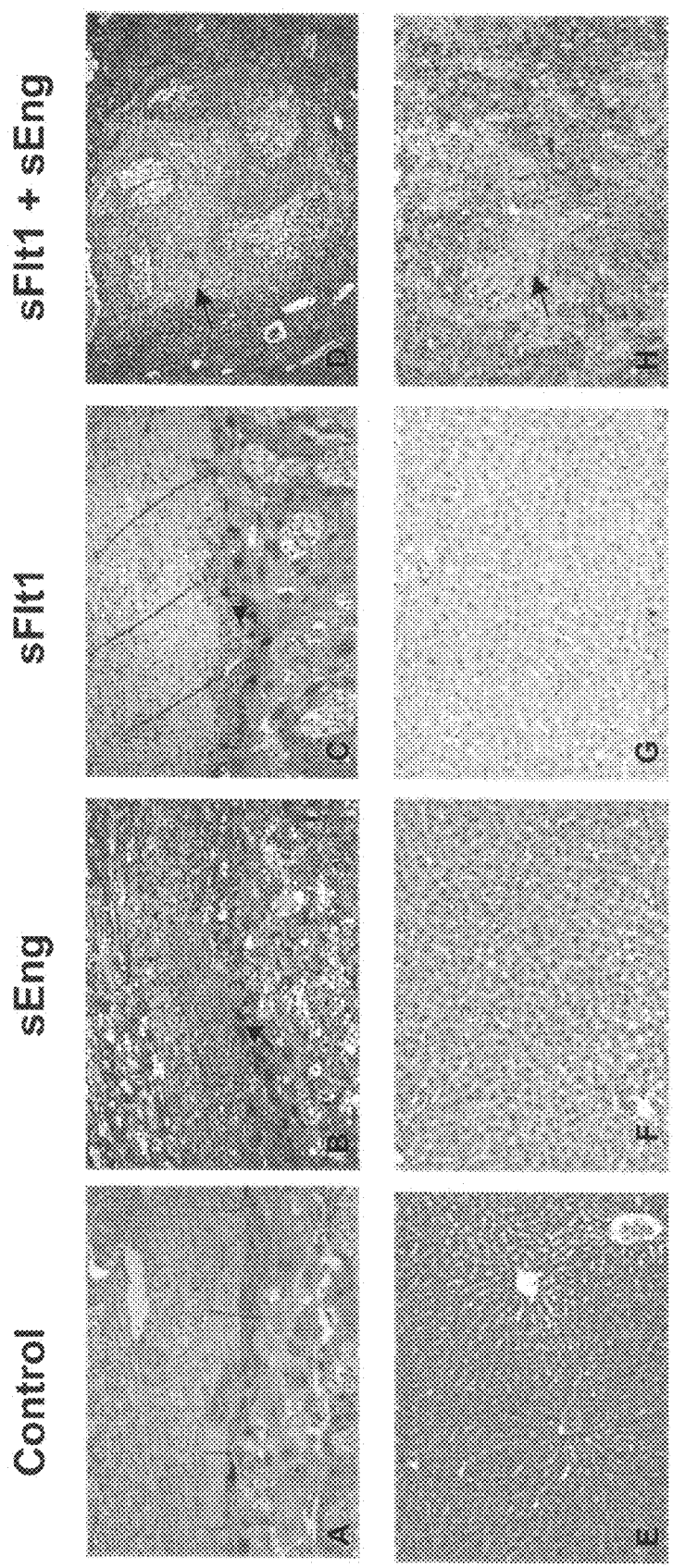
FIGS. 34A-H are a series of photomicrographs showing renal, placental and hepatic histological changes and peripheral blood smears in pregnant rats after soluble endoglin and sFlt1 treatment. Placental histology (H &E stain) of control (FIG. 34A), sEng (FIG. 34B), sFlt1 (FIG. 34C) and sFlt1+sEng (FIG. 34D) groups. Both the soluble endoglin and sFlt1 treated animals show diffuse inflammation (arrow heads) at the maternal-fetal junction not seen in controls. There is hemorrhagic infarction and fibrinoid necrosis with lumen obstruction of a maternal vessel (arrow) in the decidua of the sFlt1+sEng treated placenta (FIG. 34D). Scale bar, 200 μm (FIG. 34E-H). Liver histology in the control (FIG. 34E), sEng (FIG. 34F), sFlt1 (FIG. 34G) and sFlt1+sEng (FIG. 34H) groups. Ischemic changes with multifocal necrosis (arrow head) are noted in the sFlt1+sEng group (FIG. 34H). Control group and rats given sEng or sFlt1 showed no changes. Scale bar, 200 μm.

To assess the hemodynamic effects of soluble endoglin, a series of microvascular reactivity experiments in rat renal microvessels were performed. We studied first the effects of TGF-β1 and TGF-β3-two known ligands of endoglin. Both TGF-β1 and TGF-β3 induced a dose-dependent increase in vascular diameter. Both TGF-β1 and β3 induced a dose-dependent increase in arterial diameter, whereas, TGF-β2, which is not a ligand for endoglin, failed to produce any significant vasodilation (<2% at 0.1 and 1 μg/ml). Importantly in the presence of excess soluble endoglin, the effect of both the TGF-βs were significantly attenuated (FIG. 24). This acute effect of TGF-β1 and TGF-β3 isoforms on vascular tone was also seen in mesenteric vessels (FIG. 32). Finally, the combination of VEGF and TGF-β1 induced vasodilation which was blocked by excess soluble endoglin and sFlt1 (FIG. 25). This suggests that the sFlt1 and soluble endoglin may oppose the physiological vasodilation induced by angiogenic growth factors such as VEGF and TGF-β1 and induce hypertension.

In Vivo Effects of Soluble Endoglin and sFlt1

In order to assess the vascular effects of soluble endoglin and sFlt1, we resorted to adenoviral expression system in pregnant rats. Adenovirus encoding a control gene (CMV) or soluble endoglin or sFlt1 or sFlt1+soluble endoglin were injected by tail vein on day 8 of pregnancy in Sprague Dawley rats. On day 17, animals were examined for pre-eclampsia phenotype. Table 8 includes the hemodynamic and biochemical data.

TABLE 8

Hemodynamic and biochemical data for adenovirus treated rat animal models.

| Groups | N | MAP in mm Hg | Urine Alb/creat μg/mg | Platelet count × 1000/μl | LDH U/L | AST U/L | Fetal weight in gms |
|---|---|---|---|---|---|---|---|
| Control (CMV) | 4 | 86.33 | 84.17 | 1378 | 257 | 43 | 4.56 |
| sFlt1 | 4 | 134* | 3478.3* | 1247 | 324 | 78 | 3.55 |
| sE | 4 | 112* | 366.90 | 1406 | 463 | 95 | 3.20 |
| sFlt1 + sE | 4 | 145* | 6478.2* | 538* | 1428* | 187* | 2.50* |

Figure 36:
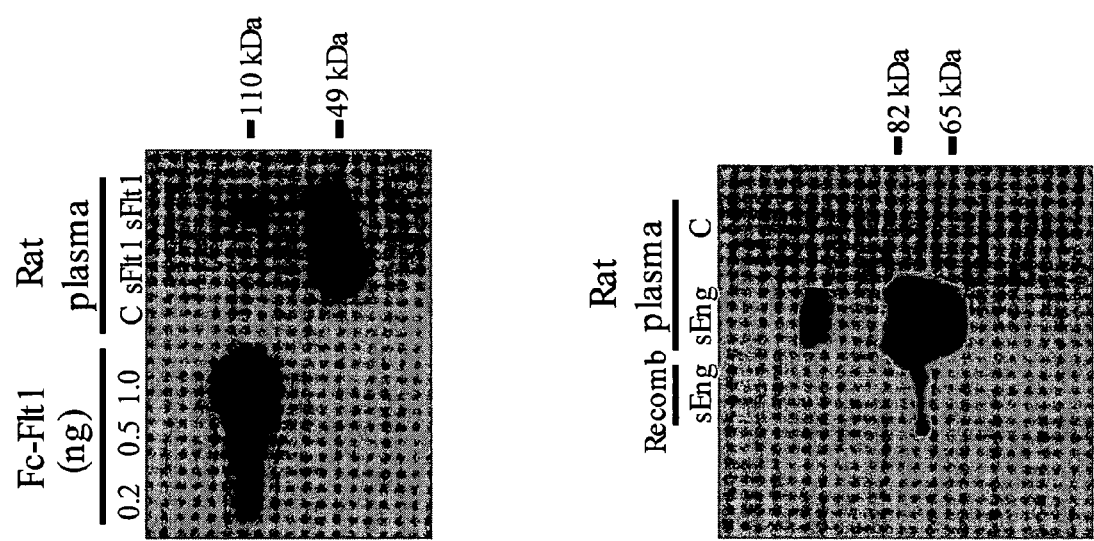
FIG. 36 shows two western blots of rat plasma demonstrating expression of the recombinant sFlt1 and soluble endoglin. Upper panel: Plasma specimens from pregnant rats (at early third trimester) were used as described in Methods. Lanes 1, 2 and 3 represent 200 pg, 500 pg and 2 ng of recombinant mouse Flt1-Fc protein used as a positive control. 20 μl of plasma specimens from one control rat and two sFlt1 treated rats are shown. sFlt1 (53 kDa) band was detected in the sFlt1 treated rats. Quantitation of the sFlt1 expression was performed using commercially available ELISA (Table 8). Lower panel: Plasma specimens from pregnant rats were used (at early third trimester) to detect sEng expression. Lane 1 represents 500 pg of recombinant human soluble endoglin and lanes 2 and 3 represent 30 μl of plasma from sEng treated and control rats respectively. The blot shows no soluble endoglin in control rats but robust expression of recombinant sEng in treated rats. Quantitation of soluble endoglin was performed using a commercially available ELISA (Table 8).

MAP—mean arterial pressure (diastolic pressure + ⅓ pulse pressure); Alb/Creat—Albumin/creatinine ratios; LDH—Lactate dyhyrogenase; AST—Aspartate Aminotransferase.
*P < 0.05 when compared to control group.
Fetal weight is the sum of 4 fetuses chosen randomly per group.
Expression of sFlt1 and sEng were first confirmed in rat plasma by Western blots (FIG. 36) and circulating concentration quantified using commercially available ELISA kits.
The average circulating concentrations of sFlt1 was 410 ng/ml in the sFlt1 group and 430 ng/ml in the sFlt1 + sE group. Average circulating concentrations of sE was 318 ng/ml in the sE group and 319 ng/ml in the sFlt1 + sE group.

Figure 26A:
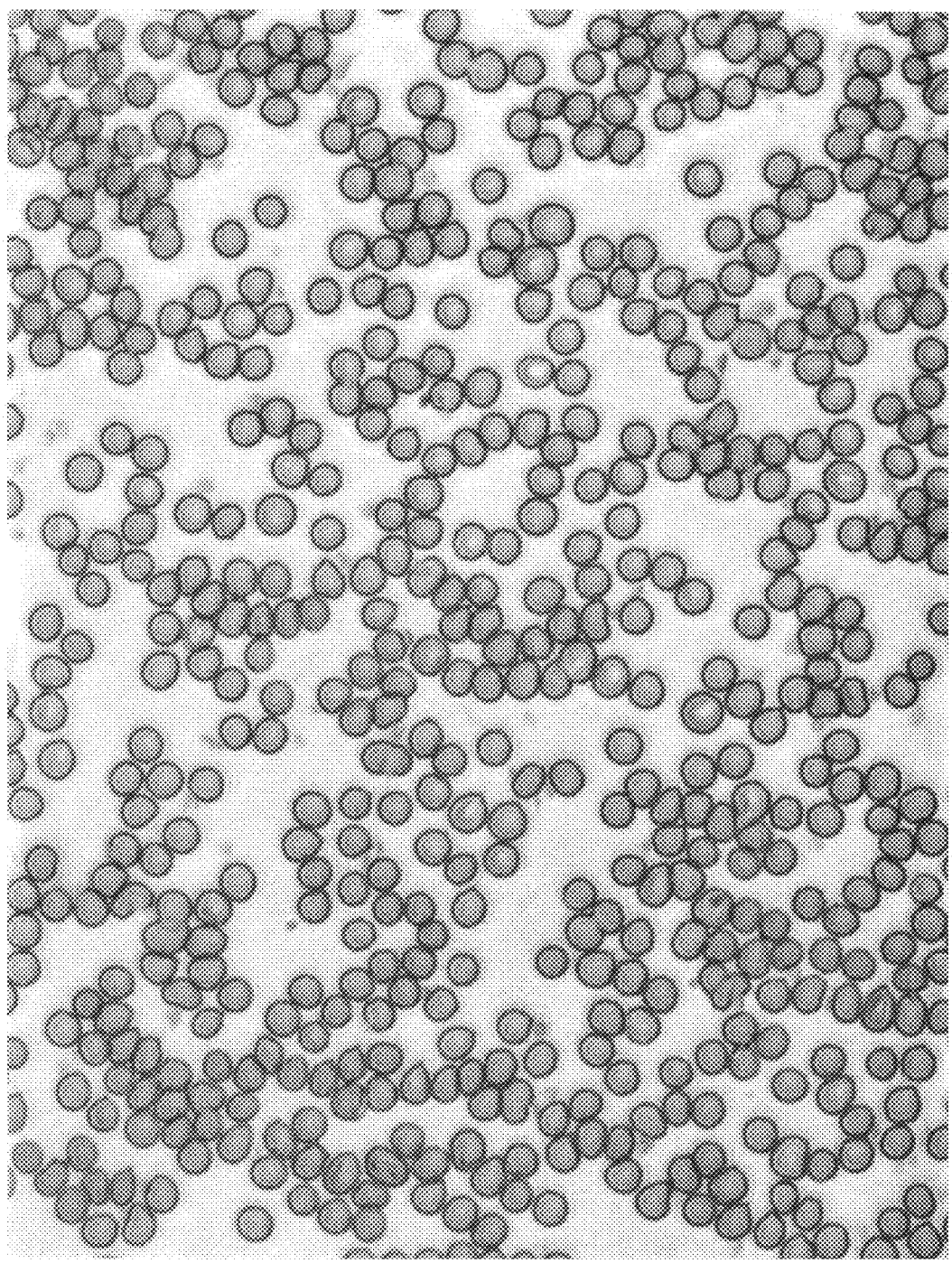
FIG. 26A is a photograph of a peripheral smear of blood samples taken at the time of sacrifice from pregnant rats injected with the combination of sFlt1 and a control adenoviruses (CMV).
Figure 26B:
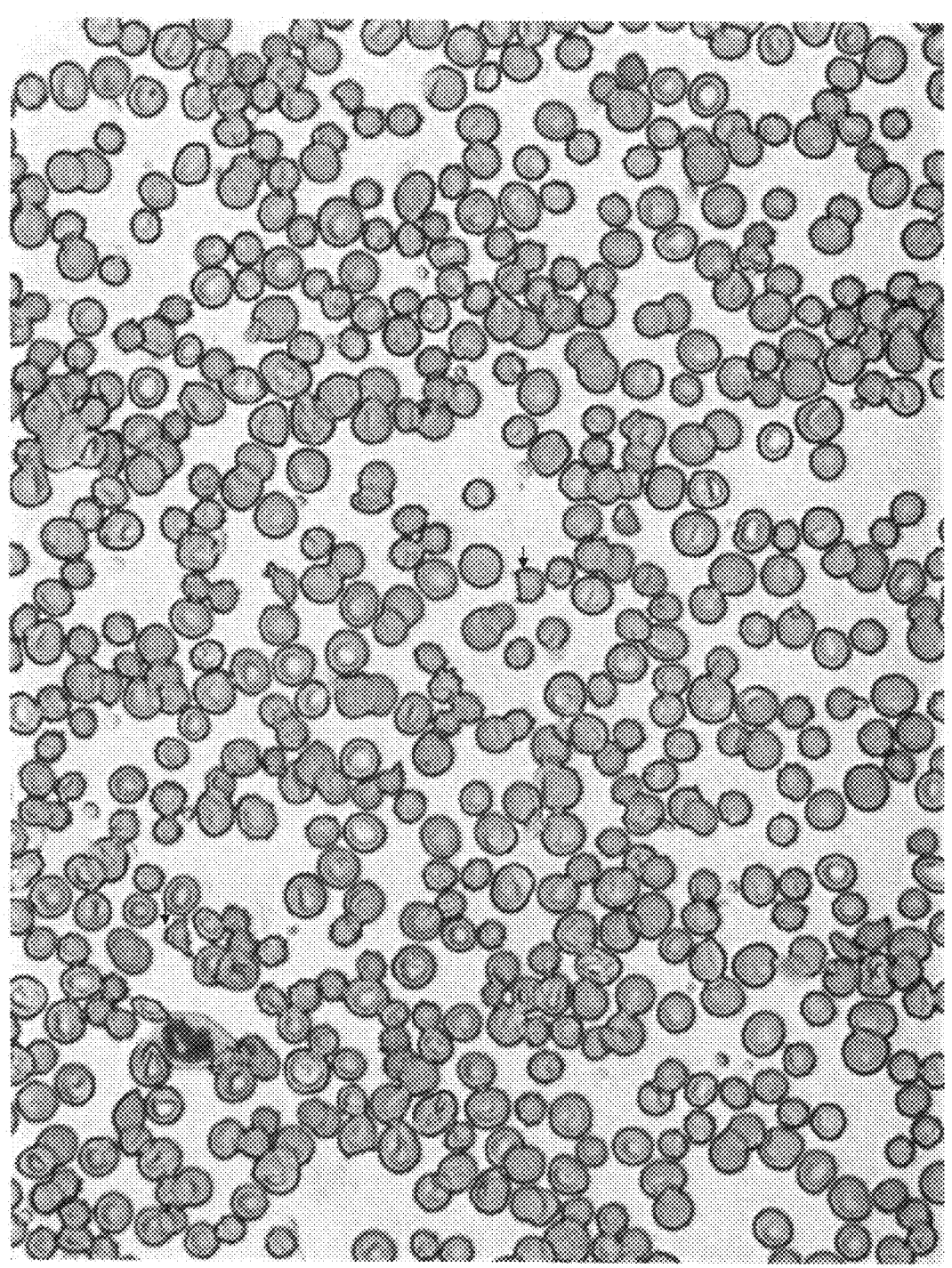
FIG. 26B is a photograph of a peripheral smear of blood samples taken at the time of sacrifice from pregnant rats injected with the combination of sFlt and adenoviruses expressing soluble endoglin and demonstrates active hemolysis as evidenced by schistocytes and increased reticulocyte count. Arrowheads represent schistocyte.
Figure 27:
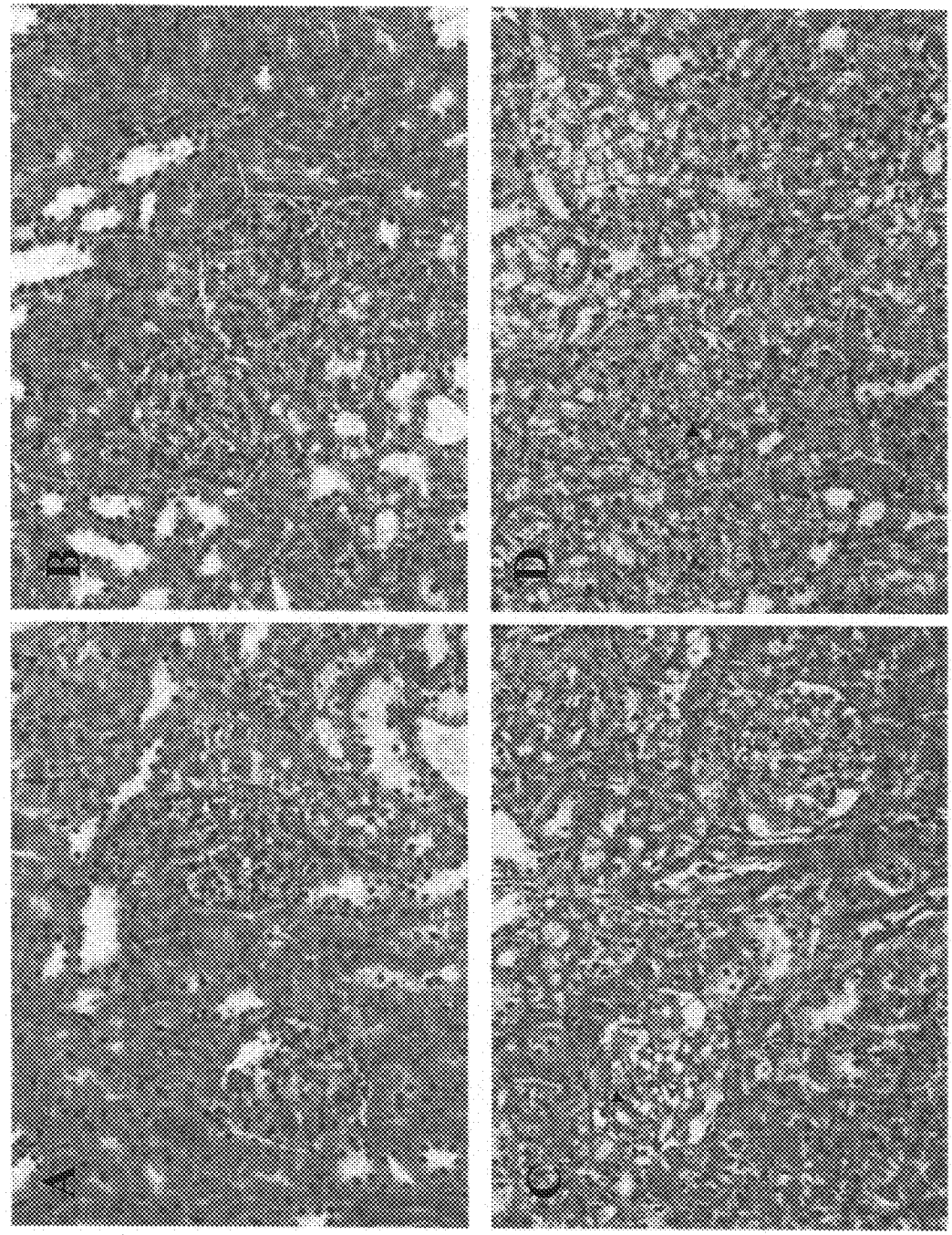
FIGS. 27A-D are a series of photomicrographs showing the renal histology (H &E stain) of the various animal groups described in Table 8.

Soluble endoglin alone induced a mild hypertension. sFlt1 induced both hypertension and proteinuria, as previously reported. Fetal growth restriction was observed in litters born to the sFlt1+sEng group, probably related to the placental vascular ischemia and damage. Importantly, the combination of sFlt1 and soluble endoglin induced severe hypertension, nephrotic range proteinuria, growth restriction of the fetuses and biochemical evidence of the development of the HELLP syndrome (elevated LDH, elevated AST and decreasing platelet counts) (Table 8). Evidence of hemolysis in the soluble endoglin+sFlt1 group was confirmed by peripheral smear which revealed schistocytes and reticulocytosis (FIGS. 26A-B). Finally, renal histology also revealed focal endotheliosis in the soluble endoglin group and a severe glomerular endotheliosis in the soluble endoglin+sFlt1 group (FIGS. 27A-27D, and 33). Note that in FIG. 33, the control group is within normal limits. Note open capillary loops with fenestrated endothelium. The soluble endoglin panel shows endothelial swelling with loss of fenestrae and partial luminal occlusion. Note a red blood cell squeezing through the compromised lumen. While light microscopy of the kidneys of soluble endoglin treated rats was not striking for significant endotheliosis, electron microscopy revealed focal endotheliosis. Importantly, the animals that received both soluble endoglin and sFlt-1 had severe glomerular endotheliosis. The combination therapy group (lower panel) shows massive endocapillary occlusion with swollen endothelial cells. Note the relative preservation of podocyte foot processes (shown as arrows) despite severe proteinuria. Extensive vascular damage of the placenta including infarction at the maternal-fetal junction was observed in the sFlt1+sEng group, but not in control rats or in those treated with either agent alone (FIGS. 34A-H). Diffuse inflammation in the giant cell layer (corresponding to human invasive trophoblasts) was noted in the sFlt1 and sEng groups, and was higher in the combined group. Liver histology revealed signs of ischemia and areas of necrosis in the sFlt1+sEng group, similar to those seen in patients with the HELLP syndrome (FIGS. 34A-H). Signs of severe maternal vascular damage were also seen when sFlt1+sEng were injected to non-pregnant rats, suggesting that the observed phenotype in pregnant rats was due to a direct effect on the maternal vessels and did not require the placenta.

Summary

These results demonstrate that soluble endoglin is up-regulated in pre-eclamptic placentas and is present at extremely high levels in patients with pre-eclampsia. The highest levels of soluble endoglin were present in patients with HELLP syndrome, one of the most severe forms of pre-eclampsia. These results also demonstrate that soluble endoglin levels correlated with the elevated sFlt1 in pregnant patients and was higher in those patients in whom there is a higher circulating sFlt1 levels. In addition, the results indicate that soluble endoglin is an anti-angiogenic molecule and disrupts endothelial function in multiple endothelial assays such as angiogenesis assays, microvascular permeability assays, and microvascular reactivity experiments. Importantly, soluble endoglin can amplify the toxic consequence of sFlt1 in these in vitro endothelial assays. Further, in in vivo assays, adenoviral expression of soluble endoglin induces mild hypertension without any significant proteinuria. However, in the presence of sFlt1, soluble endoglin induces significant vascular damage as evidenced by the presence of severe hypertension, proteinuria, glomerular endotheliosis, development of the HELLP syndrome and fetal growth restriction.

The mechanism of soluble endoglin release is likely proteolytic cleavage of the extracellular region of the endoglin molecule. Specific proteases that are up-regulated in the pre-eclamptic tissue may serve as candidate molecules. One example would be the membrane type matrix metalloproteinase-1 (MT1-MMP) that has been shown to cleave betaglycan, a molecule that shares similarity to endoglin (Velasco-Loyden G et al, *J. Biol. Chem.* 279:7721-33 (2004)). Therefore, inhibitors of such proteases can serve as valuable targets for the treatment of pre-eclampsia.

Example 8

Figure 35A:
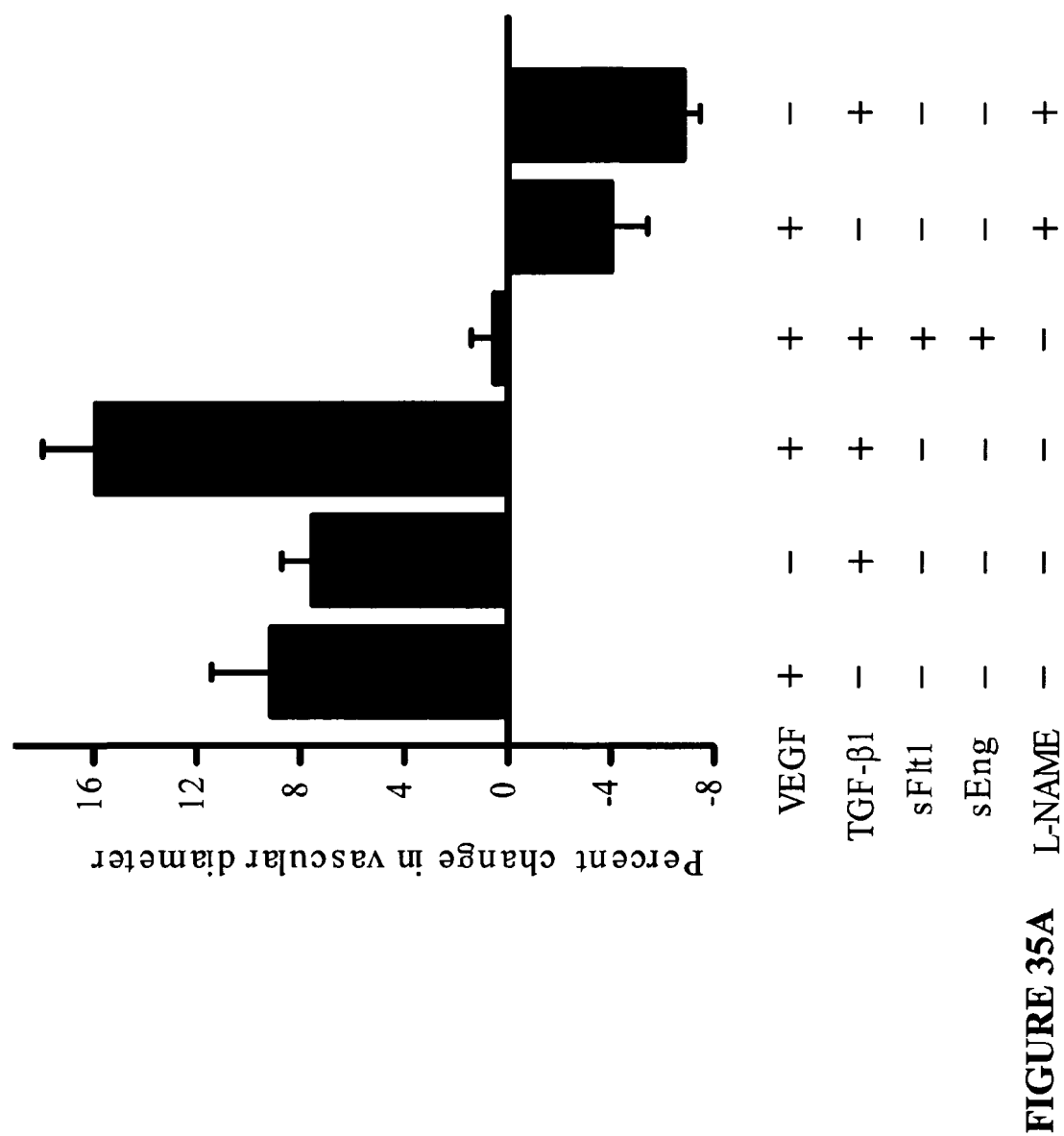

Soluble Endoglin Inhibits TGF-β1 and TGF-β3 Mediated NOS-Dependent Vasodilation eNOS is a $Ca^{2+}$/calmodulin-regulated nitric oxide (NO) synthase that can be activated by fluid shear stress and neurohumoral stimuli. Endothelium-derived NO is a very potent vasorelaxant contributing to systemic blood pressure regulation, vascular permeability, and angiogenesis. In fact, the effects of VEGF on angiogenesis and vascular tone are partly mediated by activation of eNOS, through increased eNOS/Hsp90 association and Akt-dependent eNOS phosphorylation at Ser1177. Our recent demonstration that increased placenta-derived sFlt1 in sera of preeclamptic patients is anti-angiogenic and induces hypertension may in fact reflect impaired VEGF-dependent eNOS activation (Maynard et al., supra). More recently, dephosphorylation of eNOS Thr495 has been shown to precede Ser1177 phosphorylation and these coordinated events determine eNOS activity in endothelial cells (Fleming et al., *Cir. Res.* 88:E68-75 (2001)). Given the known effect of VEGF on reducing vascular reactivity via eNOS activation and the recent demonstration that endoglin modulates eNOS-dependent vasomotor activity (Toporsian et al., *Circ. Res.* 96:684-692 (2005)), we assessed the hemodynamic effects of TGF-β isoforms and soluble endoglin in isolated rat renal microvessels. As described in Example 7 and in FIGS. 24 and 25, both TGF-β1 and -β3 induced a dose-dependent increase in arterial diameter which was significantly attenuated by soluble endoglin. This acute effect of TGF-β1 and -β3 isoforms on vascular tone has not been previously recognized and was also seen in mesenteric vessels (FIG. 32). VEGF and TGF-β1 had additive effects on vasodilation, which were blocked by sEng+sFlt1 at concentrations noted in patients with preeclampsia (FIGS. 25 and 35A). L-NAME blocked the vasodilation mediated by TGF-β1 and VEGF indicating a NOS dependent response (FIG. 35A). These data suggest that circulating sFlt1 and sEng may oppose the physiological NO-dependent vasodilatation elicited by these angiogenic growth factors, contributing to the development of hypertension seen in preeclampsia.

Example 9

Figure 35B:
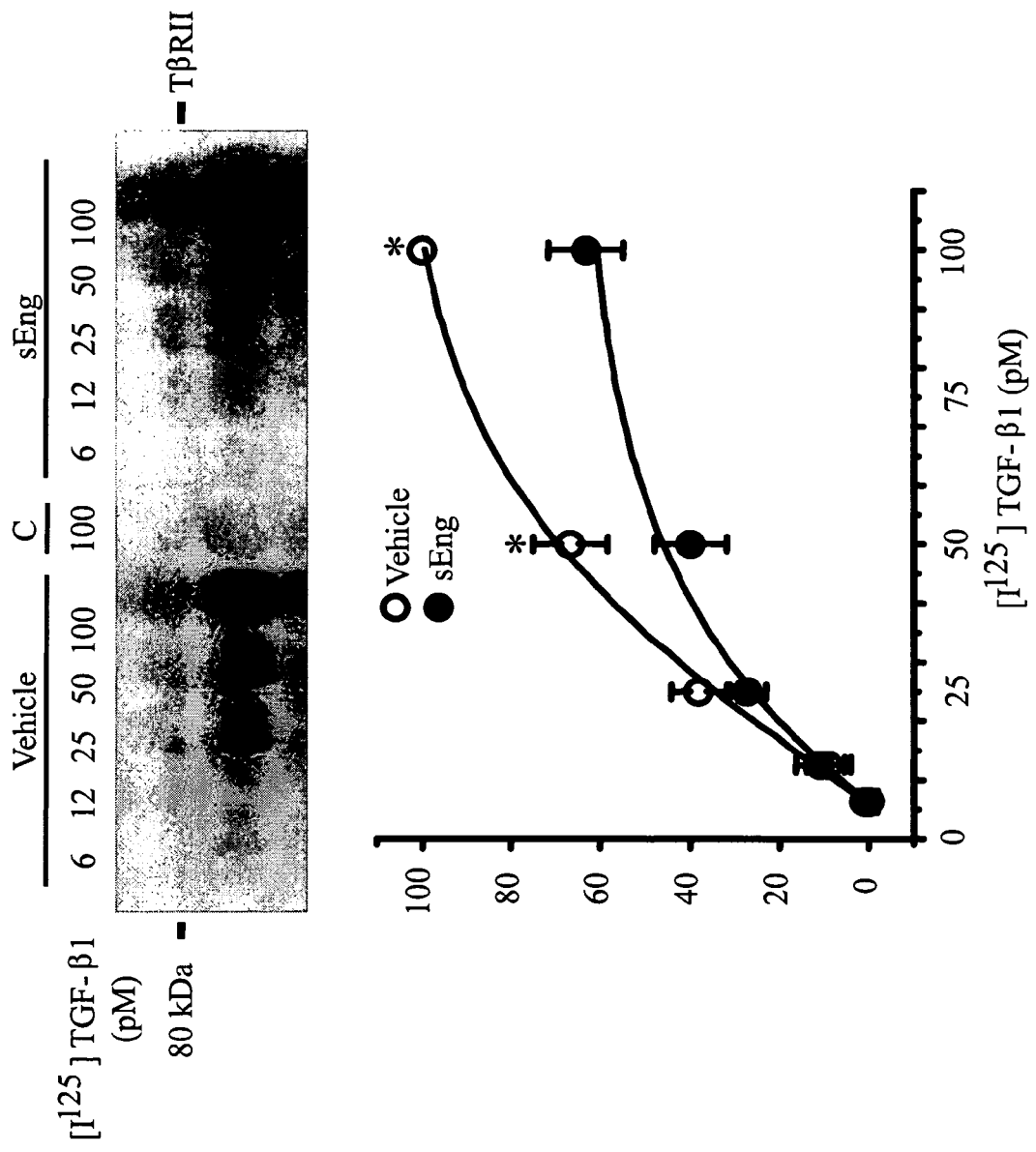
Figure 35C:
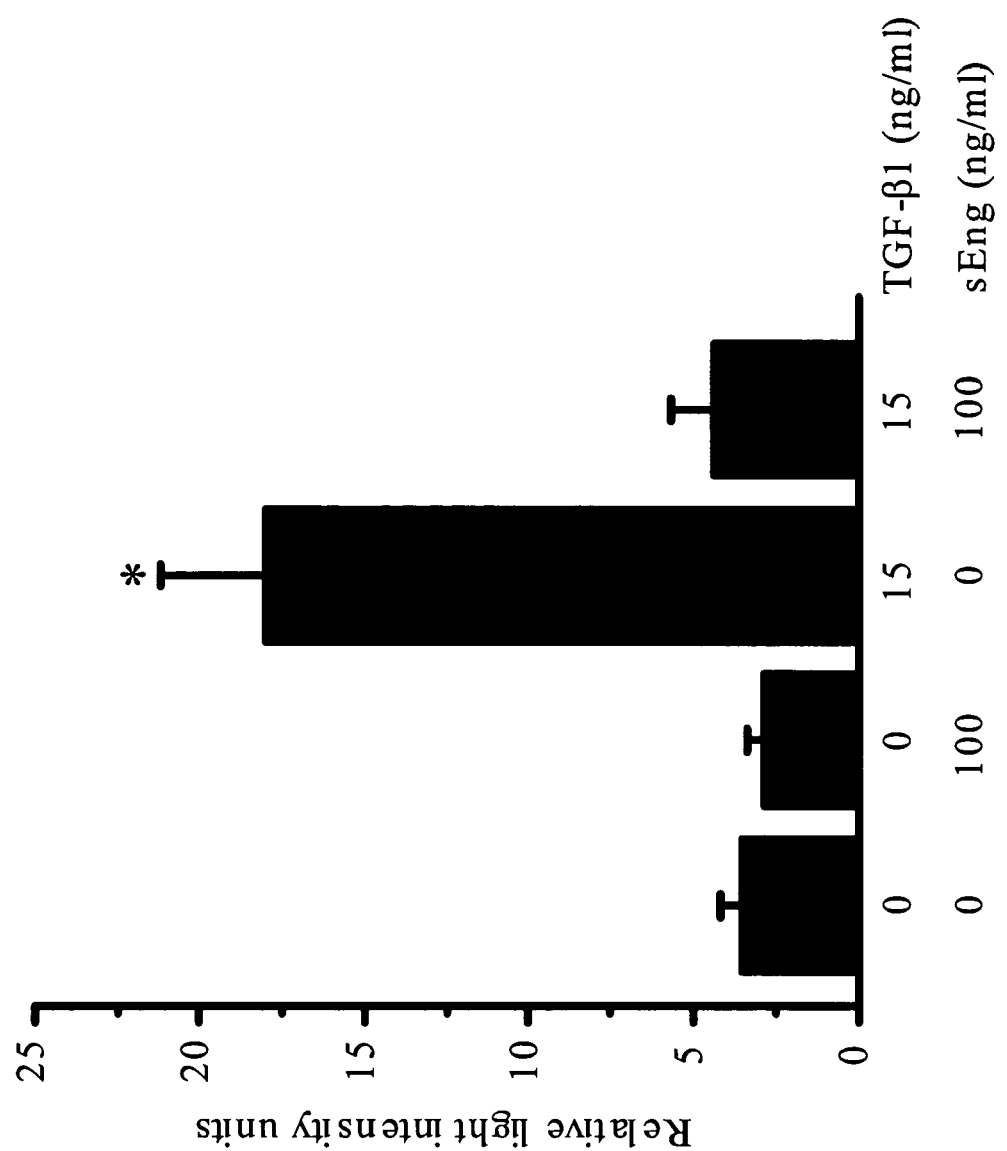

Soluble Endoglin Inhibits TGF-β1 Binding and Signaling in Endothelial Cells Given that endoglin is a co-receptor for TGF-β1 and -β3 isoforms, we hypothesized that soluble endoglin acts by interfering with cell surface receptor binding. Pre-incubating radio-labeled TGF-β1 with recombinant soluble endoglin significantly reduced its binding to TGF-β receptor type II (TβRII) at both 50 and 100 pM (FIG. 35B). Thus soluble endoglin competes for TGF-β1 binding to its receptors on endothelial cells. To test whether this leads to impaired signaling, the activity of a CAGA-Luc reporter construct was assessed in human endothelial cells. TGF-β1 induced the activation of the Smad 2/3-dependent CAGA-Luc reporter and this response was abolished by treatment with soluble endoglin (FIG. 35C).

Example 10

Soluble Endoglin Blocks TGF-β1 Mediated eNOS Activation

Given our findings that TGF-β1 induces a NOS-dependent vasorelaxation in both renal and mesenteric resistance vessels, we explored its immediate effects on eNOS activation. While TGF-β1 had no effect on eNOS Ser1177 phosphorylation, it induced a significant dephosphorylation at Thr495 (FIG. 35D) suggesting that TGF-β regulates the phosphorylation status of a key residue in eNOS activation. This effect was significantly attenuated by soluble endoglin (FIG. 35D).

Taken together, the results in Examples 8-10 demonstrate that soluble endoglin interferes with TGF-β receptor binding and downstream signaling in endothelial cells and attenuates eNOS activation. Soluble endoglin and sFlt-1 may be working in concert to inhibit endothelial dependent NO activation and vasomotor effects by both the VEGF and the TGF-β signaling pathways.

Other Embodiments

The description of the specific embodiments of the invention is presented for the purposes of illustration. It is not intended to be exhaustive or to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications, and publications referenced herein are hereby incorporated by reference.

Other embodiments are in the claims.

---

What is claimed is:

1. A method of treating a pregnancy related hypertensive disorder in a subject on or after the 20$^{th}$ week of pregnancy, said method comprising the step of administering to said subject (i) a compound capable of decreasing soluble endoglin expression levels or soluble endoglin biological activity, wherein said compound is an antibody that specifically binds soluble endoglin, or a soluble endoglin antigen binding fragment thereof, or a growth factor that binds to soluble endoglin and (ii) a compound capable of decreasing sFlt-1 expression levels or sFlt-1 biological activity, wherein said compound is an antibody that specifically binds sFlt-1, or an sFlt-1 antigen binding fragment thereof, or a growth factor that binds to sFlt-1, wherein said administering is on or after the 20$^{th}$ week of the pregnancy of said subject and wherein said administering is for a time and in an amount sufficient to treat said pregnancy related hypertensive disorder in said subject.

2. The method of claim 1, wherein said pregnancy related hypertensive disorder is selected from the group consisting of pre-eclampsia, eclampsia, gestational hypertension, chronic hypertension, HELLP syndrome, and pregnancy with a small for gestational age (SGA) infant.

3. The method of claim 2, wherein said pregnancy related hypertensive disorder is pre-eclampsia or eclampsia.

4. The method claim 1, wherein said compound capable of decreasing soluble endoglin expression levels or soluble endoglin biological activity is an antibody that specifically binds soluble endoglin, or a soluble endoglin antigen-binding fragment thereof.

5. The method of claim 1, wherein said compound capable of decreasing soluble endoglin expression levels or soluble endoglin biological activity is a growth factor that binds to soluble endoglin.

6. The method of claim 5, wherein said growth factor that binds to soluble endoglin is selected from the group consisting of transforming growth factor (TGF)-β1, TGF-β3, activin A, Bone Morphogenic Protein (BMP)-2, BMP-7, and fragments thereof.

7. The method of claim 1, wherein said compound capable of decreasing sFlt-1 expression levels or sFlt-1 biological activity is an antibody that specifically binds sFlt-1 or an sFlt-1 antigen-binding fragment thereof.

8. The method of claim 1, wherein said growth factor that binds to sFlt-1 is vascular endothelial growth factor (VEGF).

9. The method of claim 8, wherein said VEGF is VEGF121, VEGF165, or a modified form of VEGF.

10. The method of claim 1, wherein growth factor that binds to sFlt-1 is placental growth factor (PlGF) or isoforms thereof.

11. The method of claim 1, further comprising the step of administering to a subject an anti-hypertensive compound.

12. The method of claim 1, wherein said subject is a pregnant human, a post-partum human, or a non-human.

13. The method of claim 1, wherein said subject has increased soluble endoglin polypeptide or nucleic acid expression levels relative to a normal reference sample or level.

14. The method of claim 13, wherein said normal reference sample or level is a prior sample or level from said subject.

15. The method of claim 13, wherein the increase in said soluble endoglin level relative to said normal reference sample or level is at least 10%.

16. The method of claim 13, wherein said increased soluble endoglin polypeptide expression level is a level of at least 20 ng/ml.

17. A method for delaying or ameliorating at least one symptom of pre-eclampsia or eclampsia in a subject diagnosed as having an increased risk for developing pre-eclampsia or eclampsia, wherein said subject is on or after the $20^{th}$ week of pregnancy, said method comprising administering to said subject (i) a compound capable of decreasing soluble endoglin expression levels or soluble endoglin biological activity, wherein said compound is an antibody that specifically binds soluble endoglin, or a soluble endoglin antigen binding fragment thereof, or a growth factor that binds to soluble endoglin and (ii) a compound capable of decreasing sFlt-1 expression levels or sFlt-1 biological activity, wherein said compound is an antibody that specifically binds sFlt-1, or an sFlt-1 antigen binding fragment thereof, or a growth factor that binds to sFlt-1, wherein said at least one symptom is selected from the group consisting of a systolic blood pressure greater than 140 mmHg and a diastolic blood pressure greater than 90 mmHg after 20 weeks gestation; new onset proteinuria; greater than 300 mg of protein in a 24-hour urine collection; and a single random urine sample having a protein/creatinine ratio greater than 0.3, and wherein said administering is in an amount sufficient to delay or ameliorate at least one of said symptoms of pre-eclampsia or eclampsia in said subject, said subject having increased soluble endoglin or sFlt-1 polypeptide or nucleic acid expression levels of at least 10% relative to a normal reference sample or level.

18. The method of claim 17, wherein said administering is prior to the onset of at least one of said symptoms of pre-eclampsia or eclampsia.

19. The method of claim 17, wherein said administering begins when the level of soluble endoglin or sFlt-1 is increased by at least 2-fold relative to levels in a normal control subject.

20. The method of claim 17, wherein said increased soluble endoglin polypeptide expression levels is a level of at least 20 ng/ml.

21. The method of claim 17, wherein said increased sFlt-1 polypeptide expression levels is a level of at least 2 ng/ml.

22. The method of claim 13, wherein said subject is 24-28 weeks pregnant.

23. The method of claim 13, wherein said subject is 28-32 weeks pregnant.

24. The method of claim 13, wherein said subject is 32-36 weeks pregnant.

25. The method of claim 13, wherein said subject is greater than 36 weeks pregnant.

26. The method of claim 3, wherein said pre-eclampsia is premature pre-eclampsia.

27. The method of claim 26, wherein said premature pre-eclampsia has an onset of symptoms of less than 34 weeks.

28. A method of treating a pregnancy related hypertensive disorder in a subject on or after the $20^{th}$ week of pregnancy, said method comprising the step of providing ex vivo to said subject (i) a compound capable of decreasing soluble endoglin expression levels or soluble endoglin biological activity, wherein said compound is an antibody that specifically binds soluble endoglin, or a soluble endoglin antigen binding fragment thereof, or a growth factor that binds to soluble endoglin and (ii) a compound capable of decreasing sFlt-1 expression levels or sFlt-1 biological activity, wherein said compound is an antibody that specifically binds sFlt-1, or an sFlt-1 antigen binding fragment thereof, or a growth factor that binds to sFlt-1, wherein said providing is on or after the $20^{th}$ week of pregnancy of said subject and wherein said providing is for a time and in an amount sufficient to treat said pregnancy related hypertensive disorder in said subject.

29. The method of claim 28, wherein said providing ex vivo comprises circulating the subject's blood through a column comprising said compound (i) and said compound (ii).

30. The method of claim 28, wherein said compound (i) is an antibody that specifically binds soluble endoglin, or a soluble endoglin antigen-binding fragment thereof and wherein said compound (ii) is an antibody that specifically binds sFlt-1 or an sFlt-1 antigen binding fragment thereof.

31. The method of claim 28, wherein said pregnancy related hypertensive disorder is selected from the group consisting of pre-eclampsia, eclampsia, gestational hypertension, chronic hypertension, HELLP syndrome, and pregnancy with a small for gestational age (SGA) infant.

32. The method of claim 31, wherein said pregnancy related hypertensive disorder is pre-eclampsia or eclampsia.

33. The method of claim 32, wherein said pregnancy related hypertensive disorder is premature pre-eclampsia.

34. The method of claim 33, wherein said premature pre-eclampsia has an onset of symptoms of less than 34 weeks.

35. The method of claim 28, wherein said subject has increased soluble endoglin or sFlt-1 polypeptide or nucleic acid expression levels of at least 10% relative to a normal reference sample or level.

36. The method of claim 35, wherein said increased soluble endoglin polypeptide expression levels is a level of at least 20 ng/ml.

37. The method of claim 35, wherein said increased sFlt-1 polypeptide expression levels is a level of at least 2 ng/ml.

* * * * *

UNITED STATES PATENT AND TRADEMARK OFFICE
CERTIFICATE OF CORRECTION

PATENT NO. : 7,740,849 B2
APPLICATION NO. : 11/443920
DATED : June 22, 2010
INVENTOR(S) : Karumanchi et al.

It is certified that error appears in the above-identified patent and that said Letters Patent is hereby corrected as shown below:

On Title page, Item (73) Assignees, replace "Sick Children (CA)" with --Sick Children, Toronto (CA)--;

On Title page, Item (56) References Cited, under U.S. PATENT DOCUMENTS, in Durley et al., replace "11/2005" with --7/2005--.

On Title page 2, Item (56) under OTHER PUBLICATIONS, 1st column, in Ahmed et al., replace "Oxygen- A Review" with --Oxygen – A Review--.

On Title page 3, Item (56) 1st column, in Luttun et al., replace "Preclampsia" with --Preeclampsia--.

Column 1, Line 55, replace "unbilical" with --umbilical--.

Column 3, Line 58, replace "infant" with --baby--.

Column 4, Line 12, replace "increases" with --increase--.

Column 5, Line 11, replace "and" with --or--.

Column 7, Line 26, replace "995%" with --95%--.

Column 8, Lines 3-4, replace "Smad 2/3 dependent" with --Smad 2/3-dependent--.

Column 10, Line 60, replace "less that" with --less than--;

Line 60, replace "10" with --the 10--;

Line 60, replace "10" with --10th--;

Signed and Sealed this
Seventeenth Day of July, 2012

David J. Kappos
*Director of the United States Patent and Trademark Office*

Line 61, replace "percent" with --percentile--.

Column 12, Line 41, replace "683-6" with --683-686--;

Line 50, replace "infant" with --baby--;

Line 51, replace "infant" with --baby--.

Column 14, Line 16, replace "sample" with --sample.--.

Column 15, Line 48, replace "195-7" with --195-197--;

Line 54, replace "403-10" with --403-410--.

Column 16, Line 55, replace "753-91" with --753-791--;

Line 58, replace "would" with --wound--.

Column 19, Line 37, replace "blots" with --blot--.

Column 20, Line 53, replace "represents" with --represent--.

Column 23, line 36, replace "infant" with --baby--.

Column 25, Line 2, replace "Another" with --Other--;

Line 2, replace "example" with --examples--;

Line 2, replace "indexs" with --indexes--.

Column 26, Line 34, replace "and in" with --and an--;

Line 38, replace "include" with --includes--.

Column 27, Line 38, replace "described U.S." with --described in U.S.--.

Column 29, Line 24, replace "factor." with --factors.--.

Column 32, Line 42, replace "Postranslational" with --Posttranslational-- .

Column 33, Line 58, replace "reproduced" with --reproduce--.

Column 34, Line 1, replace "large" with --a large--.

Column 35, Line 33, replace "88" with --4988--.

CERTIFICATE OF CORRECTION (continued)
U.S. Pat. No. 7,740,849 B2

Column 38, Line 39, replace "A. R. Gennaro A R" with --A. R. Gennaro--.

Column 44, Line 42, replace "(2001)))." With --(2001)).--.

Column 46, Line 30, replace "infants" with --babies--.

Column 50, Line 29, replace "was" with --were--;

Table 6, under 3$^{rd}$ blood sampling, replace "0.001*" with --<0.001*--.

Column 53, Line 24, replace "complication" with --complications--;

Line 26, replace "infants" with --babies--;

Line 35, replace "infants" with --babies--;

Line 47, replace "infants" with --babies--.

Column 54, Line 57, replace "infants" with --babies--.

Column 59, Line 7, replace "TGF-β3-two" with --TGF-β3 – two--.

Column 69, Line 67, Claim 2, replace "infant" with --baby--.

Column 72, Line 42, Claim 31, replace "infant" with --baby--.

SEQUENCE LISTING

<160> NUMBER OF SEQ ID NOS: 5

<210> SEQ ID NO 1
<211> LENGTH: 1311
<212> TYPE: DNA
<213> ORGANISM: Homo sapiens

<400> SEQUENCE: 1
atggaccgcg gcacgctccc tctggctgtt gccctgctgc tggccagctg cagcctcagc      60

-continued

| | |
|---|---|
| cccacaagtc ttgcagaaac agtccattgt gaccttcagc ctgtgggccc cgagagggac | 120 |
| gaggtgacat ataccactag ccaggtctcg aagggctgcg tggctcaggc ccccaatgcc | 180 |
| atccttgaag tccatgtcct cttcctggag ttcccaacgg gcccgtcaca gctggagctg | 240 |
| actctccagg catccaagca aaatggcacc tggccccgag aggtgcttct ggtcctcagt | 300 |
| gtaaacagca gtgtcttcct gcatctccag gccctgggaa tcccactgca cttggcctac | 360 |
| aattccagcc tggtcacctt ccaagagccc ccgggggtca acaccacaga gctgccatcc | 420 |
| ttccccaaga cccagatcct tgagtgggca gctgagaggg gccccatcac ctctgctgct | 480 |
| gagctgaatg accccagag catcctcctc cgactgggcc aagcccaggg gtcactgtcc | 540 |
| ttctgcatgc tggaagccag ccaggacatg ggccgcacgc tcgagtggcg gccgcgtact | 600 |
| ccagccttgg tccggggctg ccacttggaa ggcgtggccg ccacaagga ggcgcacatc | 660 |
| ctgagggtcc tgccgggcca ctcggccggg cccggacgg tgacggtgaa ggtggaactg | 720 |
| agctgcgcac ccggggatct cgatgccgtc ctcatcctgc agggtccccc ctacgtgtcc | 780 |
| tggctcatcg acgccaacca caacatgcag atctggacca ctggagaata ctccttcaag | 840 |
| atctttccag agaaaaacat tcgtggcttc aagctcccag acacacctca aggcctcctg | 900 |
| ggggaggccc ggatgctcaa tgccagcatt gtggcatcct tcgtggagct accgctggcc | 960 |
| agcattgtct cacttcatgc ctccagctgc ggtggtaggc tgcagacctc acccgcaccg | 1020 |
| atccagacca ctcctcccaa ggacacttgt agcccggagc tgctcatgtc cttgatccag | 1080 |
| acaaagtgtg ccgacgacgc catgaccctg gtactaaaga aagagcttgt tgcgcatttg | 1140 |
| aagtgcacca tcacgggcct gaccttctgg gaccccagct gtgaggcaga ggacaggggt | 1200 |
| gacaagtttg tcttgcgcag tgcttactcc agctgtggca tgcaggtgtc agcaagtatg | 1260 |
| atcagcaatg aggcggtggt caatatcctg tcgagctcat caccacagcg g | 1311 |

<210> SEQ ID NO 2
<211> LENGTH: 437
<212> TYPE: PRT
<213> ORGANISM: Homo sapiens

<400> SEQUENCE: 2

Met Asp Arg Gly Thr Leu Pro Leu Ala Val Ala Leu Leu Leu Ala Ser
1               5                   10                  15

Cys Ser Leu Ser Pro Thr Ser Leu Ala Glu Thr Val His Cys Asp Leu
            20                  25                  30

Gln Pro Val Gly Pro Glu Arg Gly Glu Val Thr Tyr Thr Thr Ser Gln
        35                  40                  45

Val Ser Lys Gly Cys Val Ala Gln Ala Pro Asn Ala Ile Leu Glu Val
    50                  55                  60

His Val Leu Phe Leu Glu Phe Pro Thr Gly Pro Ser Gln Leu Glu Leu
65                  70                  75                  80

Thr Leu Gln Ala Ser Lys Gln Asn Gly Thr Trp Pro Arg Glu Val Leu
                85                  90                  95

Leu Val Leu Ser Val Asn Ser Ser Val Phe Leu His Leu Gln Ala Leu
            100                 105                 110

Gly Ile Pro Leu His Leu Ala Tyr Asn Ser Ser Leu Val Thr Phe Gln
        115                 120                 125

Glu Pro Pro Gly Val Asn Thr Thr Glu Leu Pro Ser Phe Pro Lys Thr
    130                 135                 140

Gln Ile Leu Glu Trp Ala Ala Glu Arg Gly Pro Ile Thr Ser Ala Ala

```
        145                 150                 155                 160
Glu Leu Asn Asp Pro Gln Ser Ile Leu Leu Arg Leu Gly Gln Ala Gln
                165                 170                 175
Gly Ser Leu Ser Phe Cys Met Leu Glu Ala Ser Gln Asp Met Gly Arg
            180                 185                 190
Thr Leu Glu Trp Arg Pro Arg Thr Pro Ala Leu Val Arg Gly Cys His
        195                 200                 205
Leu Glu Gly Val Ala Gly His Lys Glu Ala His Ile Leu Arg Val Leu
    210                 215                 220
Pro Gly His Ser Ala Gly Pro Arg Thr Val Thr Val Lys Val Glu Leu
225                 230                 235                 240
Ser Cys Ala Pro Gly Asp Leu Asp Ala Val Leu Ile Leu Gln Gly Pro
                245                 250                 255
Pro Tyr Val Ser Trp Leu Ile Asp Ala Asn His Asn Met Gln Ile Trp
            260                 265                 270
Thr Thr Gly Glu Tyr Ser Phe Lys Ile Phe Pro Glu Lys Asn Ile Arg
        275                 280                 285
Gly Phe Lys Leu Pro Asp Thr Pro Gln Gly Leu Leu Gly Glu Ala Arg
    290                 295                 300
Met Leu Asn Ala Ser Ile Val Ala Ser Phe Val Glu Leu Pro Leu Ala
305                 310                 315                 320
Ser Ile Val Ser Leu His Ala Ser Ser Cys Gly Gly Arg Leu Gln Thr
                325                 330                 335
Ser Pro Ala Pro Ile Gln Thr Thr Pro Pro Lys Asp Thr Cys Ser Pro
            340                 345                 350
Glu Leu Leu Met Ser Leu Ile Gln Thr Lys Cys Ala Asp Asp Ala Met
        355                 360                 365
Thr Leu Val Leu Lys Lys Glu Leu Val Ala His Leu Lys Cys Thr Ile
    370                 375                 380
Thr Gly Leu Thr Phe Trp Asp Pro Ser Cys Glu Ala Glu Asp Arg Gly
385                 390                 395                 400
Asp Lys Phe Val Leu Arg Ser Ala Tyr Ser Ser Cys Gly Met Gln Val
                405                 410                 415
Ser Ala Ser Met Ile Ser Asn Glu Ala Val Val Asn Ile Leu Ser Ser
            420                 425                 430
Ser Ser Pro Gln Arg
        435

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
acgaagcttg aaacagtcca ttgtgacctt                                      30

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
ttagatatct ggcctttgct tgtgcaacc                                       29
```

<210> SEQ ID NO 5
<211> LENGTH: 633
<212> TYPE: PRT
<213> ORGANISM: Homo sapiens

<400> SEQUENCE: 5

```
Glu Thr Val His Cys Asp Leu Gln Pro Val Gly Pro Glu Arg Gly Glu
1               5                   10                  15

Val Thr Tyr Thr Thr Ser Gln Val Ser Lys Gly Cys Val Ala Gln Ala
            20                  25                  30

Pro Asn Ala Ile Leu Glu Val His Val Leu Phe Leu Glu Phe Pro Thr
        35                  40                  45

Gly Pro Ser Gln Leu Glu Leu Thr Leu Gln Ala Ser Lys Gln Asn Gly
    50                  55                  60

Thr Trp Pro Arg Glu Val Leu Leu Val Leu Ser Val Asn Ser Ser Val
65                  70                  75                  80

Phe Leu His Leu Gln Ala Leu Gly Ile Pro Leu His Leu Ala Tyr Asn
                85                  90                  95

Ser Ser Leu Val Thr Phe Gln Glu Pro Pro Gly Val Asn Thr Thr Glu
            100                 105                 110

Leu Pro Ser Phe Pro Lys Thr Gln Ile Leu Glu Trp Ala Ala Glu Arg
        115                 120                 125

Gly Pro Ile Thr Ser Ala Ala Glu Leu Asn Asp Pro Gln Ser Ile Leu
    130                 135                 140

Leu Arg Leu Gly Gln Ala Gln Gly Ser Leu Ser Phe Cys Met Leu Glu
145                 150                 155                 160

Ala Ser Gln Asp Met Gly Arg Thr Leu Glu Trp Arg Pro Arg Thr Pro
                165                 170                 175

Ala Leu Val Arg Gly Cys His Leu Glu Gly Val Ala Gly His Lys Glu
            180                 185                 190

Ala His Ile Leu Arg Val Leu Pro Gly His Ser Ala Gly Pro Arg Thr
        195                 200                 205

Val Thr Val Lys Val Glu Leu Ser Cys Ala Pro Gly Asp Leu Asp Ala
    210                 215                 220

Val Leu Ile Leu Gln Gly Pro Pro Tyr Val Ser Trp Leu Ile Asp Ala
225                 230                 235                 240

Asn His Asn Met Gln Ile Trp Thr Thr Gly Glu Tyr Ser Phe Lys Ile
                245                 250                 255

Phe Pro Glu Lys Asn Ile Arg Gly Phe Lys Leu Pro Asp Thr Pro Gln
            260                 265                 270

Gly Leu Leu Gly Glu Ala Arg Met Leu Asn Ala Ser Ile Val Ala Ser
        275                 280                 285

Phe Val Glu Leu Pro Leu Ala Ser Ile Val Ser Leu His Ala Ser Ser
    290                 295                 300

Cys Gly Gly Arg Leu Gln Thr Ser Pro Ala Pro Ile Gln Thr Thr Pro
305                 310                 315                 320

Pro Lys Asp Thr Cys Ser Pro Glu Leu Leu Met Ser Leu Ile Gln Thr
                325                 330                 335

Lys Cys Ala Asp Asp Ala Met Thr Leu Val Leu Lys Lys Glu Leu Val
            340                 345                 350

Ala His Leu Lys Cys Thr Ile Thr Gly Leu Thr Phe Trp Asp Pro Ser
        355                 360                 365

Cys Glu Ala Glu Asp Arg Gly Asp Lys Phe Val Leu Arg Ser Ala Tyr
```

-continued

```
            370                 375                 380
Ser Ser Cys Gly Met Gln Val Ser Ala Ser Met Ile Ser Asn Glu Ala
385                 390                 395                 400

Val Val Asn Ile Leu Ser Ser Ser Pro Gln Arg Lys Lys Val His
            405                 410                 415

Cys Leu Asn Met Asp Ser Leu Ser Phe Gln Leu Gly Leu Tyr Leu Ser
            420                 425                 430

Pro His Phe Leu Gln Ala Ser Asn Thr Ile Glu Pro Gly Gln Gln Ser
            435                 440                 445

Phe Val Gln Val Arg Val Ser Pro Ser Val Ser Glu Phe Leu Leu Gln
            450                 455                 460

Leu Asp Ser Cys His Leu Asp Leu Gly Pro Glu Gly Gly Thr Val Glu
465                 470                 475                 480

Leu Ile Gln Gly Arg Ala Ala Lys Gly Asn Cys Val Ser Leu Leu Ser
                485                 490                 495

Pro Ser Pro Glu Gly Asp Pro Arg Phe Ser Phe Leu Leu His Phe Tyr
                500                 505                 510

Thr Val Pro Ile Pro Lys Thr Gly Thr Leu Ser Cys Thr Val Ala Leu
            515                 520                 525

Arg Pro Lys Thr Gly Ser Gln Asp Gln Glu Val His Arg Thr Val Phe
            530                 535                 540

Met Arg Leu Asn Ile Ile Ser Pro Asp Leu Ser Gly Cys Thr Ser Lys
545                 550                 555                 560

Gly Leu Val Leu Pro Ala Val Leu Gly Ile Thr Phe Gly Ala Phe Leu
                565                 570                 575

Ile Gly Ala Leu Leu Thr Ala Ala Leu Trp Tyr Ile Tyr Ser His Thr
                580                 585                 590

Arg Ser Pro Ser Lys Arg Glu Pro Val Val Ala Val Ala Ala Pro Ala
            595                 600                 605

Ser Ser Glu Ser Ser Ser Thr Asn His Ser Ile Gly Ser Thr Gln Ser
    610                 615                 620

Thr Pro Cys Ser Thr Ser Ser Met Ala
625                 630
```